(12) United States Patent
Ammann et al.

(10) Patent No.: US 8,236,000 B2
(45) Date of Patent: Aug. 7, 2012

(54) METHOD AND APPARATUS FOR PERFORMING AN OPEN WEDGE, HIGH TIBIAL OSTEOTOMY

(75) Inventors: Kelly Ammann, Boulder, CO (US); Robert Schneider, Erie, CO (US); Bjorn Rindal, Broomfield, CO (US)

(73) Assignee: Arthrex, Inc., Naples, FL (US)

(*) Notice: Subject to any disclaimer, the term of this patent is extended or adjusted under 35 U.S.C. 154(b) by 408 days.

(21) Appl. No.: 12/603,150

(22) Filed: Oct. 21, 2009

(65) Prior Publication Data
US 2010/0145345 A1 Jun. 10, 2010

Related U.S. Application Data

(63) Continuation-in-part of application No. 11/047,159, filed on Jan. 31, 2005, and a continuation-in-part of application No. 11/047,551, filed on Jan. 31, 2005, now Pat. No. 8,083,746, and a continuation-in-part of application No. 11/352,103, filed on Feb. 9, 2006, and a continuation-in-part of application No. 11/350,333, filed on Feb. 8, 2006, and a continuation-in-part of application No. 11/396,490, filed on Apr. 3, 2006, and a continuation-in-part of application No. 11/607,321, filed on Dec. 1, 2006, now Pat. No. 7,967,823, and a continuation-in-part of application No. 11/644,218, filed on Dec. 22, 2006, now Pat. No. 7,935,119, and a continuation-in-part of application No. 11/888,506, filed on Aug. 1, 2007.

(60) Provisional application No. 61/196,852, filed on Oct. 21, 2008.

(51) Int. Cl.
*A61B 17/56* (2006.01)
(52) U.S. Cl. ........................................................ 606/87
(58) Field of Classification Search .................. 600/201; 606/53, 87–90, 96, 102, 105; 623/17.11, 623/17.16, 20.32, 20.34
See application file for complete search history.

(56) References Cited

U.S. PATENT DOCUMENTS

| 3,750,652 A * | 8/1973 | Sherwin ........................ 606/90 |
| 5,308,349 A * | 5/1994 | Mikhail ........................ 606/88 |
| 5,364,402 A * | 11/1994 | Mumme et al. ................. 606/88 |
| 2005/0075641 A1 * | 4/2005 | Singhatat et al. ............... 606/86 |

* cited by examiner

*Primary Examiner* — Eduardo C Robert
*Assistant Examiner* — David Comstock
(74) *Attorney, Agent, or Firm* — Dickstein Shapiro LLP

(57) ABSTRACT

The present invention comprises a novel method and apparatus for performing an open wedge, high tibial osteotomy. More particularly, the present invention comprises the provision and use of a novel method and apparatus for forming an appropriate osteotomy cut into the upper portion of the tibia, manipulating the tibia so as to open an appropriate wedge-like opening in the tibia, and then mounting an appropriately-shaped implant at the wedge-like opening in the tibia, so as to stabilize the tibia with the desired orientation, whereby to reorient the lower portion of the tibia relative to the tibial plateau and hence adjust the manner in which load is transferred from the femur to the tibia.

19 Claims, 72 Drawing Sheets

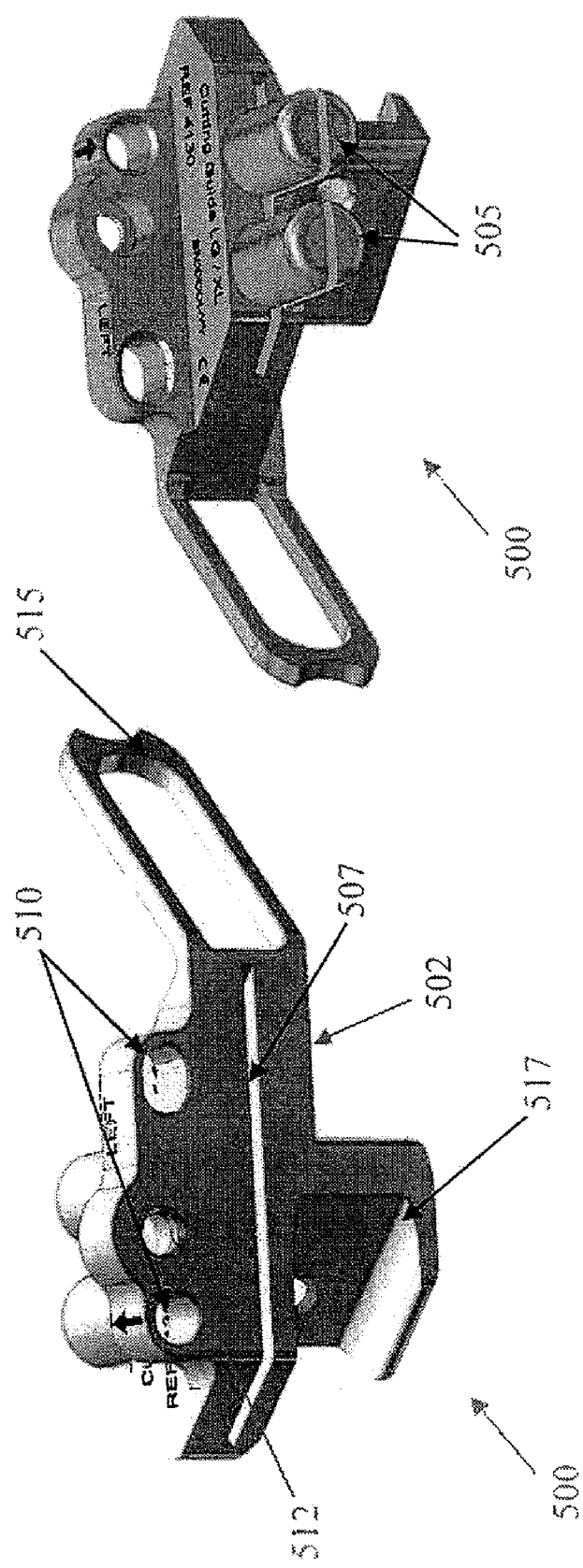

METHOD AND APPARATUS FOR PERFORMING AN OPEN WEDGE, HIGH TIBIAL OSTEOTOMY

REFERENCE TO PENDING PRIOR PATENT APPLICATIONS

This patent application:

(i) is a continuation-in-part of pending prior U.S. patent application Ser. No. 11/047,159, filed Jan. 31, 2005 by Vincent P. Novak for OPEN WEDGE OSTEOTOMY SYSTEM AND SURGICAL METHOD;

(ii) is a continuation-in-part of prior U.S. patent application Ser. No. 11/047,551, filed Jan. 31, 2005 by Vincent P. Novak for OPEN WEDGE OSTEOTOMY SYSTEM AND SURGICAL METHOD now U.S. Pat. No. 8,083,746;

(iii) is a continuation-in-part of pending prior U.S. patent application Ser. No. 11/352,103, filed Feb. 9, 2006 by Vincent P. Novak et al. for MULTI-PART IMPLANT FOR OPEN WEDGE KNEE OSTEOTOMIES;

(iv) is a continuation-in-part of pending prior U.S. patent application Ser. No. 11/350,333, filed Feb. 8, 2006 by Vincent P. Novak et al. for METHOD AND APPARATUS FOR FORMING A WEDGE-LIKE OPENING IN A BONE FOR AN OPEN WEDGE OSTEOTOMY;

(v) is a continuation-in-part of pending prior U.S. patent application Ser. No. 11/396,490, filed Apr. 3, 2006 by Kelly Ammann et al. for METHOD AND APPARATUS FOR PERFORMING AN OPEN WEDGE, HIGH TIBIAL OSTEOTOMY;

(vi) is a continuation-in-part of prior U.S. patent application Ser. No. 11/607,321, filed Dec. 1, 2006 by Kelly G. Ammann et al. for METHOD AND APPARATUS FOR PERFORMING AN OPEN WEDGE, HIGH TIBIAL OSTEOTOMY now U.S. Pat. No. 7,967,823;

(vii) is a continuation-in-part of prior U.S. patent application Ser. No. 11/644,218, filed Dec. 22, 2006 by Kelly G. Ammann et al. for METHOD AND APPARATUS FOR PERFORMING AN OPEN WEDGE, HIGH TIBIAL OSTEOTOMY now U.S. Pat. No. 7,935,119;

(viii) is a continuation-in-part of pending prior U.S. patent application Ser. No. 11/888,506, filed Aug. 1, 2007 by Kelly G. Ammann et al. for METHOD AND APPARATUS FOR PERFORMING AN OPEN WEDGE, HIGH TIBIAL OSTEOTOMY; and (ix) claims benefit of pending prior U.S. Provisional Patent Application Ser. No. 61/196,852, filed Oct. 21, 2008 by Kelly Ammann et al. for AXIAL KNEE REALIGNMENT (AKR) SYSTEM.

The nine (9) above-identified patent applications are hereby incorporated herein by reference.

FIELD OF THE INVENTION

This invention relates to surgical methods and apparatus in general, and more particularly to surgical methods and apparatus for performing open wedge, high tibial osteotomies of the knee.

BACKGROUND OF THE INVENTION

Osteotomies of the knee are an important technique for treating knee osteoarthritis. In essence, knee osteotomies adjust the geometry of the knee joint so as to transfer weight bearing load from arthritic portions of the joint to relatively unaffected portions of the joint.

Knee osteotomies are also an important technique for addressing abnormal knee geometries, e.g., due to birth defect, injury, etc.

Most knee osteotomies are designed to modify the geometry of the tibia, so as to adjust the manner in which the load is transferred across the knee joint.

There are generally two ways to adjust the geometry of the tibia: (i) the "closed wedge" technique; and (ii) the "open wedge" technique.

With the closed wedge technique, a wedge of bone is removed from the upper portion of the tibia, and then the tibia is manipulated so as to close the resulting gap, whereby to reorient the lower portion of the tibia relative to the tibial plateau and hence adjust the manner in which load is transferred from the femur to the tibia.

With the open wedge technique, a cut is made into the upper portion of the tibia, the tibia is manipulated so as to open a wedge-like opening in the bone, and then the bone is secured in this position (e.g., by screwing metal plates to the bone or by inserting a wedge-shaped implant into the opening in the bone), whereby to reorient the lower portion of the tibia relative to the tibial plateau and hence adjust the manner in which load is transferred from the femur to the tibia.

While both closed wedge osteotomies and open wedge osteotomies provide substantial benefits to the patient, they are procedurally challenging for the surgeon. Among other things, with respect to open wedge osteotomies, it can be difficult to create the wedge-like opening in the bone with the necessary precision and with a minimum of trauma to the surrounding tissue (e.g., the delicate neurological and vascular structures at the back of the knee). Furthermore, with open wedge osteotomies, it can be difficult to stabilize the upper and lower portions of the tibia relative to one another and to maintain the two bone portions in this position while healing occurs.

The present invention is directed to open wedge, high tibial osteotomies of the knee, and is intended to provide increased precision and reduced trauma when creating the wedge-shaped opening in the bone, and to provide increased stability to the upper and lower portions of the tibia while healing occurs.

SUMMARY OF THE INVENTION

The present invention comprises a novel method and apparatus for performing an open wedge, high tibial osteotomy. More particularly, the present invention comprises the provision and use of a novel method and apparatus for forming an appropriate osteotomy cut into the upper portion of the tibia, manipulating the tibia so as to open an appropriate wedge-like opening in the tibia, and then mounting an appropriately-shaped implant in the wedge-like opening in the tibia, so as to stabilize the tibia with the desired orientation, whereby to reorient the lower portion of the tibia relative to the tibial plateau and hence adjust the manner in which load is transferred from the femur to the tibia.

In one form of the present invention, there is provided apparatus for use in performing an open wedge, high tibial osteotomy, the apparatus comprising:

an adjustable base assembly, the adjustable base assembly comprising:
  a base;
  an anterior arm attached to the base;
  a first opening extending through the anterior arm and the base for receiving a frontal fixation pin for pivotally mounting the adjustable base assembly to a tibia;

a hinge pin slider slidably mounted to the anterior arm for selective disposition along the anterior arm, the hinge pin slider including a hinge pin aimer for receiving a hinge pin; and a second opening extending through the base for receiving an antero-medial fixation pin for pinning the base to the tibia.

In another form of the present invention, there is provided a method for performing an open wedge, high tibial osteotomy, the method comprising:

providing:
an adjustable base assembly, the adjustable base assembly comprising:
a base;
an anterior arm attached to the base;
a first opening extending through the anterior arm and the base for receiving a frontal fixation pin for pivotally mounting the adjustable base assembly to a tibia;
a hinge pin slider slidably mounted to the anterior arm for selective disposition along the anterior arm, the hinge pin slider including a hinge pin aimer for receiving a hinge pin; and
a second opening extending through the base for receiving an antero-medial fixation pin for pinning the base to the tibia;
a keyhole drill guide assembly for mounting to the base of the adjustable base assembly, the keyhole drill guide comprising:
at least one keyhole drill guide;
a medial locator tab; and
an antero-medial locator tab;
a biplanar alignment assembly for mounting to the adjustable base assembly, the biplanar alignment assembly comprising a biplanar alignment bar formed at least in part out of a radio-opaque material;
a hinge pin for deployment through the hinge pin aimer and into the tibia;
a cutting guide for mounting to the base of the adjustable base assembly, the cutting guide comprising:
at least one keyhole locating boss; and
a saw guide slot; and
an implant for disposition in the wedge-like opening in the bone;
mounting the keyhole drill guide assembly to the base of the adjustable base assembly and mounting the biplanar alignment assembly to the base of the adjustable base assembly;
positioning the antero-medial locating tab against the medial aspect of the tibia, positioning the medial locating tab against the medial aspect of the tibia and, when viewing from the lateral view, aligning the biplanar alignment bar with the tibial plateau;
pivotally mounting the adjustable base assembly to the tibia with a frontal fixation pin;
rotating the anterior arm of the adjustable base assembly about the frontal fixation pin, and adjusting the position of hinge pin slider on the anterior arm, so as to align the hinge pin aimer with a desired position for the hinge pin;
passing the hinge pin through the hinge pin aimer and into the tibia;
drilling at least one keyhole in the tibia using the keyhole drill guide assembly;
replacing the keyhole drill guide assembly with the cutting guide;
forming a saw cut in the tibia using the cutting guide;
opening the saw cut so as to form a wedge-like opening in the bone; and
inserting the implant into the wedge-like opening in the bone.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 31-33 are schematic views showing a cutting guide;

DETAILED DESCRIPTION OF THE PREFERRED EMBODIMENTS

Overview of an Open Wedge, High Tibial Osteotomy

Figure 1:
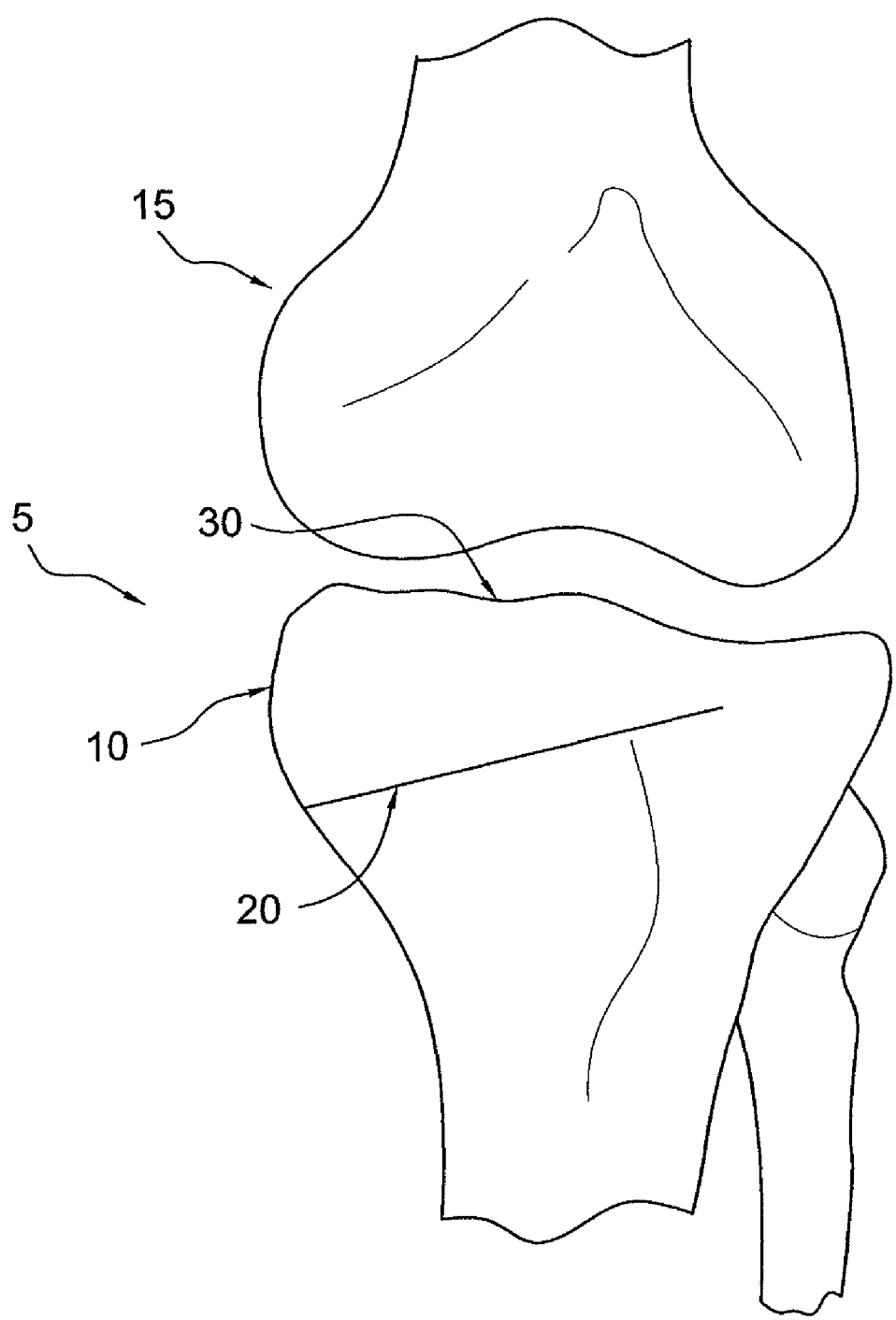
FIGS. 1-3 are schematic views of the left leg from an anterior view showing the formation of a wedge-like opening in the tibia for an open wedge, high tibial osteotomy, and the positioning of a wedge-shaped implant into the wedge-like opening in the tibia.
Figure 2:
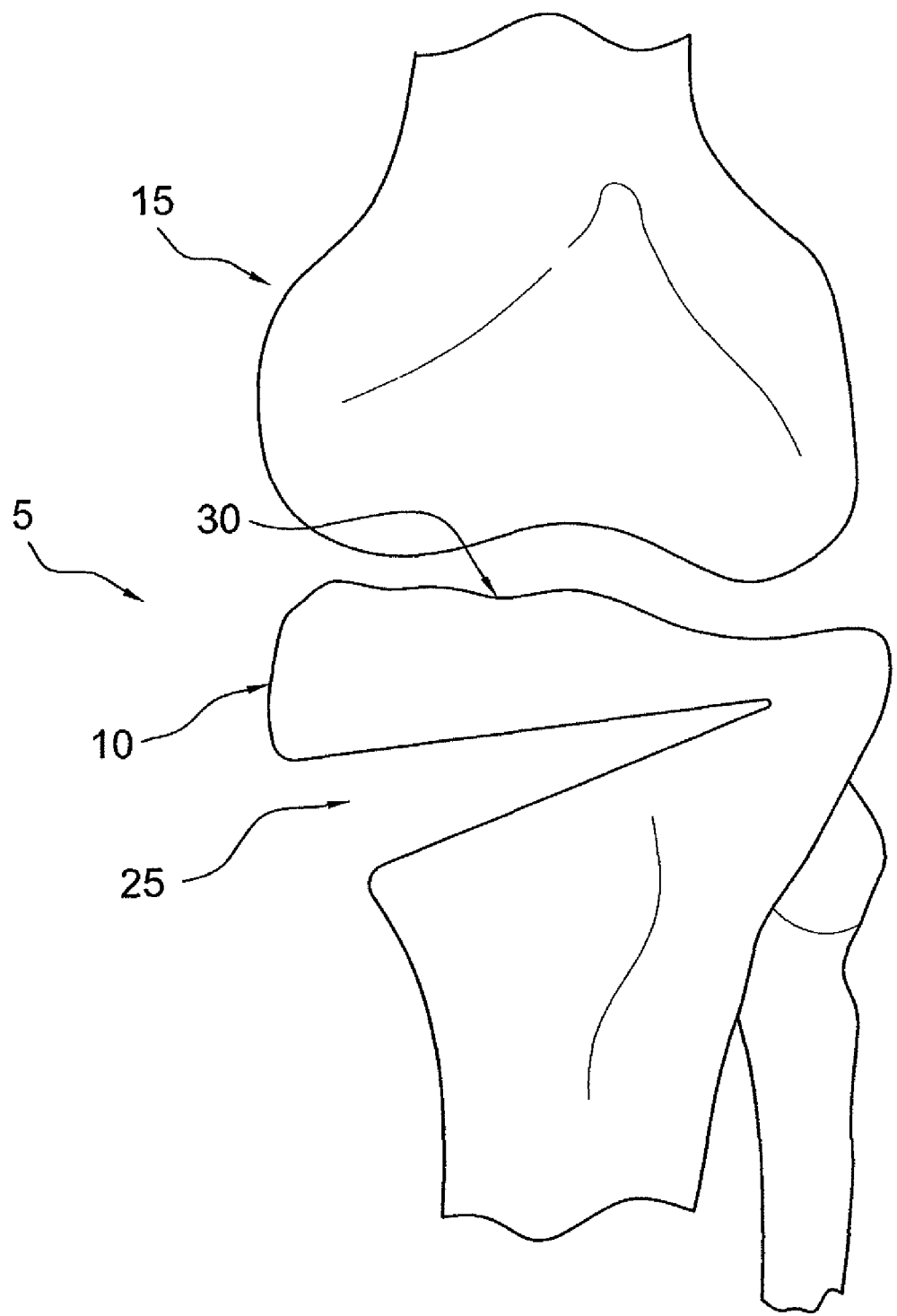
Figure 3:
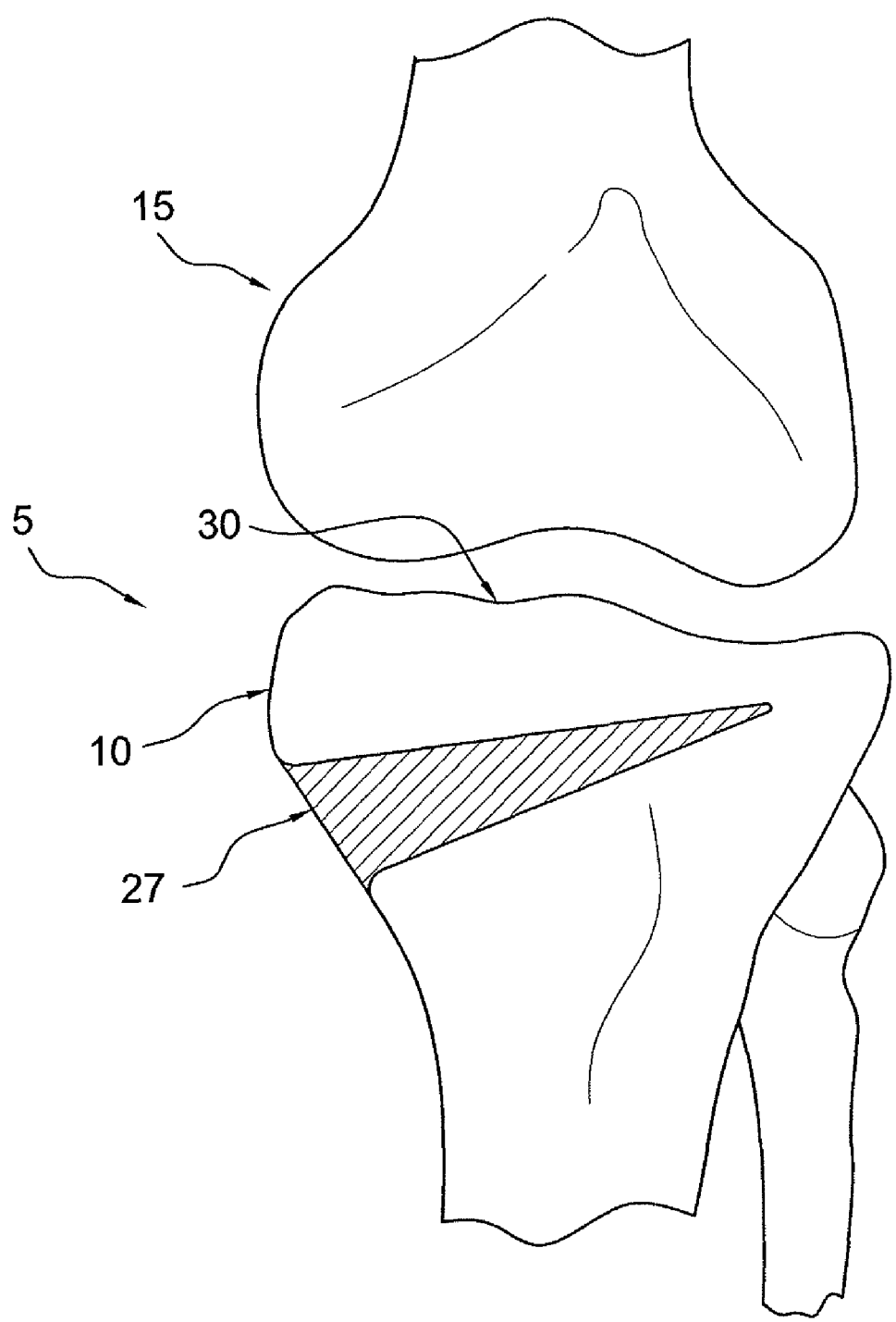

Looking first at FIGS. 1-3, there is shown a knee joint 5 of, for example, the left leg from an anterior view upon which an open wedge osteotomy is to be performed. Knee joint 5 generally comprises a tibia 10 and a femur 15. In accordance with the present invention, the open wedge osteotomy is effected by first making a cut 20 (FIG. 1) into the upper tibia, and then manipulating the lower portion of the tibia so as to open a wedge-like opening 25 (FIG. 2) in the bone, with the wedge-like opening 25 being configured so as to adjust the manner in which load is transferred from the femur to the tibia. In this respect it should be appreciated that a variety of methods are well known in the art for determining the degree of correction necessary to correctly re-align the weight-bearing axis of the knee. Furthermore, cut 20 and wedge-like opening 25 may be formed in a variety of ways well known in the art.

Once the desired wedge-like opening 25 has been formed in tibia 10 so as to reconfigure the tibia to the desired geometry, the bone may be secured in position in a variety of ways well known in the art (e.g., by screwing metal plates to the bone or by inserting a wedge-shaped implant into the opening in the bone), whereby to adjust the manner in which load is transferred from the femur to the tibia. By way of example, FIG. 3 shows a wedge-shaped implant 27 inserted into the wedge-like opening 25 formed in the tibia, whereby to stabilize the tibia in its reconfigured geometry.

Among other things, the present invention provides a new and improved method and apparatus for performing an open wedge, high tibial osteotomy, as will be discussed in detail below.

Figure 3A:
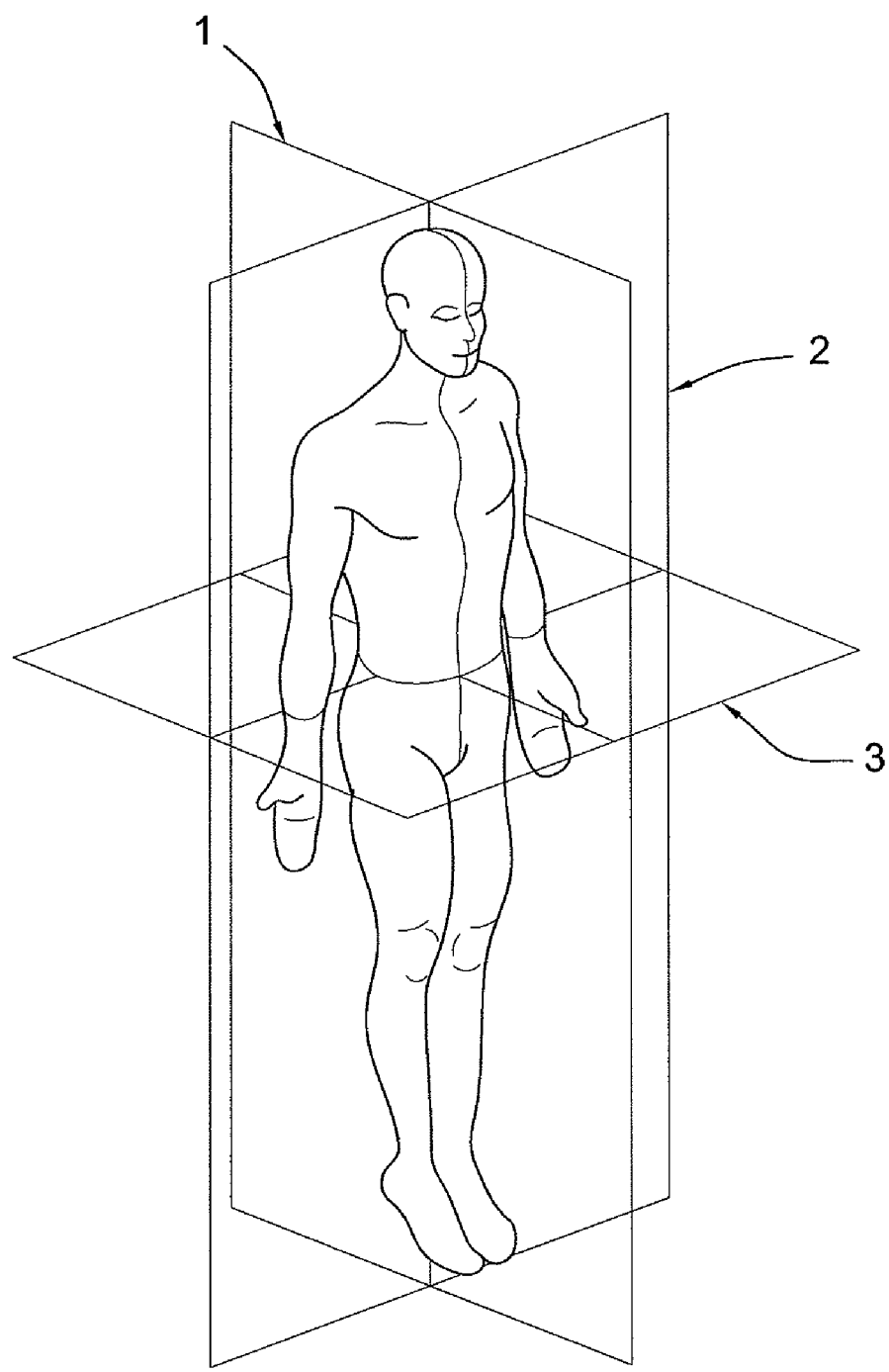
FIG. 3A is a schematic view showing selected anatomical body planes.

Discussion of the Relevant Planar Surfaces in the Open Wedge, High Tibial Osteotomy of the Present Invention In order to appreciate certain aspects of the present invention, it is helpful to have a thorough understanding of the planar surfaces of the tibia that are relevant in performing the open wedge, high tibial osteotomy of the present invention. Thus, the following discussion presents a geometric description of the planar surfaces that are relevant to the open wedge, high tibial osteotomy of the present invention. For the purposes of the present discussion, it can sometimes be helpful to refer to selected anatomical planes, e.g., the sagittal plane 1, the coronal plane 2 (also known as the frontal plane), and the transverse plane 3 (FIG. 3A).

Figure 4:
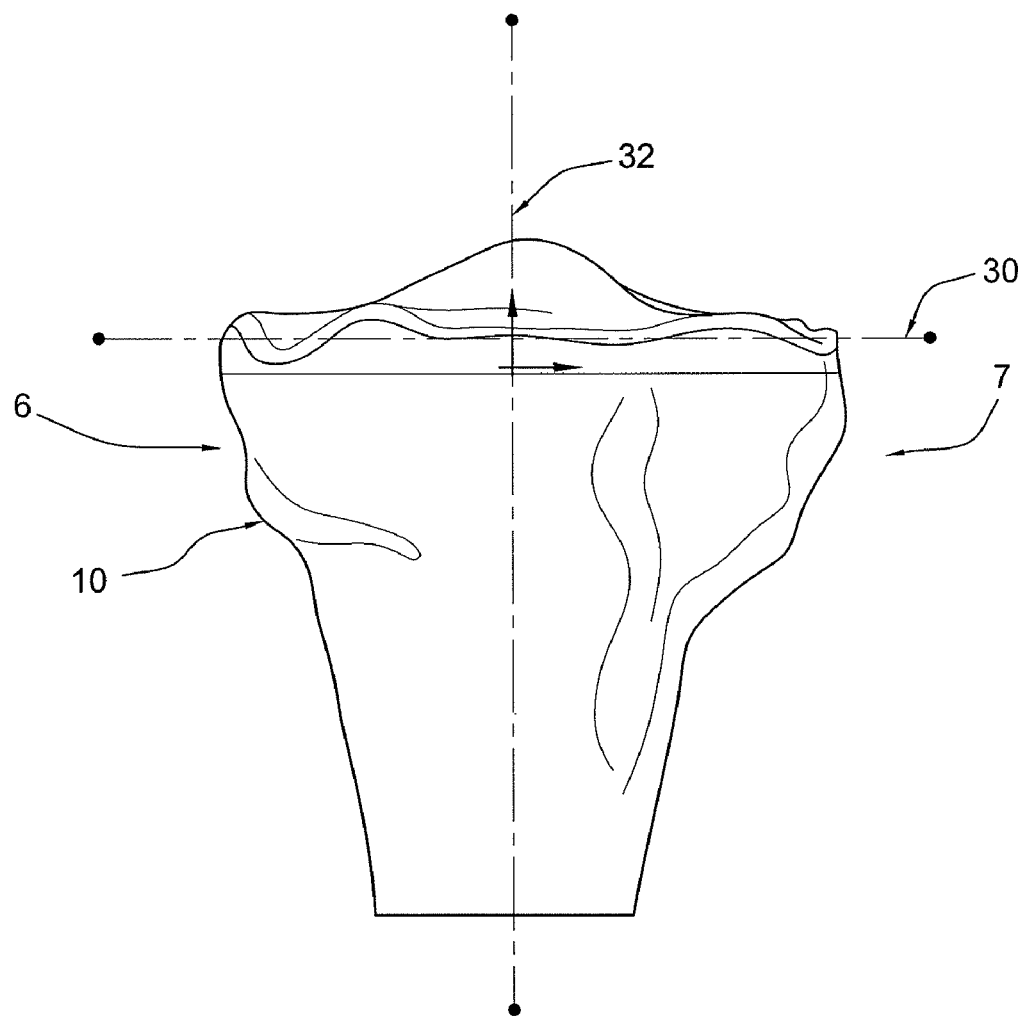
FIGS. 4-9 show the relevant planar surfaces in an open wedge, high tibial osteotomy conducted in accordance with the present invention from the anterior view and the medial view of the left leg.
Figure 5:
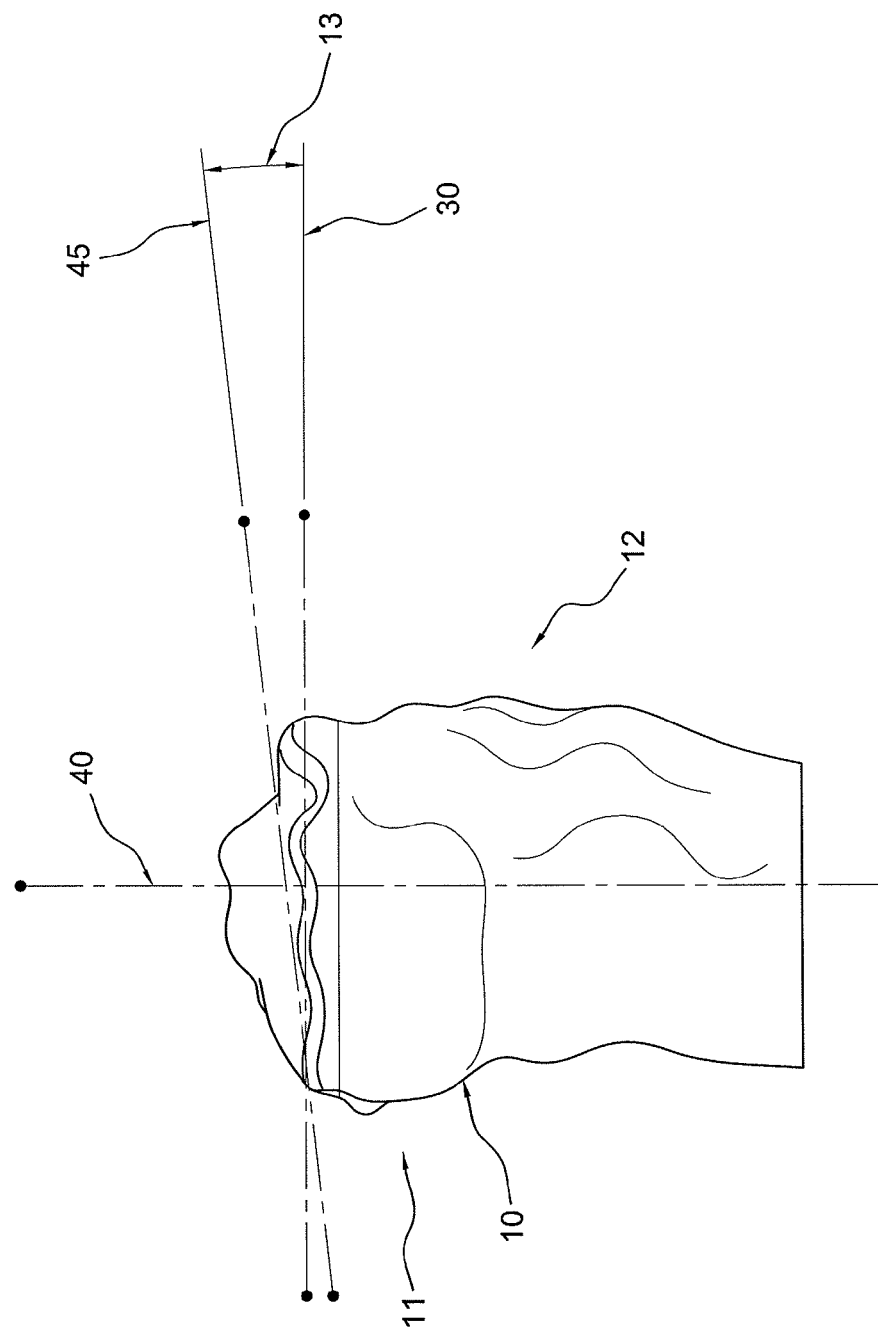

Looking now at FIGS. 1-4, for the purposes of the present invention, the tibial plateau 30 may be described as a horizontal (or transverse) plane that extends along the top surface of tibia 10. For reference and example, FIG. 4 shows the left leg from an anterior view such that the medial side 6 and the lateral side 7 of the tibia 10 can be seen. The sagittal plane 32 is also shown in FIG. 4. As seen in FIG. 5 from the medial view, tibial plateau 30 is also perpendicular to the frontal (or coronal) plane 40. The anterior-posterior (A-P) slope is defined by an anterior-posterior (A-P) slope plane 45 that extends along the sloping top surface of the tibia, from anterior side 12 to posterior side 10. Published research has demonstrated that the anterior-posterior (A-P) slope typically extends at an exemplary angle 13 of approximately 7°-11° to the tibial plateau 30; however, the specific angle may vary from individual to individual.

Figure 6:
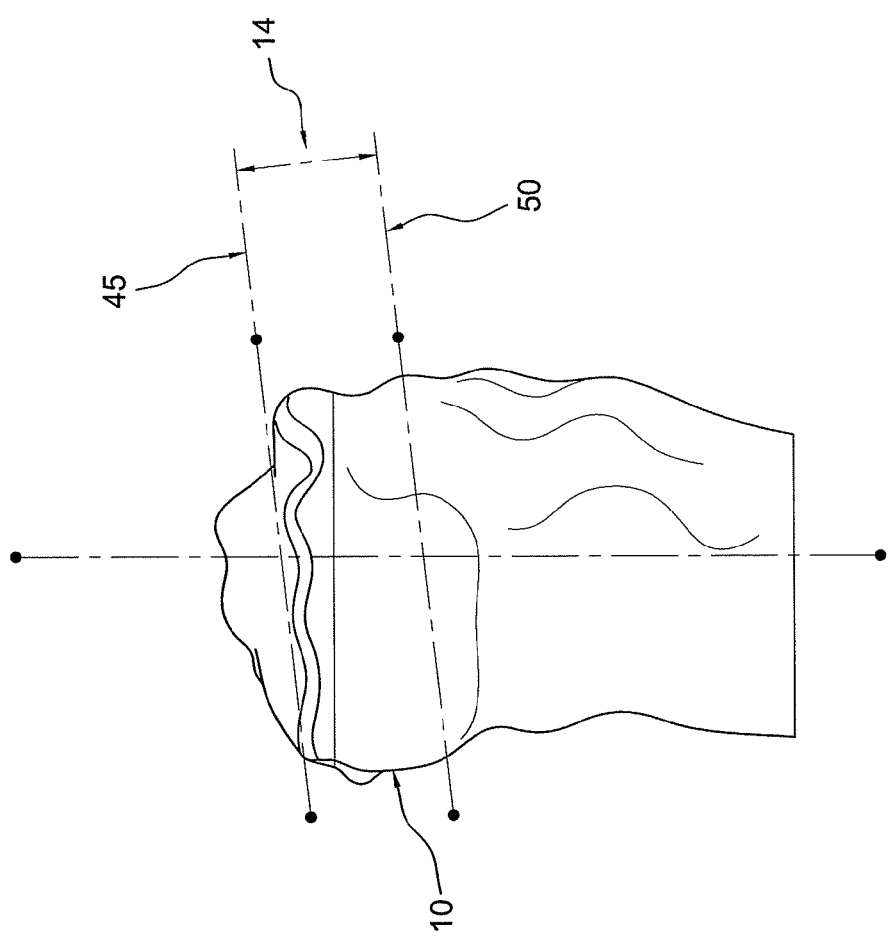

Looking next at FIG. 6, a medial view of the left leg, for the open wedge, high tibial osteotomy of the present invention, it is generally desirable to stay an exemplary distance 14 of about 2 cm inferior to the A-P slope plane 45. This offset can be referred to as the A-P offset plane 50.

Figure 7:
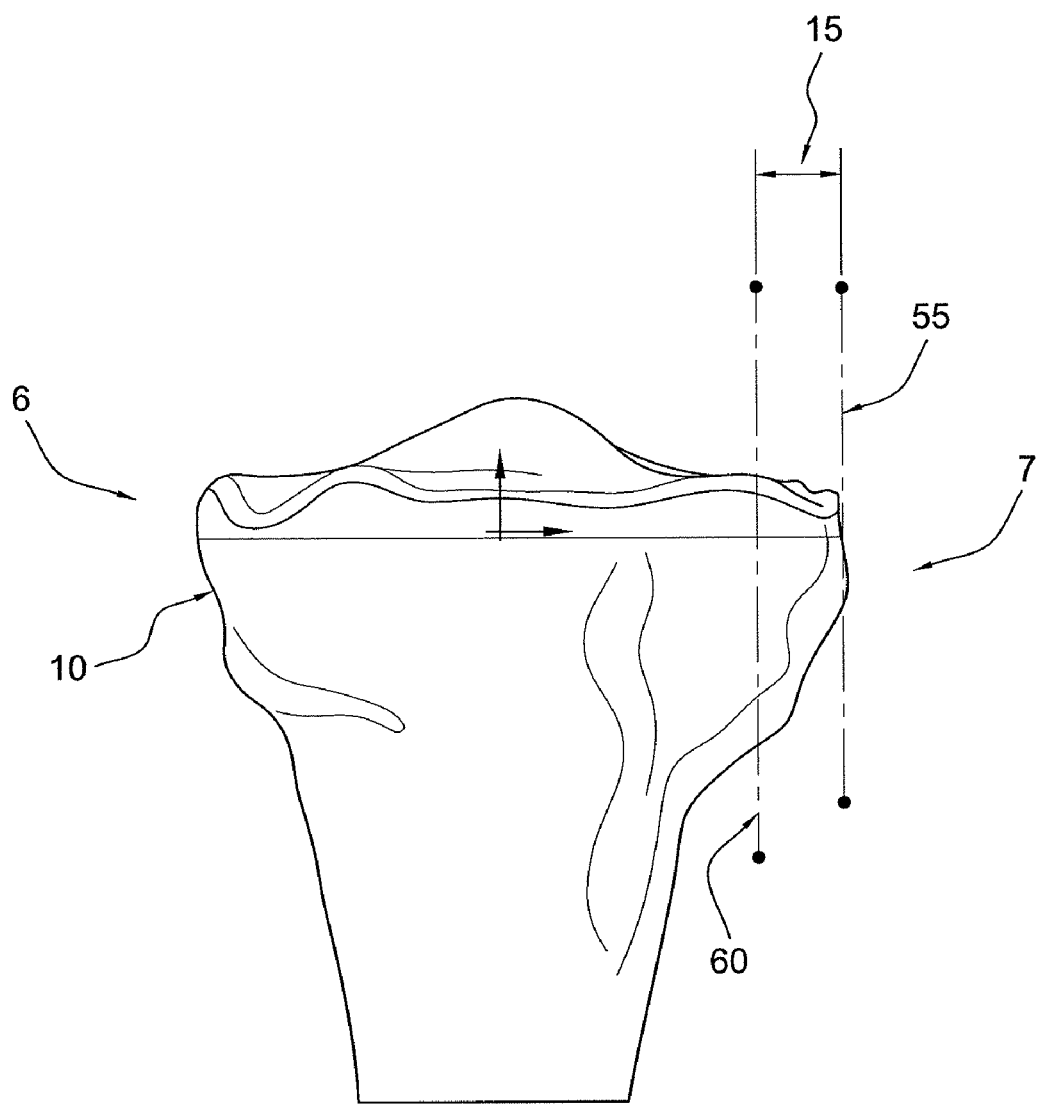

As seen in FIG. 7, an anterior view of the left leg, the lateral aspect and cut depth of cut 20 (FIG. 1) may be defined by a lateral aspect plane 55 and a cut depth plane 60, with the cut depth being an exemplary distance 15 of about 1 cm toward the medial side 6 from the lateral aspect plane 55 of the tibia, located on the lateral side 7 of the tibia.

Figure 8:
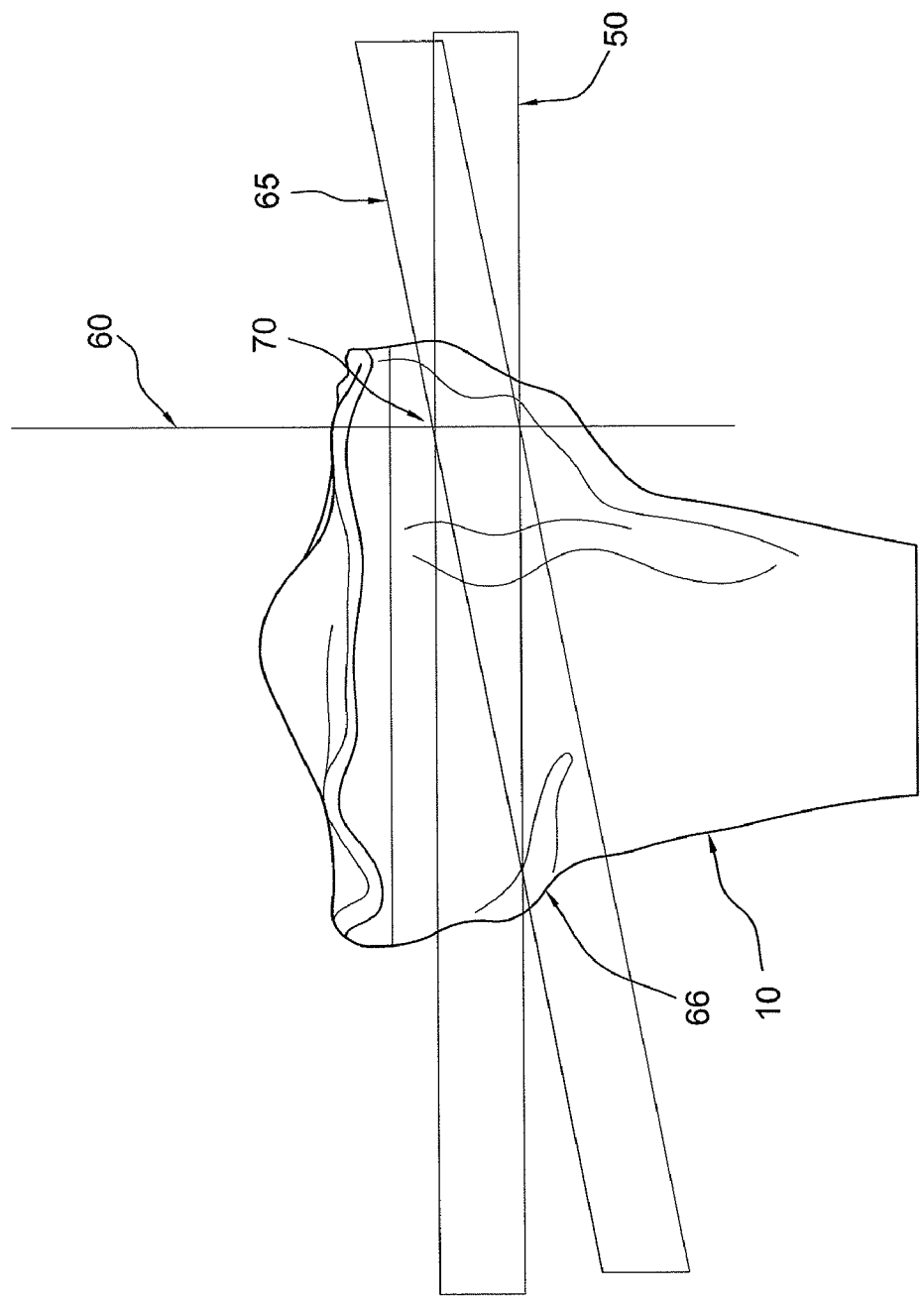

Looking next at FIG. 8, showing the left leg from an anterior view, the osteotomy cut plane 65 (when seen from the direct frontal view of FIG. 8) is formed by a plane that is rotated away from the A-P offset plane 50 through an axis which is formed by the intersection of the cut depth plane 60 and the A-P offset plane 50. The degree of rotation is selected so as to be sufficient to place the entry of the osteotomy cut plane 65 at the medial neck 66 (FIG. 8) of the tibia. It should be noted that the A-P offset plane 50 and the osteotomy cut plane 65 are "tilted" slightly, from anterior to posterior (but not seen in the direct frontal view of FIG. 8), since the A-P offset plane 50 and the osteotomy cut plane 65 follow the tilt of the A-P slope plane 45 (FIG. 6). The intersection of the A-P offset plane 50 and the cut depth plane 60 forms an axis 70 which, in accordance with the present invention, defines the lateral limit of osteotomy cut 20. In other words, axis 70 defines a line through the tibia which is (i) parallel to A-P slope plane 45, and (ii) contained within osteotomy cut plane 65. Furthermore, in accordance with the present invention, axis 70 is used to define the lateral limit of the osteotomy cut 20 which is to be made into the tibia.

Figure 9:
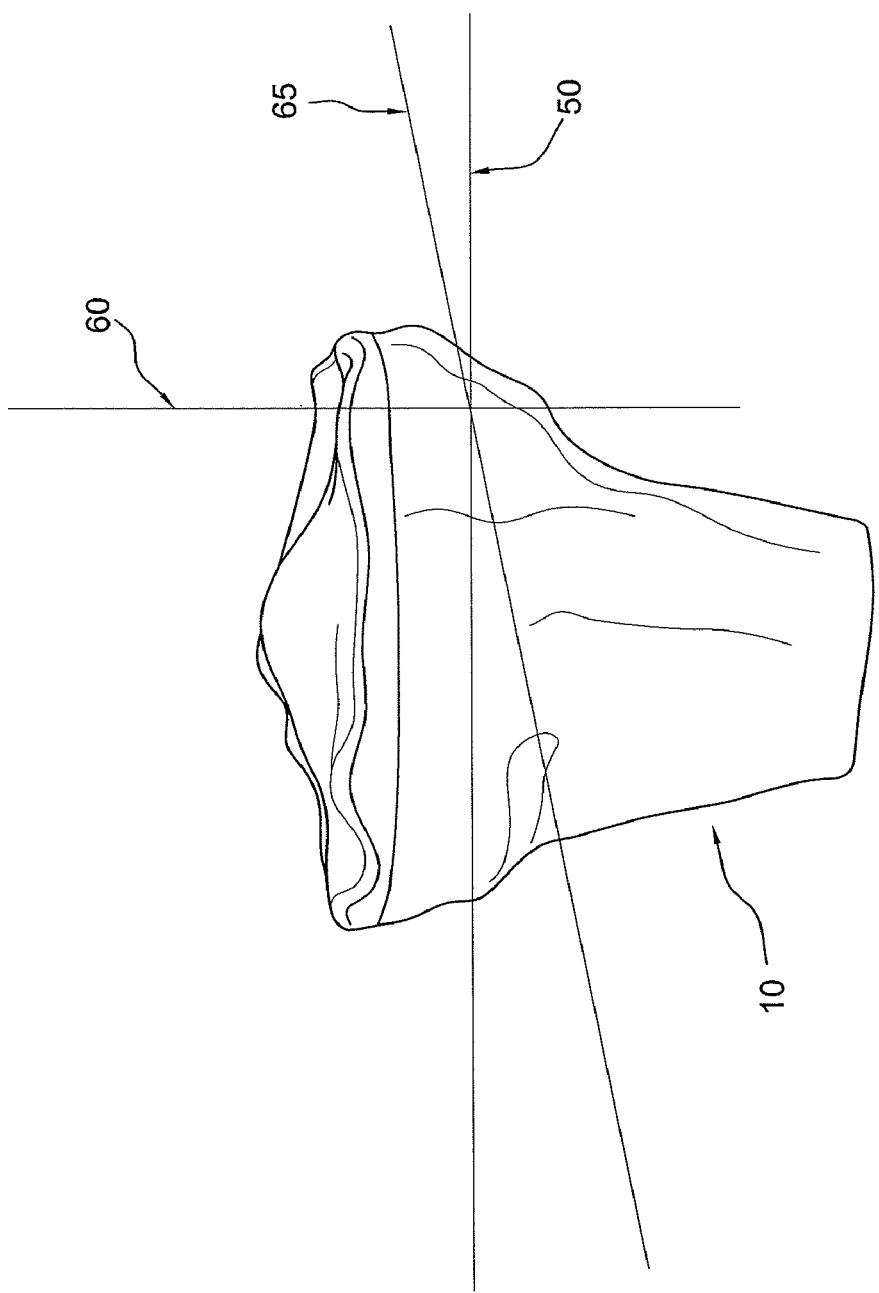

FIG. 9 is a direct view taken along the osteotomy cut plane, showing the left leg from an anterior view tilted slightly superior. This view is tilted downward (e.g., at an angle of approximately 7°) from the direct frontal view of FIG. 8. Again, the angle of tilt downward is equal to the A-P slope. In other words, with the present invention, the osteotomy cut plane 65 extends parallel to the A-P slope plane 45 (in the anterior-to-posterior direction, although not in the medial-to-lateral direction), and typically slopes downward (e.g., at an angle of approximately 7°-11°) when viewed in the anterior-to-posterior direction. Furthermore, with the present invention, the axis 70 (which defines the lateral limit to the osteotomy cut 20) is contained within the osteotomy cut plane 65.

Novel Method and Apparatus for Performing an Open Wedge, High Tibial Osteotomy

In one preferred form of the present invention, there is provided a novel osteotomy system which comprises instrumentation for use in making precise and repeatable osteotomy cuts for use in open wedge, high tibial osteotomies, preferably using an antero-medial approach, and a new and improved implant for deployment in the wedge-shaped opening in the tibia.

Figure 20:
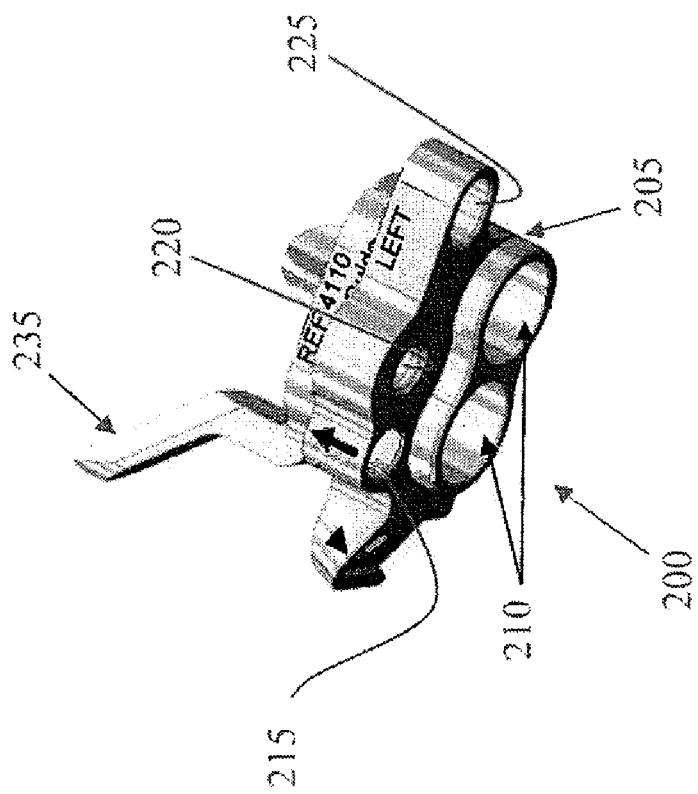
Figure 22:
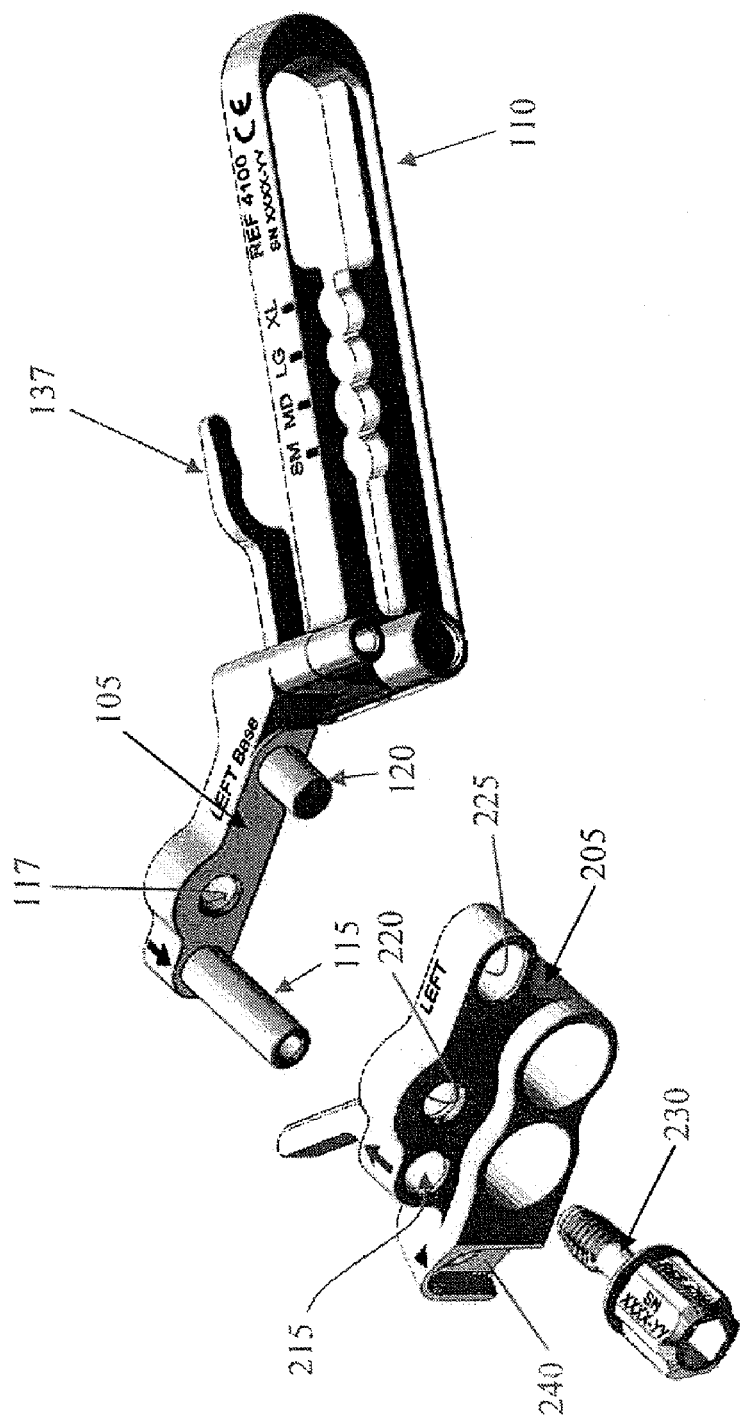
Figure 24:
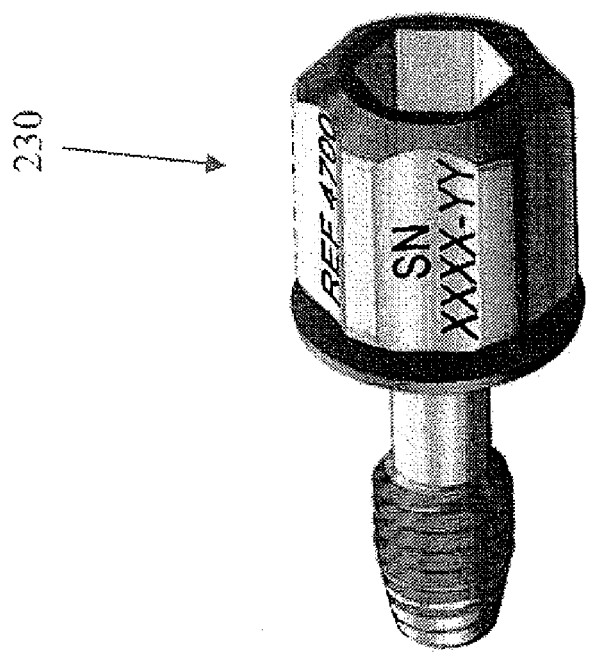
Figure 23:
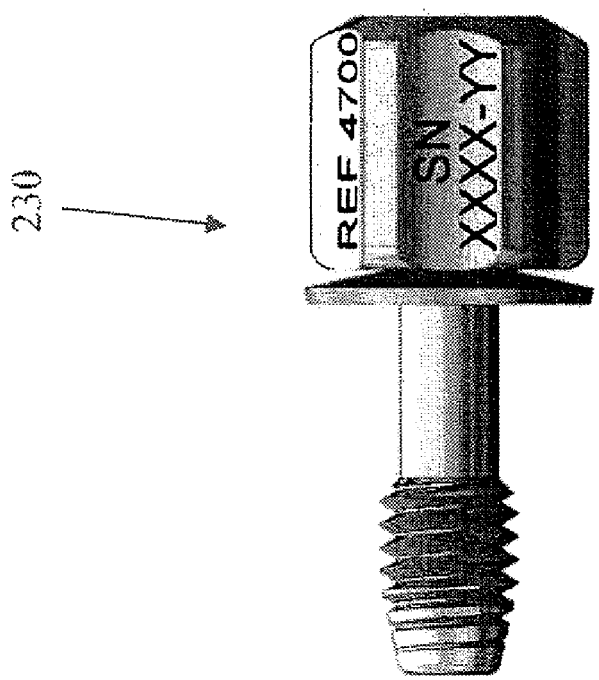
Figure 25:
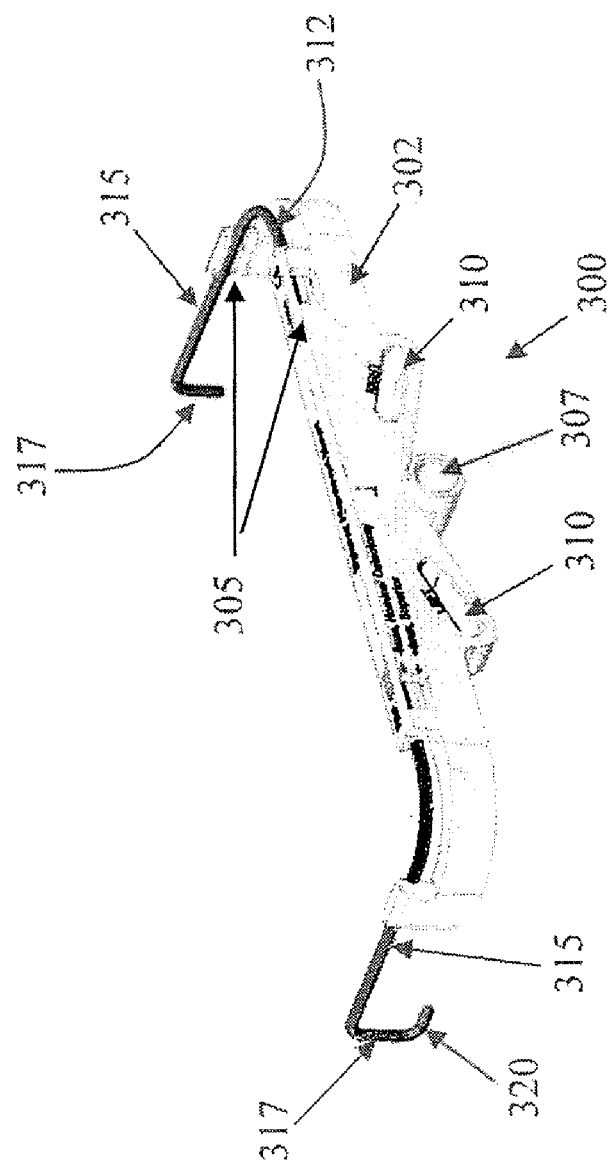
FIGS. 25-27 are schematic views showing further details of the biplanar alignment assembly shown in FIG. 10.
Figure 49:
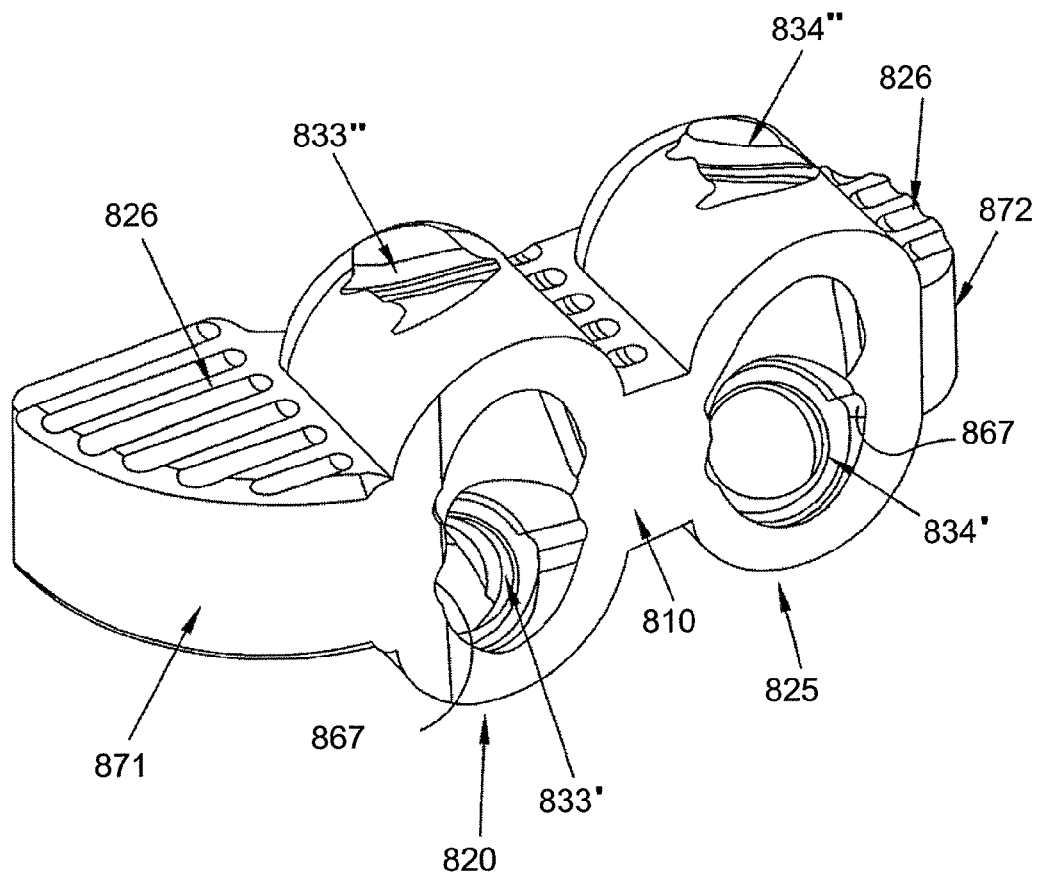
FIGS. 49-54 are schematic views showing an implant.
Figure 50:
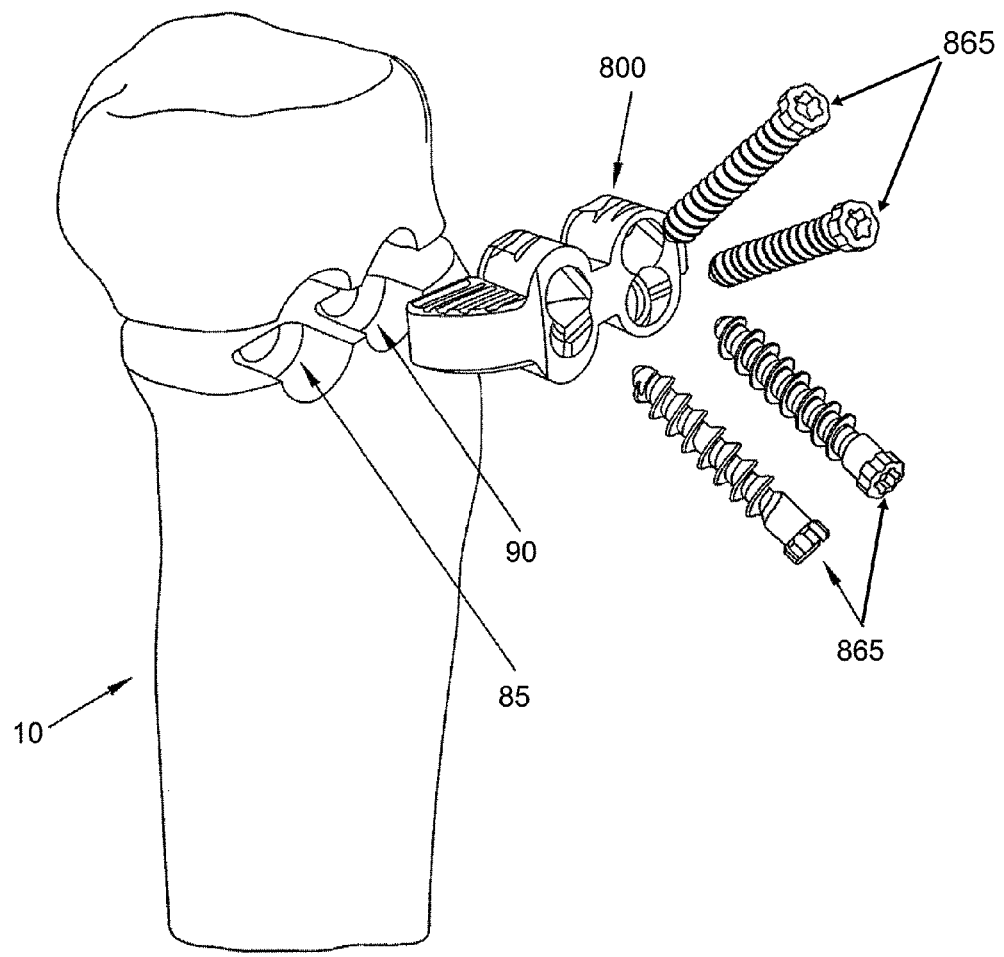

The novel osteotomy system generally comprises an adjustable base assembly 100 (FIGS. 10 and 11), a keyhole drill guide 200 (FIGS. 10 and 20), a biplanar alignment assembly 300 (FIGS. 10 and 25), a hinge pin 400 (FIG. 30), a cutting guide 500 (FIG. 31), a neurovascular shield assembly 600 (FIG. 37), an opening jack assembly 700 (FIG. 44) and an implant 800 (FIG. 49).

Adjustable Base Assembly 100

Adjustable base assembly 100 is shown in detail in FIGS. 10-19. Adjustable base assembly 100 is provided in left and right versions (the left version is shown in FIGS. 10-19), with one size of the adjustable base assembly being capable of accommodating all different sizes of tibias. Adjustable base assembly 100 generally comprises a base 105 having an anterior arm 110 extending therefrom. Base 105 comprises an antero-medial fixation pin boss 115 for receiving an antero-medial fixation pin as will hereinafter be discussed in further detail, a mount hole 117 for use in mounting keyhole drill guide 200 and/or cutting guide 500 to base 105 as will hereinafter be discussed in further detail, and a mounting boss 120 also for use in mounting keyhole drill guide 200 and/or cutting guide 500 to base 105 as will also hereinafter be discussed in further detail.

Anterior arm 110 comprises a slider guide channel 122 (FIG. 12), including a slider guide slot 125 and hinge pin interlock apertures 127, for receiving hinge pin slider 133 (FIG. 11) as will hereinafter be discussed. Anterior arm 110 also includes size markings 134 which will also hereinafter be discussed. Anterior arm 110 also includes a mount 135 for receiving patellar tendon protector 137 (FIG. 11) as will hereinafter be discussed, and a frontal fixation pin boss 140 for receiving a frontal fixation pin, as will hereinafter be discussed.

Figure 11:
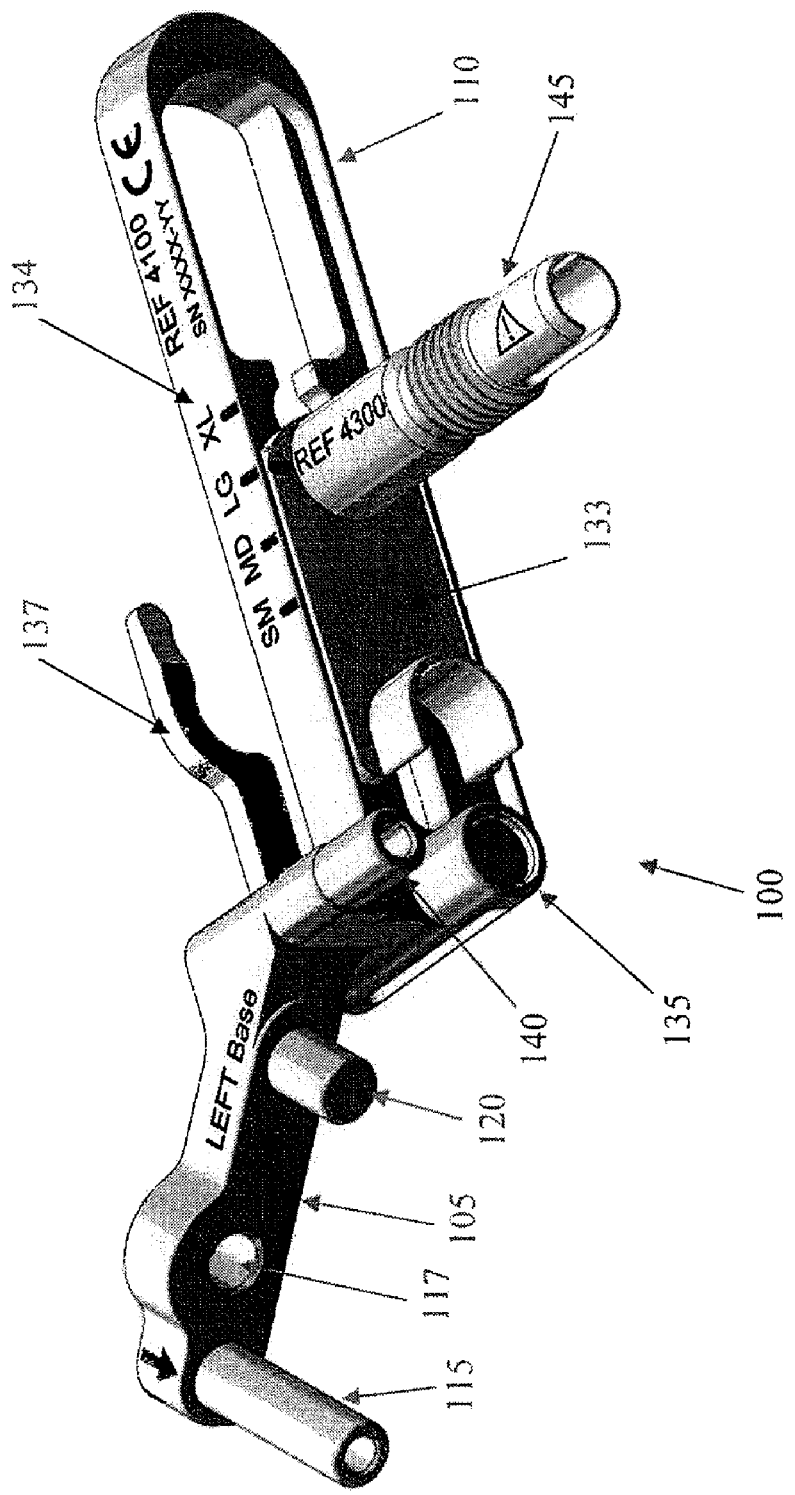
FIGS. 11-19 are schematic views showing further details of the adjustable base assembly shown in FIG. 10.
Figure 12:
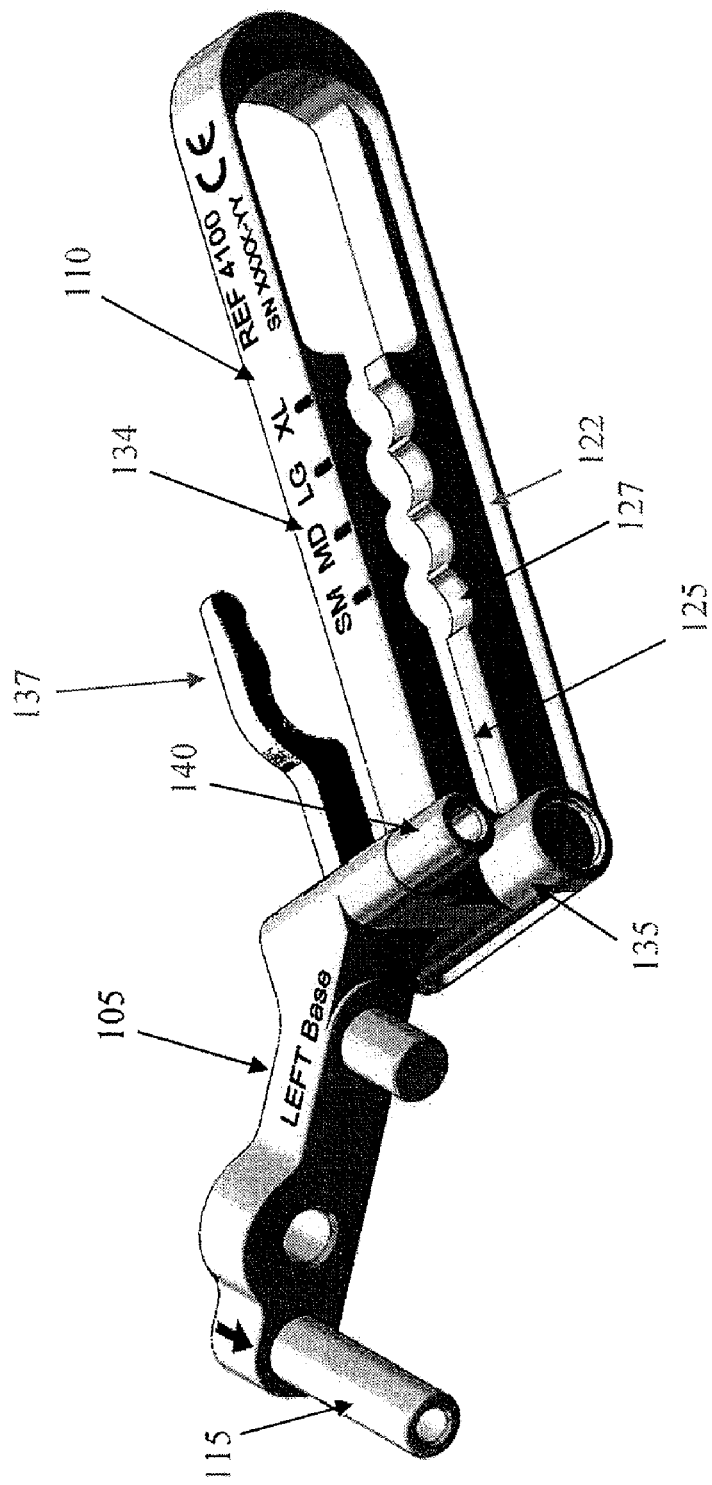
Figure 13:
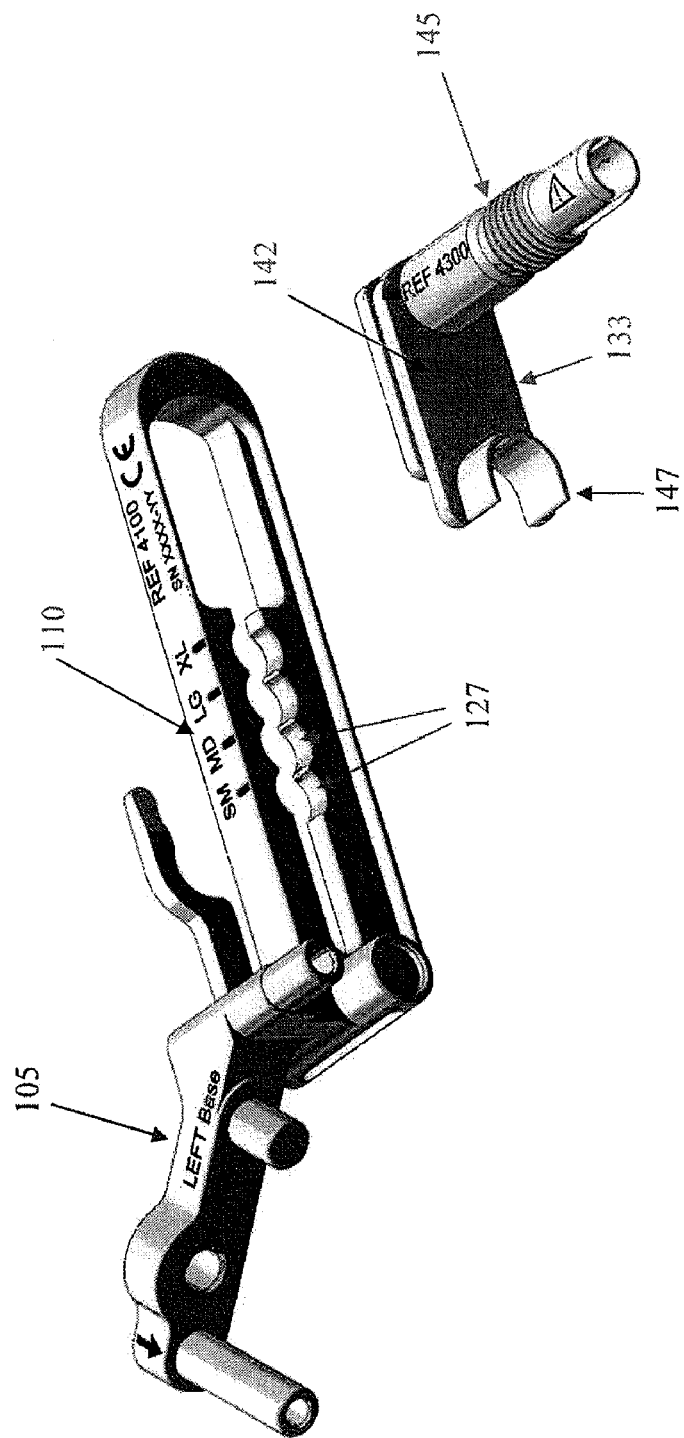
Figure 14:
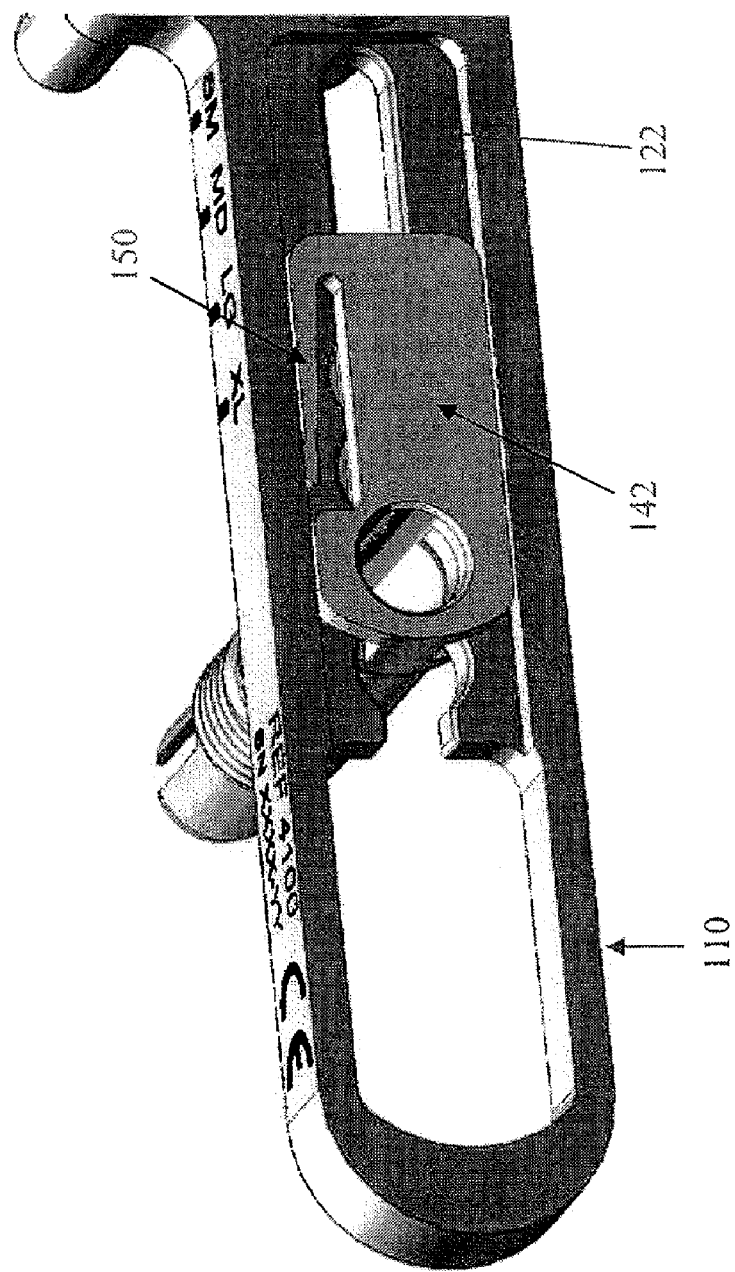
Figure 16:
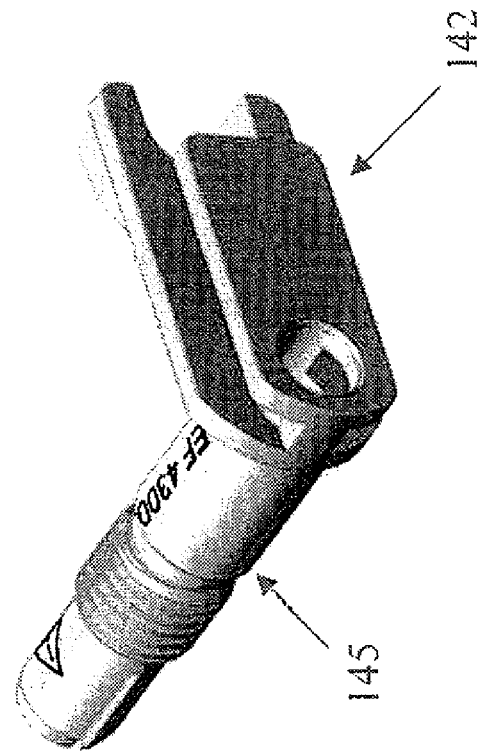
Figure 15:
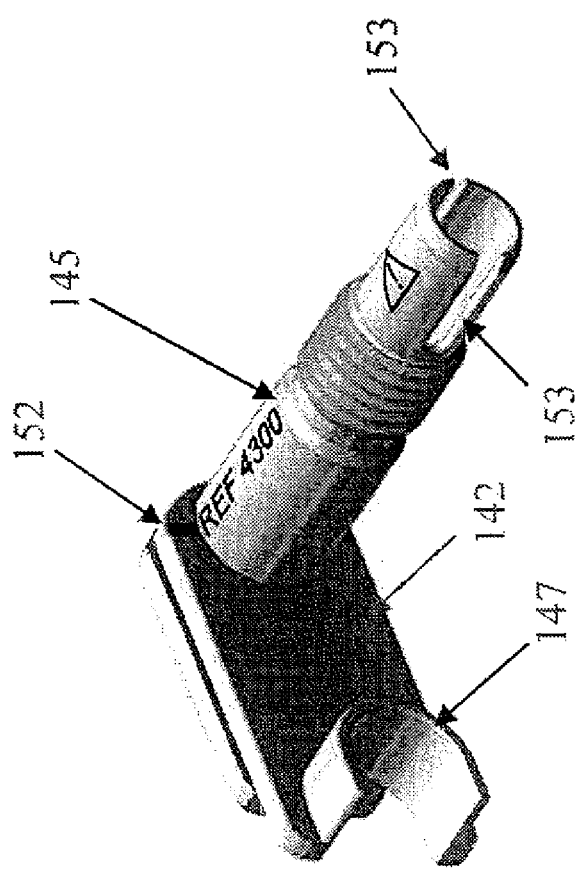
Figure 17:
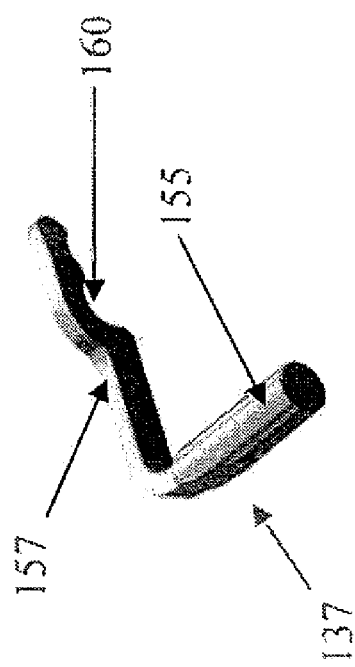

Hinge pin slider 133 comprises a body 142 (FIG. 13) for slidable disposition in slider guide channel 122 (FIGS. 11 and 12). Body 142 carries a hinge pin aimer 145 and a slider safety interlock 147. Hinge pin aimer 145 rides in slider guide slot 125 (FIG. 11) so that hinge pin aimer 145 can be aligned with any one of hinge pin interlock apertures 127. Slider safety interlock 147 engages mount 135 (FIG. 11) on anterior arm 110 so as to limit medial movement of hinge pin slider 133 along anterior arm 110. Hinge pin slider 133 is designed to assemble with either the left or right versions of base 105. A bias spring 150 (FIG. 14) is preferably mounted to body 142 for releasably maintaining body 142 of hinge pin slider 133 in position within slider guide channel 122. More particularly, bias spring 150 provides a controllable amount of friction between hinge pin slider 133 and anterior arm 110 so as to help hinge pin slider 133 stay in position within slider guide channel 122 of anterior arm 110. A size index mark 152 (FIG. 15) is disposed on body 142 for appropriate alignment with size markings 134 (FIG. 11) on anterior arm 110. One or more slots 153 (FIG. 15) are formed on the free end of hinge pin aimer 145 for selective engagement with portions of hinge pin 400, as will hereinafter be discussed.

Figure 19:
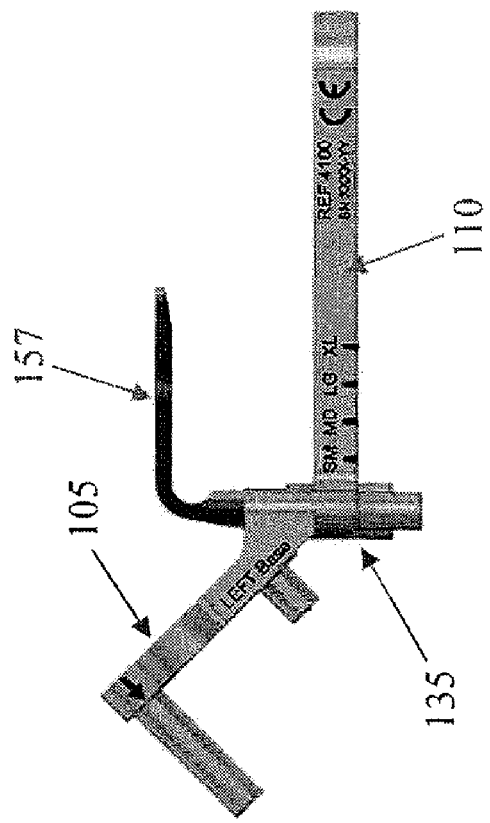
Figure 18:
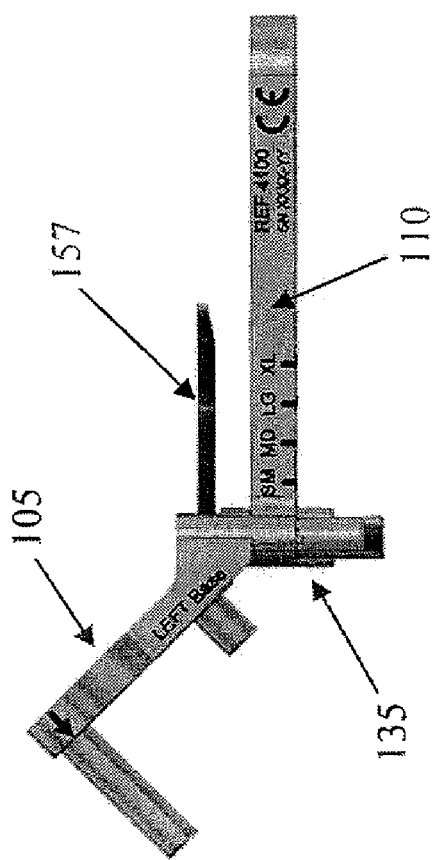
Figure 21:
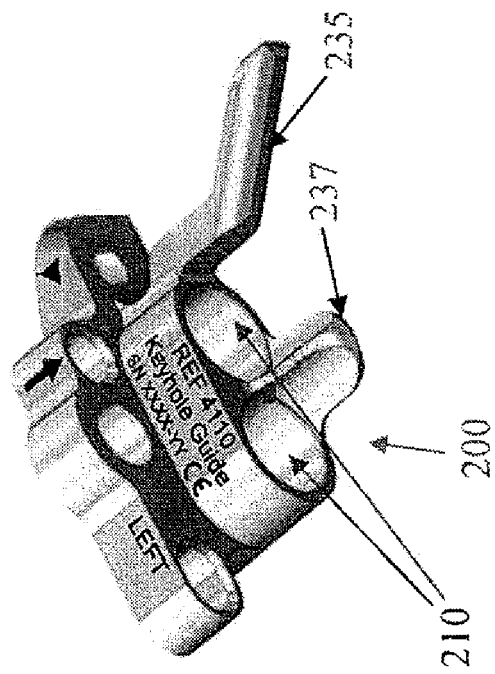
FIGS. 20-24 are schematic views showing further details of the keyhole drill guide shown in FIG. 10.

Patellar tendon protector 137 (FIGS. 11 and 17) itself comprises a guide rod 155 for receipt in mount 135 (FIG. 12) of anterior arm 110, and a patellar tendon protector blade 157 including hinge pin clearance notches 160. Significantly, and as seen in FIGS. 18 and 19, the disposition of patellar tendon protector blade 157 relative to anterior arm 110 can be adjusted so as to accommodate a variety of tubercle heights and the entire range of tibial sizes.

It should be appreciated that the combination of base 105 and anterior arm 110 requires a version for the left knee and a version for the right knee; patellar tendon protector 137 also requires a version for the left knee and another version for the right knee; however, hinge pin slider 133 can use the same design for both the left and the right knee.

Thus it will be seen that adjustable base assembly 100 is a multi-position adjustable construction which can accommodate a range of different size tibias. The embodiment shown in the figures incorporates four discrete positions, i.e., small (SM), medium (MD), large (LG) and extra large (XL), each aligned, respectively, with different hinge pin interlock apertures 127, however, the invention could also consist of any other number of positions (e.g., two or more).

If desired, the end of bias spring 150 can be aligned with hinge pin interlock apertures 127 in anterior arm 110 in order to provide tactile feedback to the surgeon when hinge pin slider 133 is moved along anterior arm 110.

Or, if desired, adjustable base assembly 100 could incorporate a continuous adjustment mechanism rather than the stepped adjustment mechanism discussed above. In this case, slider guide slot 125 could have a smooth surface profile rather than the detent surface profile which forms hinge pin interlock apertures 127.

Keyhole Drill Guide 200

Looking next at FIGS. 10 and 20-24, keyhole drill guide 200 is provided in left and right versions (the left version is shown in FIGS. 10 and 20-24), with one size of keyhole drill guide being capable of accommodating all different sizes of tibias. Keyhole drill guide 200 generally comprises a body 205 having a pair of keyhole drill guides 210 extending therethrough. Keyhole drill guides 210 are used to form keyholes in the tibia, as will hereinafter be discussed in further detail. Keyhole drill guide 200 also comprises mount holes 215, 220 and 225 for mounting keyhole drill guide 200 to base 105, i.e., with mount hole 215 receiving antero-medial fixation pin boss 115, mount hole 220 aligning with mount hole 117, and mount hole 225 receiving mounting boss 120. A threaded fastener 230 (FIGS. 22-24) extends through mount hole 220 and into mount hole 117, whereby to releasably secure keyhole drill guide 200 to base 105.

Keyhole drill guide 200 also comprises a medial locator tab 235, an antero-medial locator tab 237, and a handle mounting channel 240 (which will hereinafter be discussed in further detail). By providing medial locator tab 235 and antero-medial locator tab 237 integral with keyhole drill guide 200, the elements required for properly locating the osteotomy vis-a-vis the tibia are provided, but these same elements are thereafter removed with keyhole drill guide 200, thereby leaving more space available for cutting guide 500 (which is subsequently attached to base 105 as will hereinafter be discussed) and for easier insertion of neurovascular shield assembly 600.

Biplanar Alignment Assembly 300

Looking now at FIGS. 10 and 25-27, biplanar alignment assembly 300 may be used for both the left and right knees, with one size of biplanar alignment assembly being capable of accommodating all different sizes of tibias. Biplanar alignment assembly 300 generally comprises a biplanar alignment mount 302 and a biplanar alignment bar 305. Biplanar alignment mount 302 is preferably formed out of a radio-translucent material (e.g., plastic) and biplanar alignment bar 305 is preferably formed out of a radio-opaque material (e.g., stainless steel), whereby the biplanar alignment bar 305 is visible under fluoroscopy and biplanar alignment mount 302 is effectively invisible under fluoroscopy, as will hereinafter be discussed.

Mount 302 comprises a hinge pin aimer hole 307 and a pair of frontal fixation pin boss apertures (left and right) 310. Biplanar alignment bar 305 comprises a front section 312, a pair of side sections 315 and a pair of vertical sections 317. One of the vertical sections 317 includes a return section 320. Return section 320 provides a unique geometry to one of the two ends of the alignment bar, thereby allowing a surgeon to differentiate between the two ends of biplanar alignment bar 305 under fluoroscopy.

Figure 27:
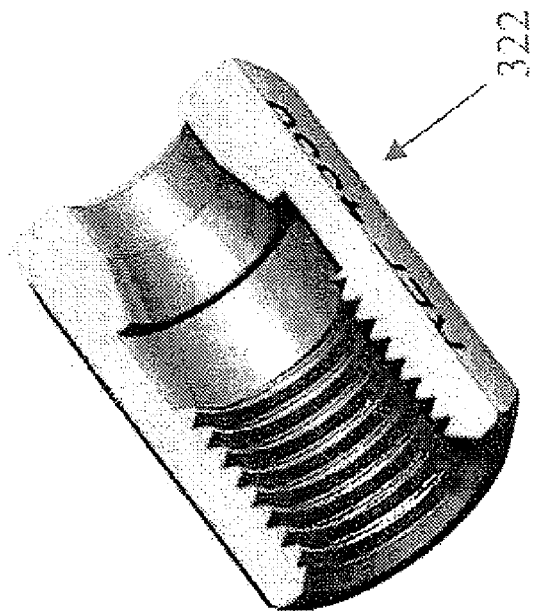
Figure 26:
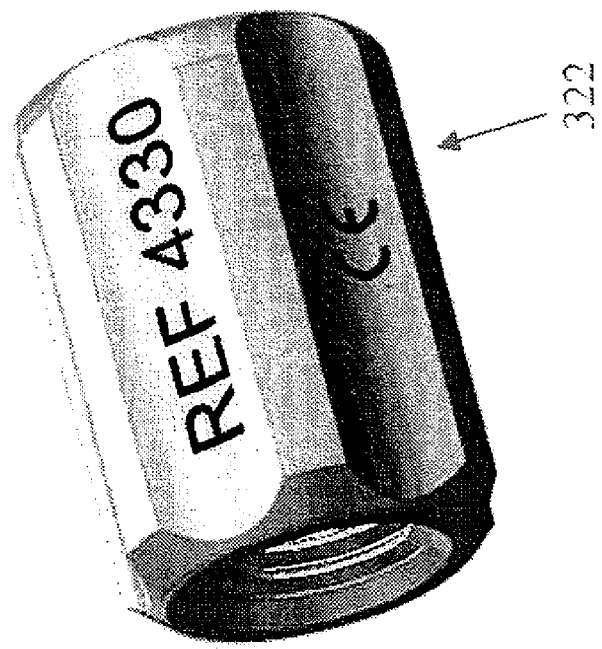

Biplanar alignment assembly 300 is adapted to be assembled onto adjustable base assembly 100 by mounting hinge pin aimer hole 307 over hinge pin aimer 145, and then locking biplanar alignment assembly 300 in place via a collet nut 322 (FIGS. 26 and 27). Collet nut 322 is cannulated as shown, in order that hinge pin 400 may pass through collet nut 322 when the collet nut is mounted on hinge pin aimer 145, as will hereinafter be discussed in further detail.

Significantly, biplanar alignment assembly 300 is left-right compatible, so that only one version of the biplanar alignment guide needs to be provided, regardless of whether one is working on the left knee or the right knee. In other words, the same biplanar alignment assembly 300 works equally well with either the left knee and the right knee, so it is not necessary to provide left and right versions for biplanar alignment assembly 300.

Figure 28:
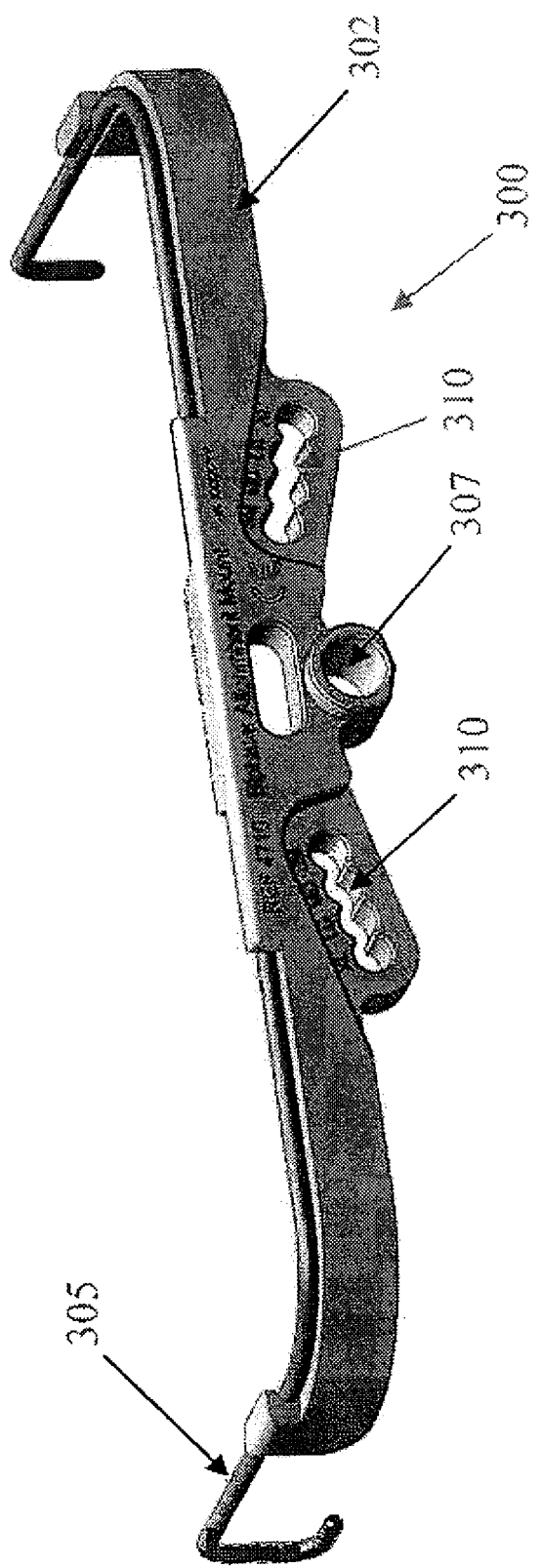
FIGS. 28 and 29 show an alternative form of biplanar alignment assembly also formed in accordance with the present invention.
Figure 29:
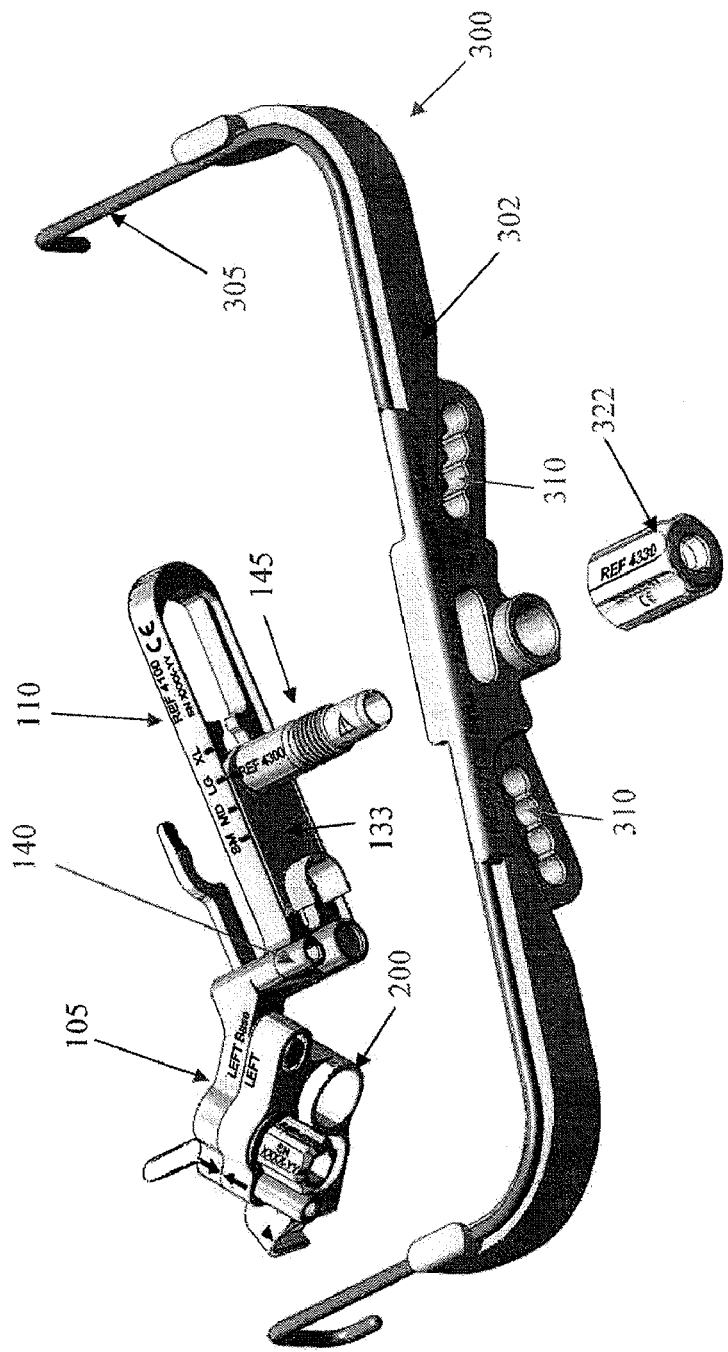

In an alternative form of the invention, and looking now at FIGS. 28 and 29, biplanar alignment assembly 300 may have its frontal fixation pin boss apertures (left and right) 310 formed as a series of detents which coordinate with the small (SM), medium (MD), large (LG) and extra large (XL) positions of hinge pin slider 133 so as to properly align frontal fixation pin boss apertures 310 (FIG. 28) with frontal fixation pin boss 140 (FIG. 29). This provides a means for fixing (or making immovable) the selected size when the tissue protector is inserted and the hinge pin is subsequently inserted into place.

Hinge Pin 400

Figure 30:
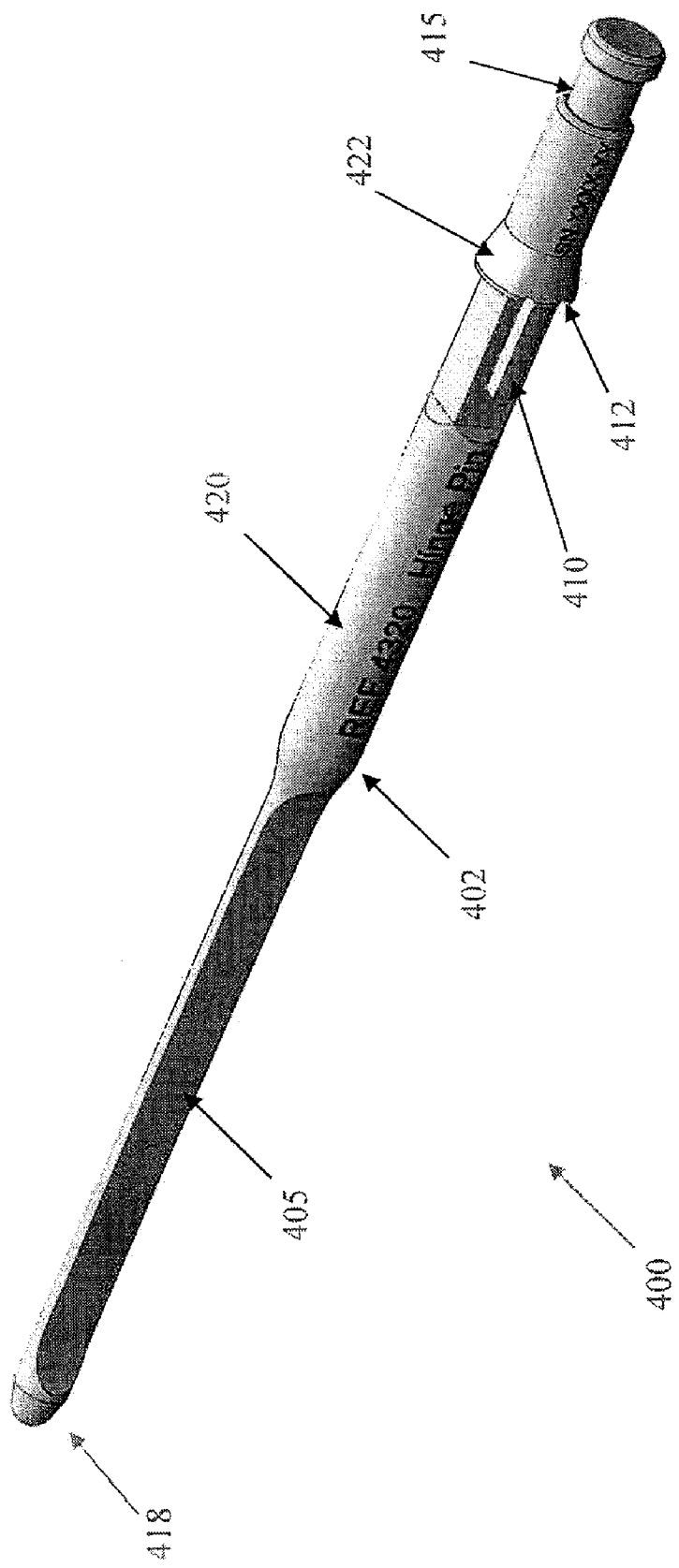
FIG. 30 is a schematic view showing a hinge pin.

Looking next at FIG. 30, hinge pin 400 may be used for both the left and right knees, with one size of hinge pin being capable of accommodating all different sizes of tibias, although different lengths of hinge pin may be provided if desired. Hinge pin 400 comprises a shaft 402. Near its distal end, shaft 402 is provided with a single flat 405 or, alternatively, a pair of diametrically-opposed flats 405 (only one of which is shown in FIG. 30). Near its proximal end, shaft 402 comprises an alignment tab 410 for mating with a slot 153 formed on hinge pin aimer 145 (FIG. 15), whereby to ensure proper alignment of a flat 405 with an advancing saw blade during formation of the osteotomy, as will hereinafter be discussed in further detail. The proximal end of shaft 402 also includes a stop 412 for limiting forward motion of hinge pin 400 into the tibia, and a pin puller notch 415 to facilitate removal of hinge pin 400 from the tibia.

In one preferred form of the invention, shaft 402 of hinge pin 400 has two diameters; a smaller diameter 418 is provided on the distal portion of shaft 402, for easy insertion into the hinge pin hole which is created in the tibia (see below), and a larger diameter 420 is provided on the proximal portion of shaft 402 for a mating interface with the bore of hinge pin aimer 145 (FIG. 15) and with one of the slider interlock apertures 127 (FIG. 12). Preferably shaft 402 also includes a tapered surface 422 immediately proximal to stop 412, for interfacing with collet nut 322 (FIGS. 26 and 27).

Cutting Guide 500

Figure 33:
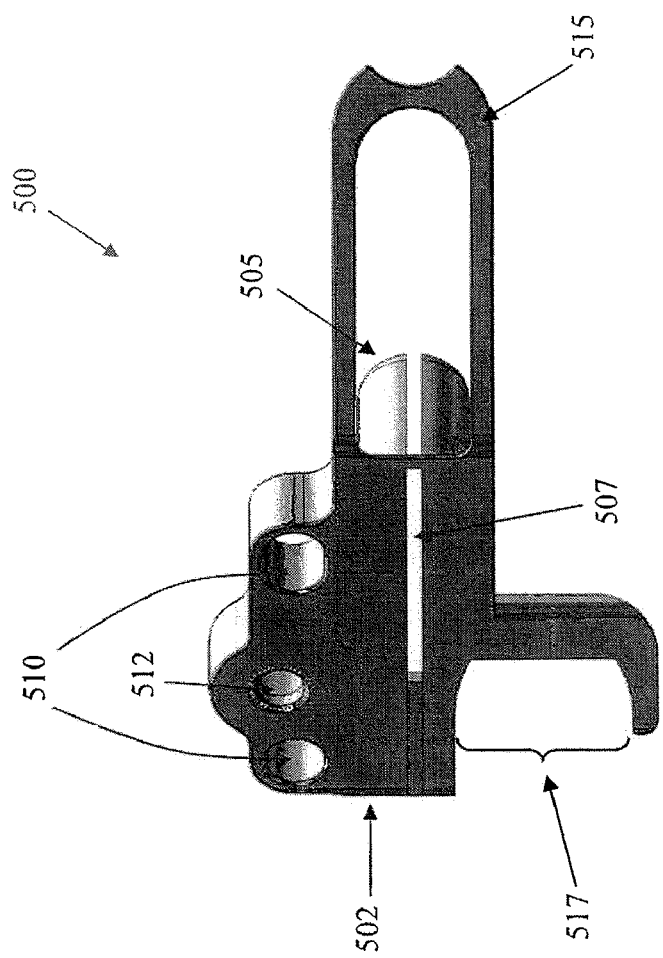

Looking next at FIGS. 31-33, cutting guide 500 is provided in both left and right versions, and preferably in two size versions, i.e., small/medium (SM/MD) and large/extra large (LG/XL). Cutting guide 500 generally comprises a body 502 including a pair of keyhole locating bosses 505, a saw guide slot 507, and a pair of cutting guide mounting holes 510 for mounting on antero-medial fixation pin boss 115 (FIG. 12) and mounting boss 120, respectively, of base 105. Body 502 also comprises a hole 512 for alignment with mount hole 117 (FIG. 11) in base 105 as will hereinafter be discussed in further detail. Body 502 also comprises an anterior safety interlock tab 515 and a neurovascular shield mounting channel 517.

Figure 34:
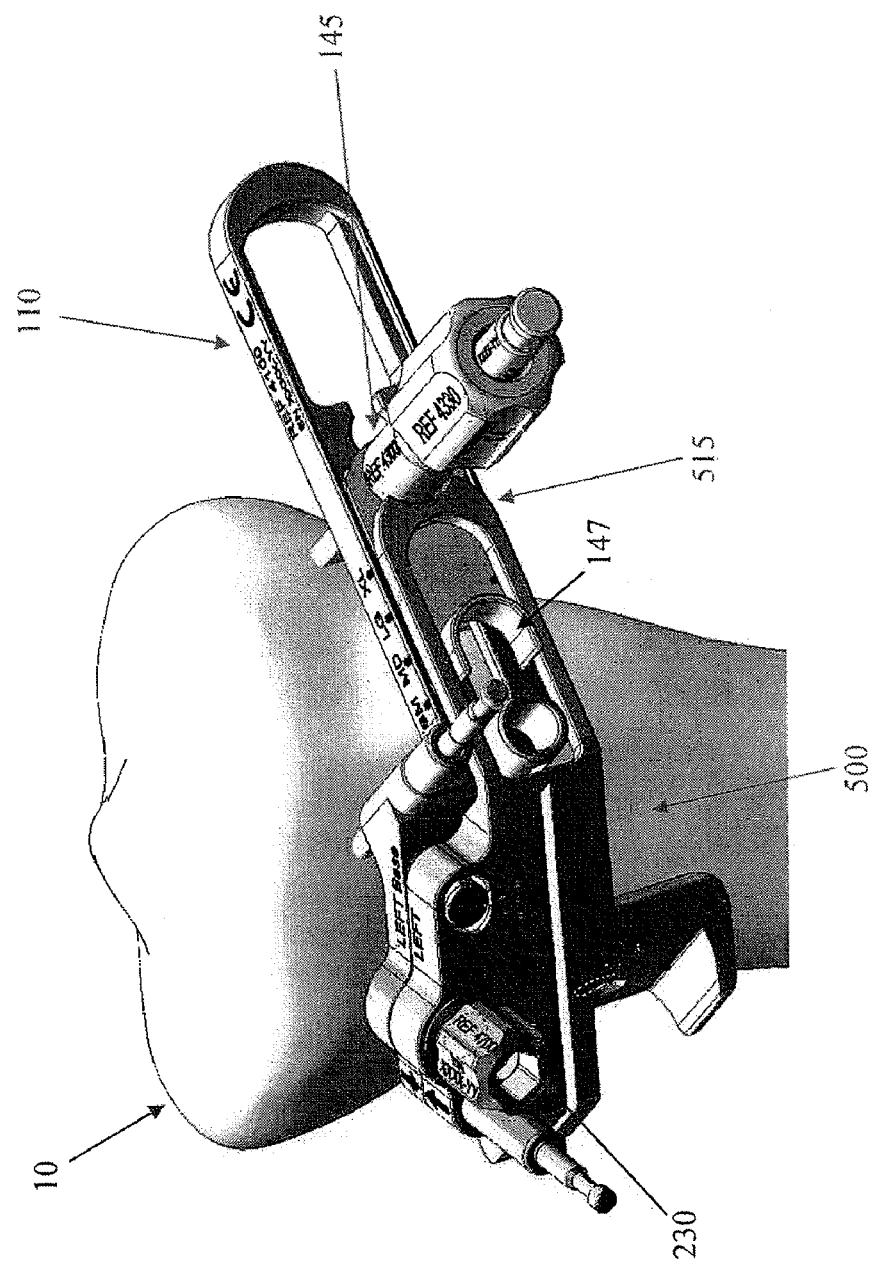
FIGS. 34-36 are schematic views showing proper (FIG. 34) and improper (FIGS. 35 and 36) assembly of the cutting guide to the adjustable base assembly.
Figure 35:
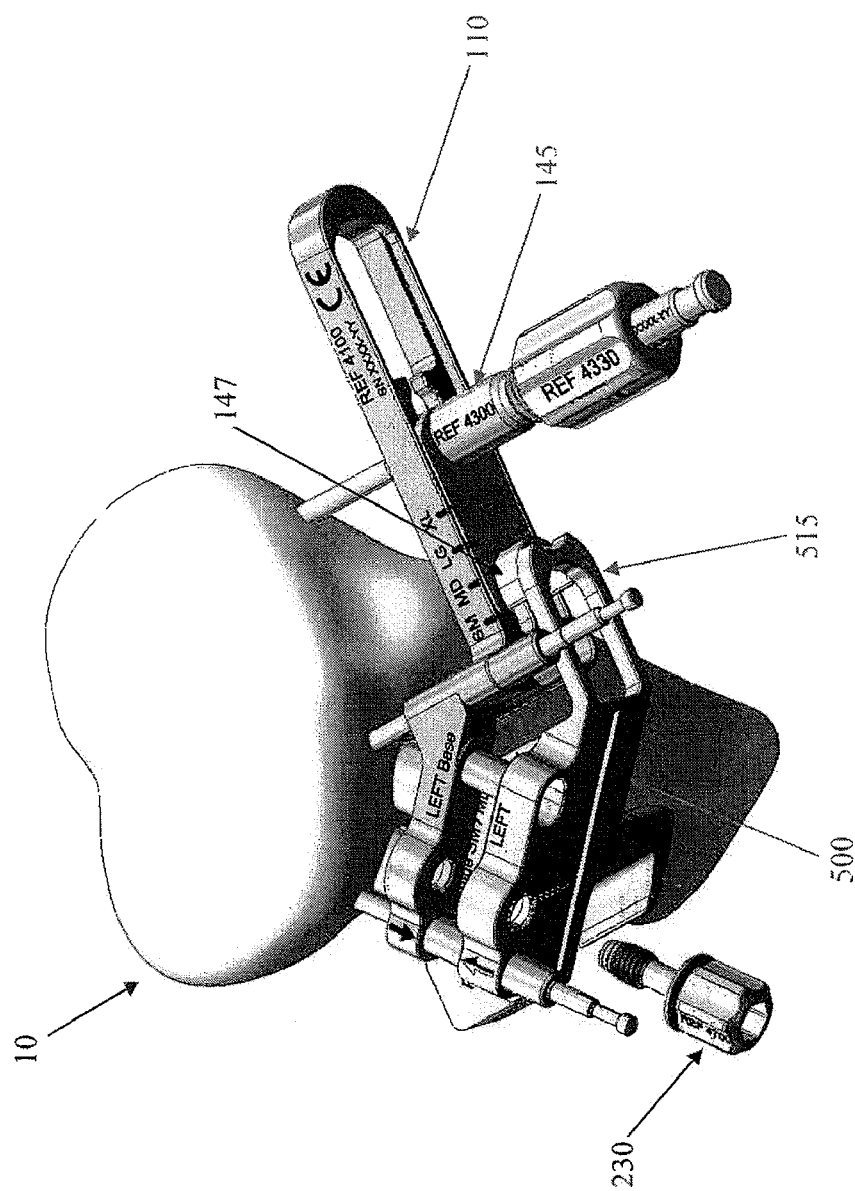
Figure 36:
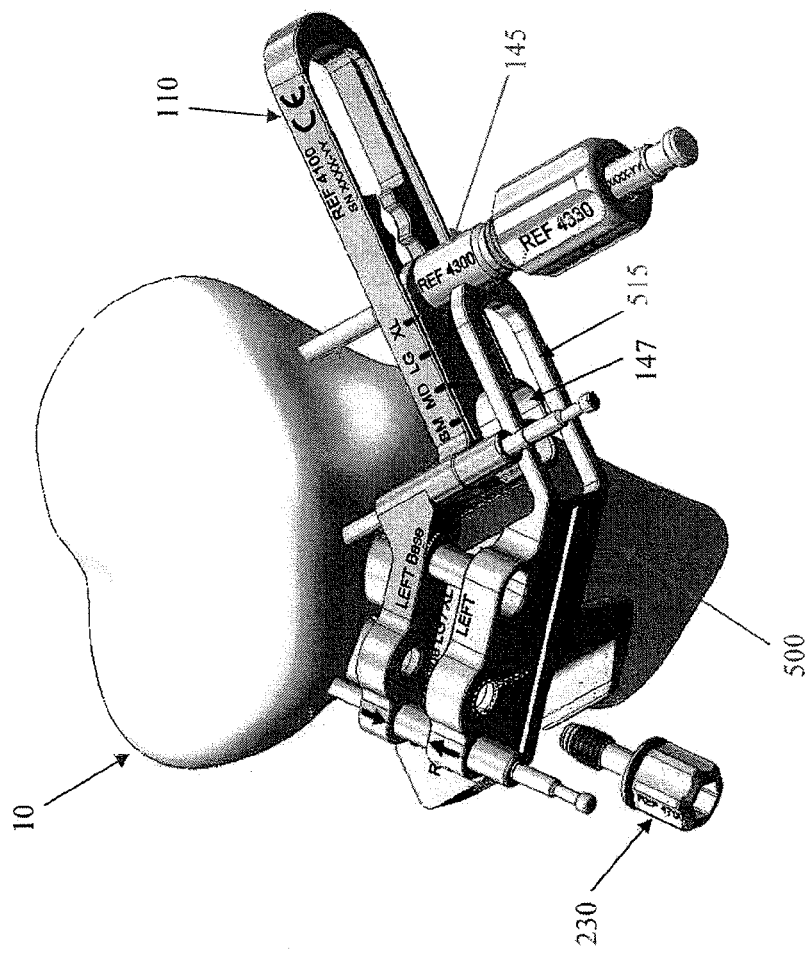

The position of anterior safety interlock tab 515 is such that it would interfere with hinge pin aimer 145 if the wrong size cutting guide 500 is assembled to base 105. That is, if hinge pin slider 133 is disposed in the small (SM) or medium (MD) size position on anterior arm 110, the anterior safety interlock tab 515 on a large/extra large (LG/XL) cutting guide 500 will interfere with the hinge pin slider, thereby preventing the wrong size cutting guide from being assembled to the base and creating a potential safety hazard. See FIGS. 34-36.

Neurovascular Shield Assembly 600

Looking next at FIGS. 37-41, neurovascular shield assembly 600 is provided in left and right versions, and is preferably provided in a variety of sizes, e.g., small/medium (SM/MD), large/extra large (LG/XL), etc. Neurovascular shield assembly 600 generally comprises a neurovascular shield 602, a handle 605 and a threaded fastener 607. Preferably, threaded fastener 607 is identical to threaded fastener 230 discussed above. Neurovascular shield 602 includes a blade guide channel 610 (FIG. 40) to help guide a saw blade during formation of the osteotomy cut (see below). Preferably the size of the portion of the neurovascular shield which mounts in neurovascular shield mounting channel 517 (FIG. 37) is coordinated with the size of neurovascular shield mounting channel 517 so that an incorrectly-sized neurovascular shield is prevented from being mounted on a cutting guide 500 mounted to base 105. In other words, by coordinating the sizing of the height of neurovascular shield 602 and neurovascular shield mounting channel 517 (and the corresponding hole in the cutting guide for receiving threaded fastener 630, see below), the design prevents the use of a small (SM) or medium (MD) neurovascular shield on a large/extra large (LG/XL) cutting guide, as well as preventing the use of the large (LG) or extra large (XL) neurovascular shield with the small/medium (SM/MD) cutting guide. In a preferred form of the invention, neurovascular shield 602 is configured to protect the medial collateral ligament (MCL) from damage during sawing of the tibia.

Preferably neurovascular shield 602 has a shaped tip 615 (FIG. 40) with multiple guide surfaces. The posterior follower surface 617 (FIG. 41) is intended to guide the tip of the neurovascular shield around the posterior of the tibia, allowing the surgeon to feel the shield in contact with the cortex of the tibia throughout insertion. The blade exit flat 620 (FIG. 41) is intended to be essentially tangent to the path of the saw blade teeth so as to help prevent burrs from being generated at the tip.

Figure 42:
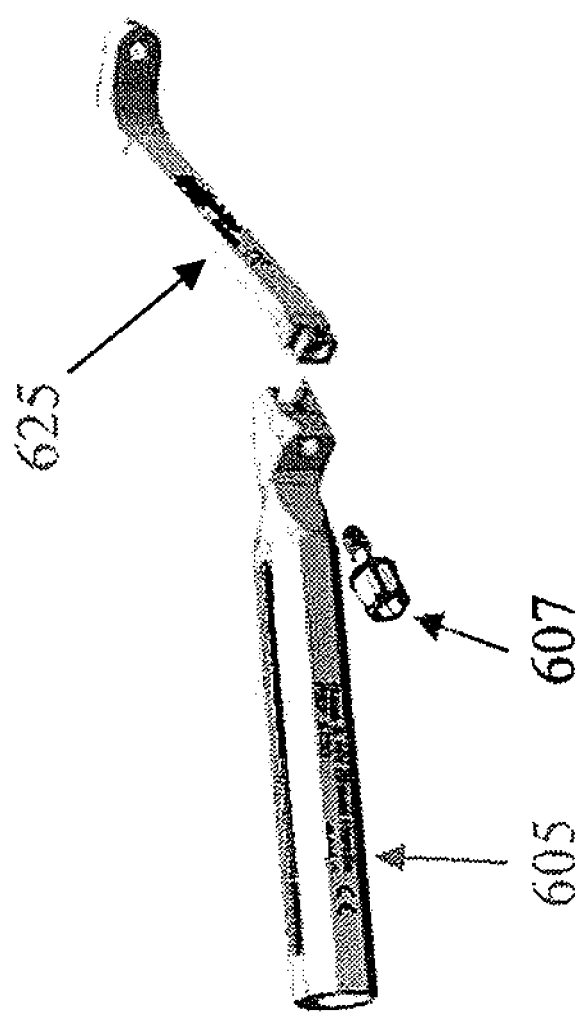
FIGS. 42 and 43 are schematic views showing a stem attached to a handle.
Figure 43:
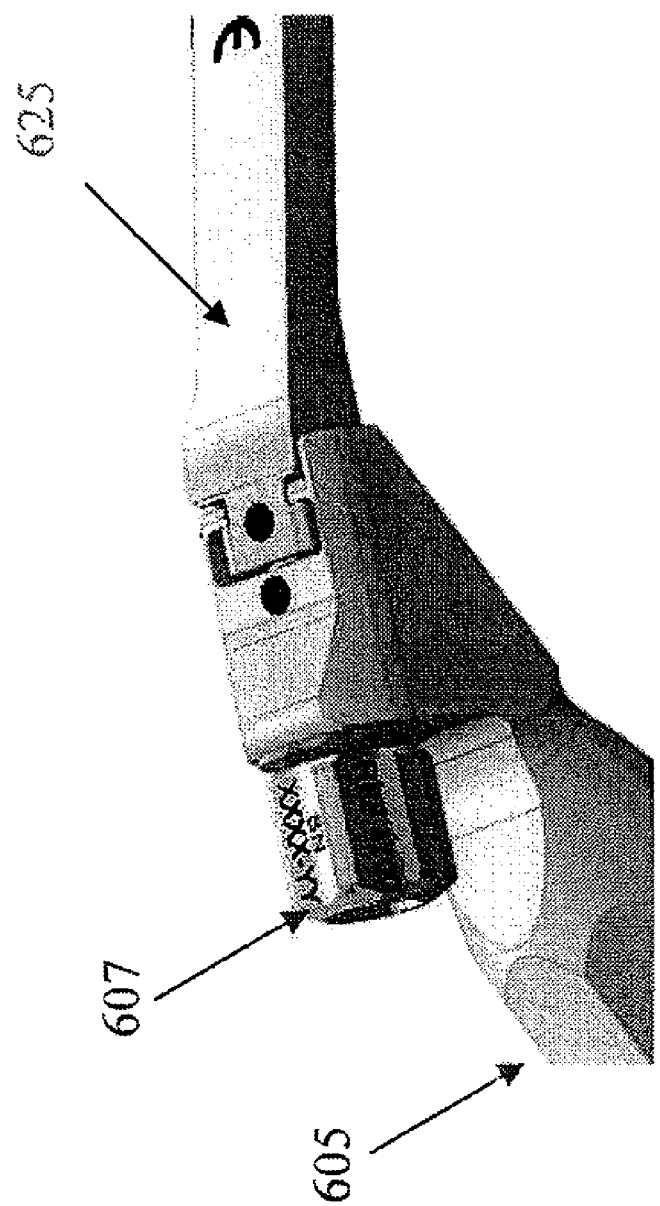

Preferably handle 605 (FIG. 37) is a dual purpose handle. In one application, handle 605 serves to support neurovascular shield 602 (FIGS. 37-41). However, and looking now at FIGS. 42 and 43, handle 605 is preferably configured so that it can also support a stem 625 which can be used to support various elements of the system, e.g., stem 625 can mate with handle mounting channel 240 (FIG. 22) of keyhole drill guide 200.

Opening Jack Assembly 700

Figure 44:
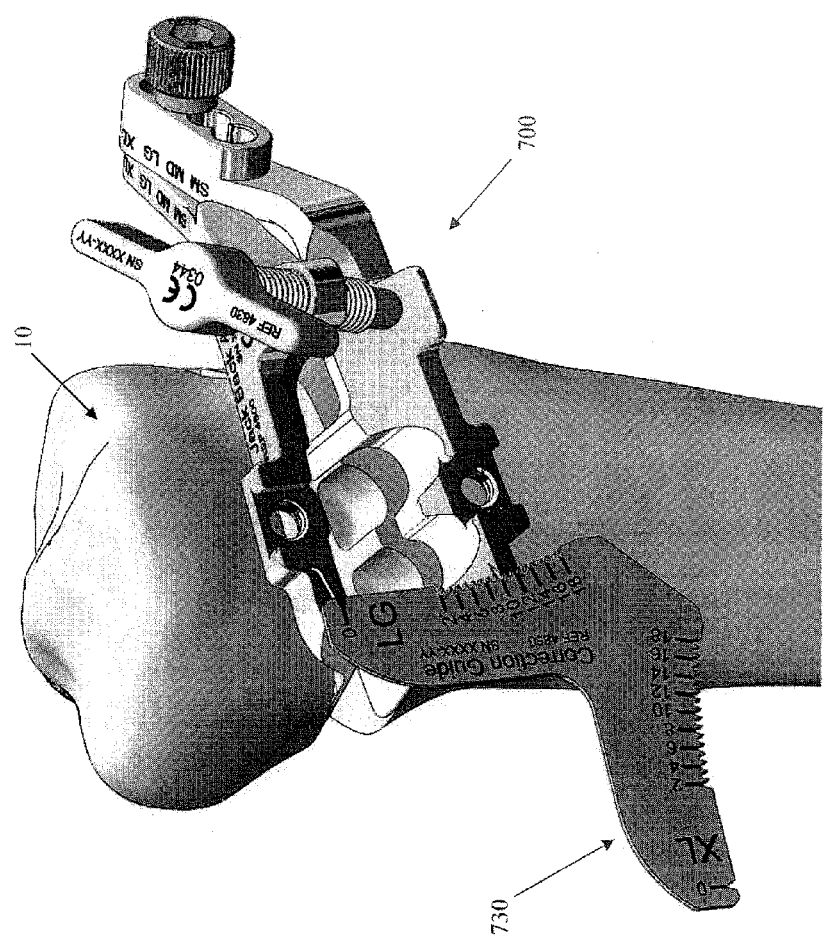
FIGS. 44-46 are schematic views showing an opening jack assembly.
Figure 45:
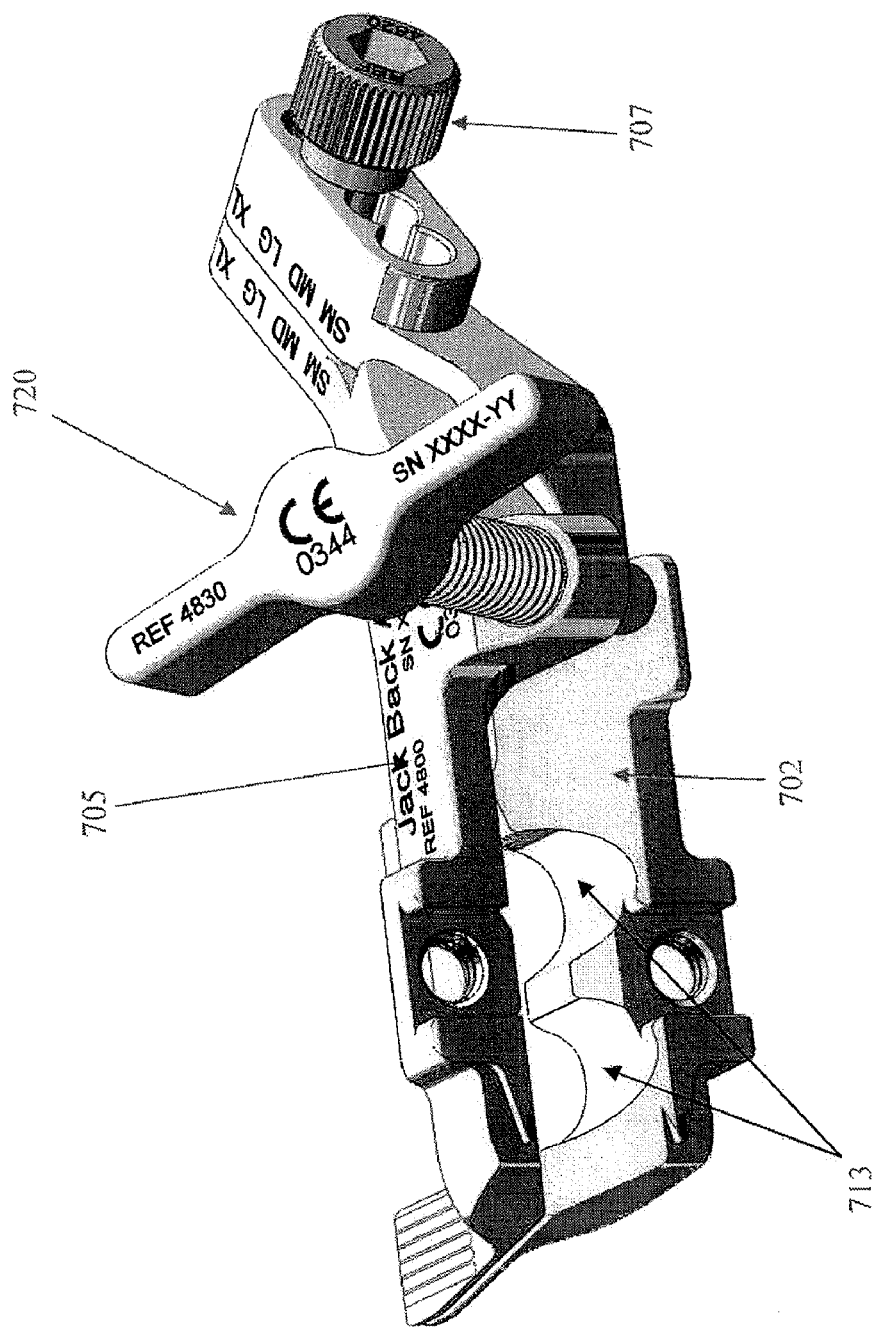
Figure 46:
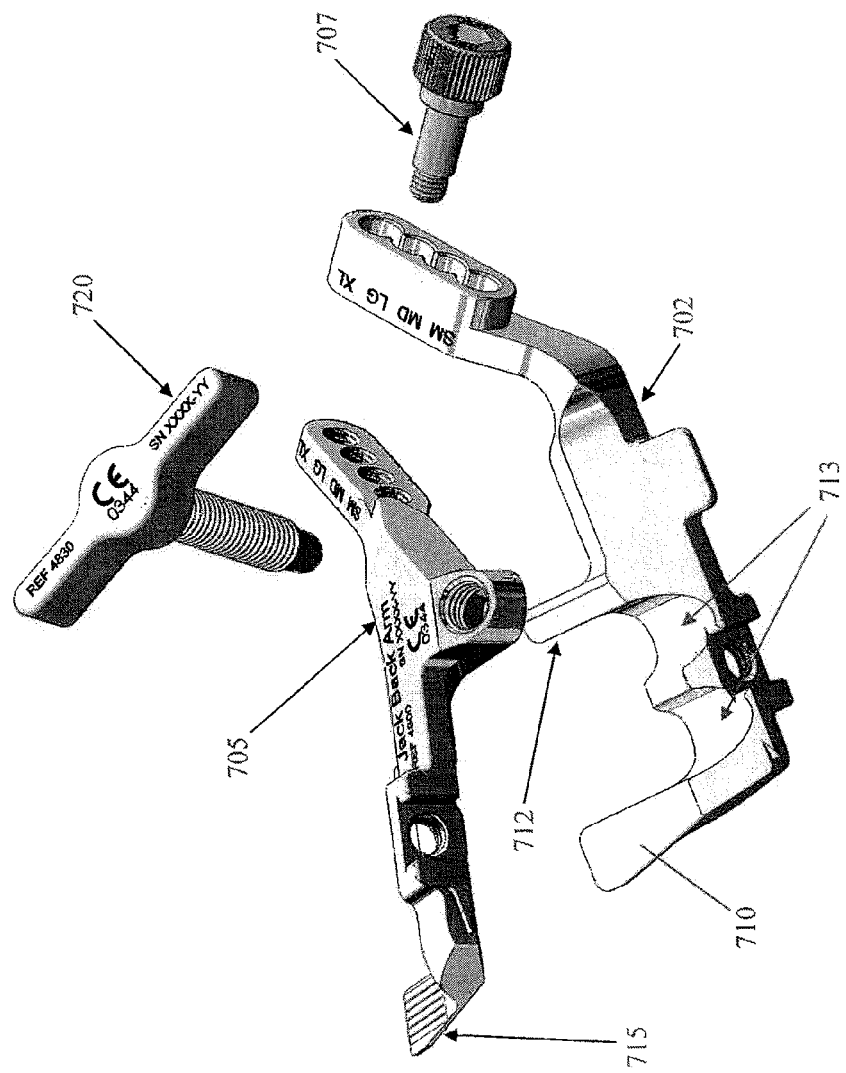

Looking next at FIGS. 44-46, opening jack assembly 700 may be used for both the left and right knees, with one size of opening jack assembly being capable of accommodating all different sizes of tibias. Opening jack assembly 700 generally comprises a bottom arm 702 (FIG. 45) and a top arm 705 pivotally connected together by a thumb screw 707. Bottom arm 702 includes a medial paddle 710 (FIG. 46), an anterior paddle 712 and keyhole apertures 713 which permit opening jack assembly 700 to be aligned with keyholes formed in the tibia, as will hereinafter be discussed in further detail. Top arm 705 includes a medial paddle 715. An opening jack turn key 720 (FIG. 45) is used to open arms 702 and 705 relative to one another, whereby to open the osteotomy to the desired correction angle, as will hereinafter be discussed in further detail. FIGS. 45 and 46 are the preferred embodiment because they are also adjustable for a variety of tibia sizes, but do not require a special bushing 722 as discussed below with respect to the construction shown in FIGS. 47 and 48. The size adjustment is made simply by placing thumbscrew 707 into the selectable tibia size.

Figure 47:
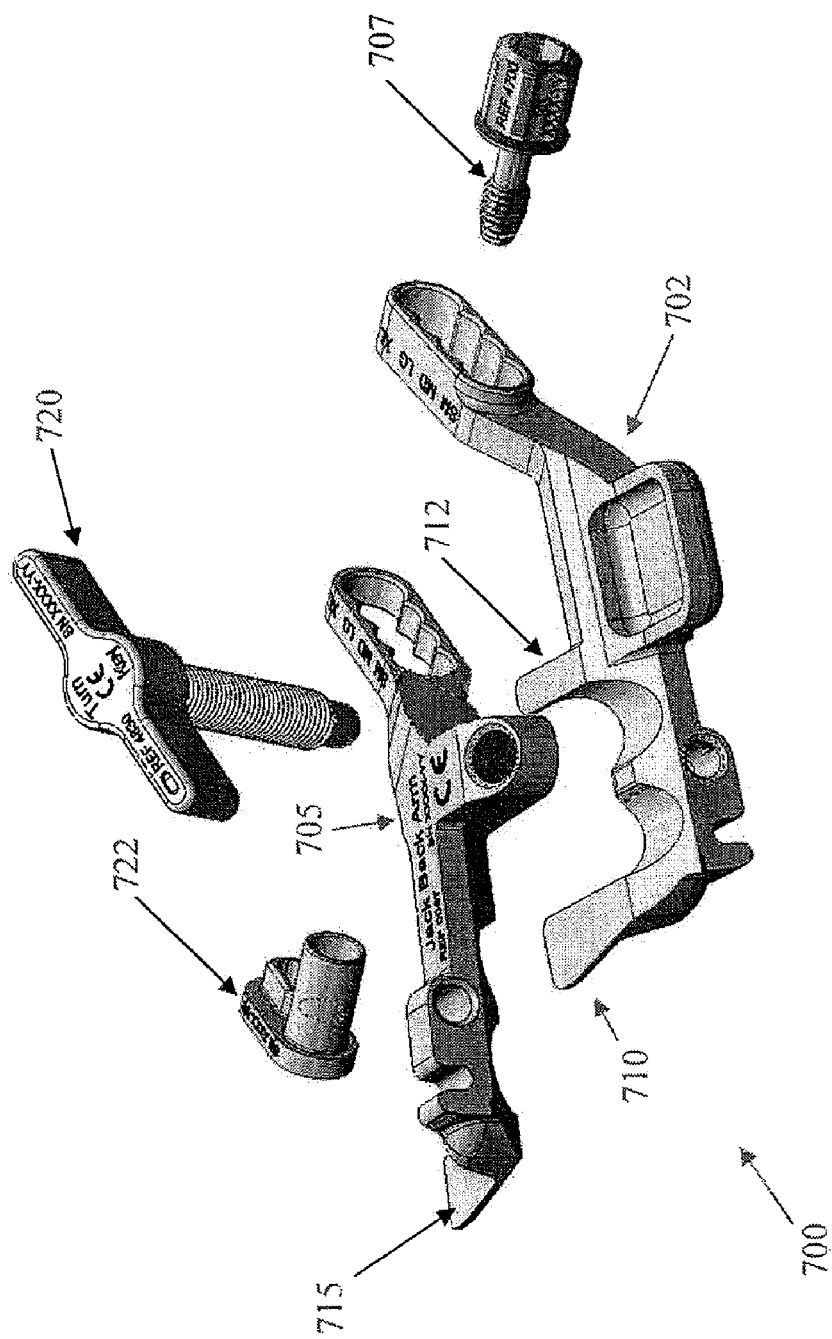
FIGS. 47 and 48 are schematic views showing an alternative opening jack assembly also formed in accordance with the present invention.
Figure 48:
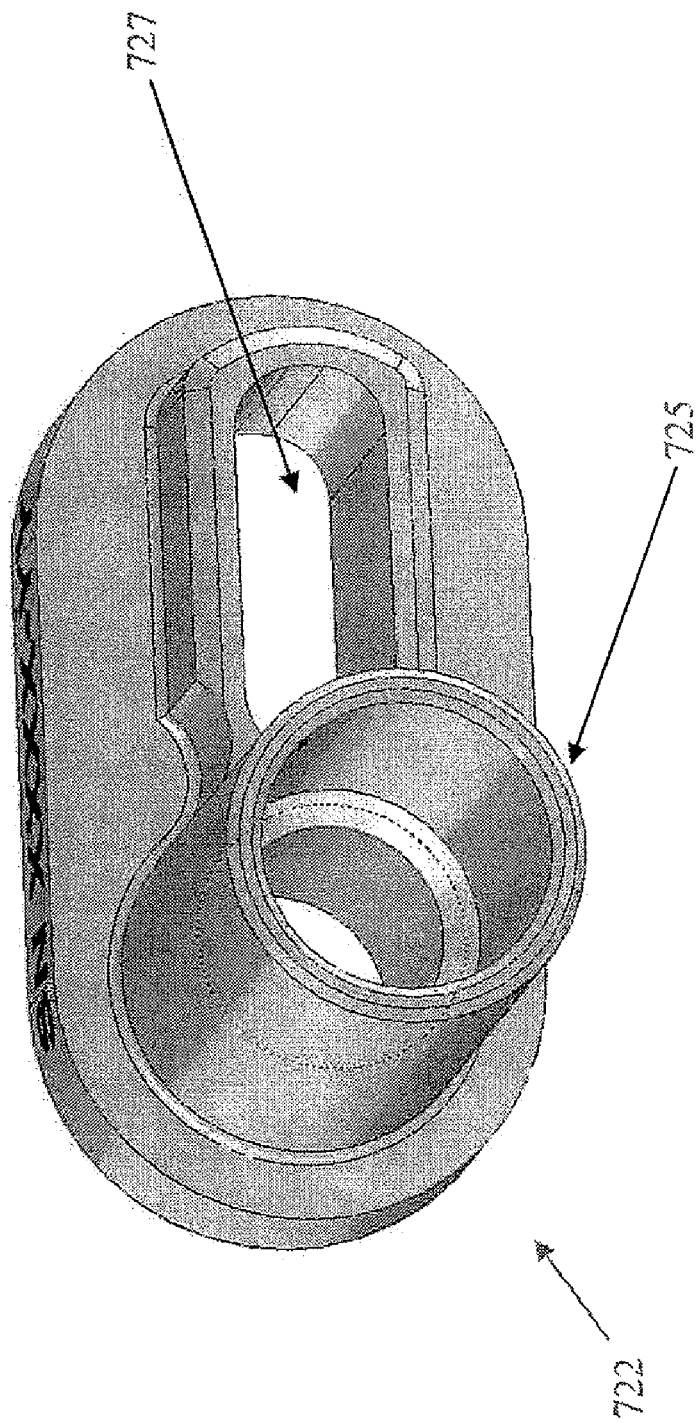

In an alternative form of the invention, and looking now at FIGS. 47 and 48, opening jack assembly 700 also includes a jack hinge bushing 722. Jack hinge bushing 722 includes a jack bushing hinge barrel 725 (FIG. 48) and a lateral cortex viewing window 727. Lateral cortex viewing window 727 allows the lateral cortex of the tibia to be examined under fluoroscopy. The opening jack assembly 700 shown in FIGS. 47 and 48 is adjustable for various size tibias. More particularly, after the size of the tibia is determined, the opening jack assembly is assembled to a configuration to match the size of the tibia—hinge bushing 722 is inserted into the appropriately-marked hinge aperture on top arm 705, the corresponding aperture on bottom arm 702 is aligned with the barrel of the hinge bushing, and then the two arms are secured together with threaded fastener 707. This places the hinge of the jack assembly in line with the bony hinge axis of the osteotomized tibia. Turn key 720 is then threaded through the mating hole on top arm 705 of the jack assembly and used to open the cut tibia to the proper extent.

Implant 800

Looking next at FIGS. 49-54, implant 800 may be used for both the left and right knees, and is preferably provided in a range of sizes for use with different sizes of tibias. Implant 800 comprises an implant base 810. Base 810 preferably comprises a pair of keys 820, 825. Keys 820, 825 are laterally displaced along the width of base 810, in a "side-by-side" configuration. Among other things, it has been found that this "side-by-side" key configuration provides, at the base of the implant, excellent load-bearing characteristics and substantial resistance to rotational and shear forces. Base 810 preferably comprises serrations 826 for enhancing engagement between implant 800 and the surrounding bone, when implant 800 is positioned within the osteotomy. Base 810 also preferably comprises a medial tab 871 and a lateral tab 872.

Keys 820, 825 each include a pair of bores 833', 833" and 834', 834", respectively. Bores 833', 833", 834' and 834" receive locking fixation screws 865 (FIG. 50) for fixing implant 800 to the tibia, as will hereinafter be discussed in further detail. Bores 833' and 833", and bores 834' and 834", preferably diverge from the longitudinal axes of keys 820, 825, respectively, in the manner shown in FIGS. 49, 50, 52 and 54, so as to direct fixation screws 865 downwardly and upwardly into the adjacent portions of the tibia. Keys 820, 825 may also include external ribs if desired (not shown).

Figure 51:
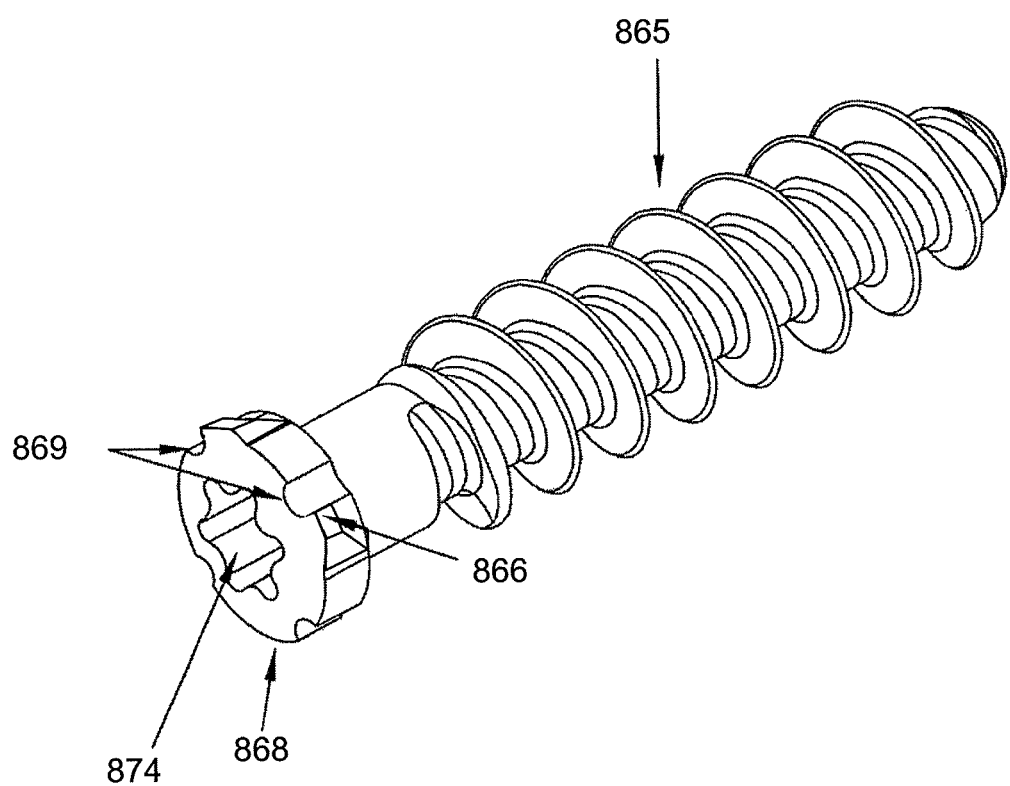
Figure 52:
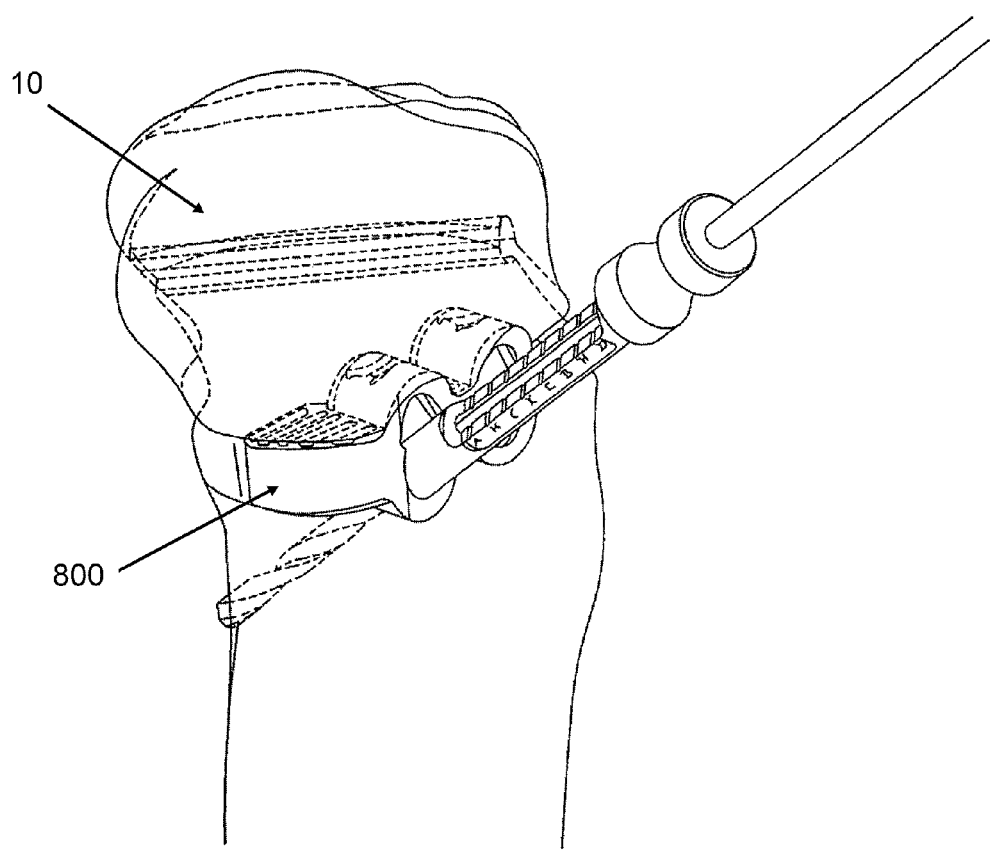
Figure 53:
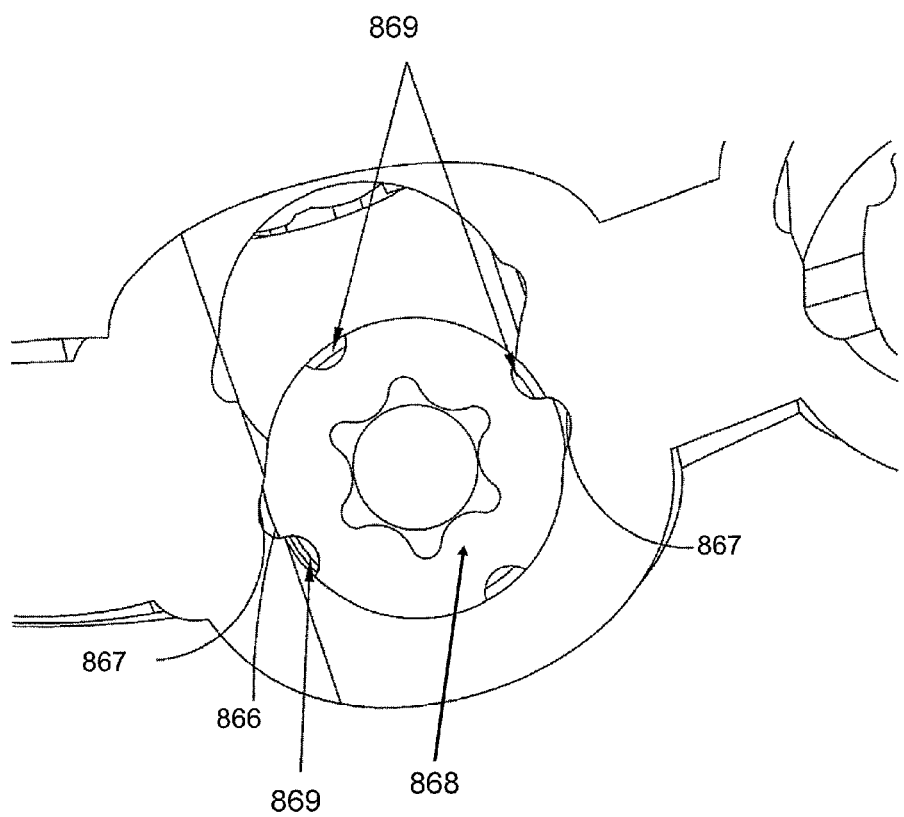
Figure 54:
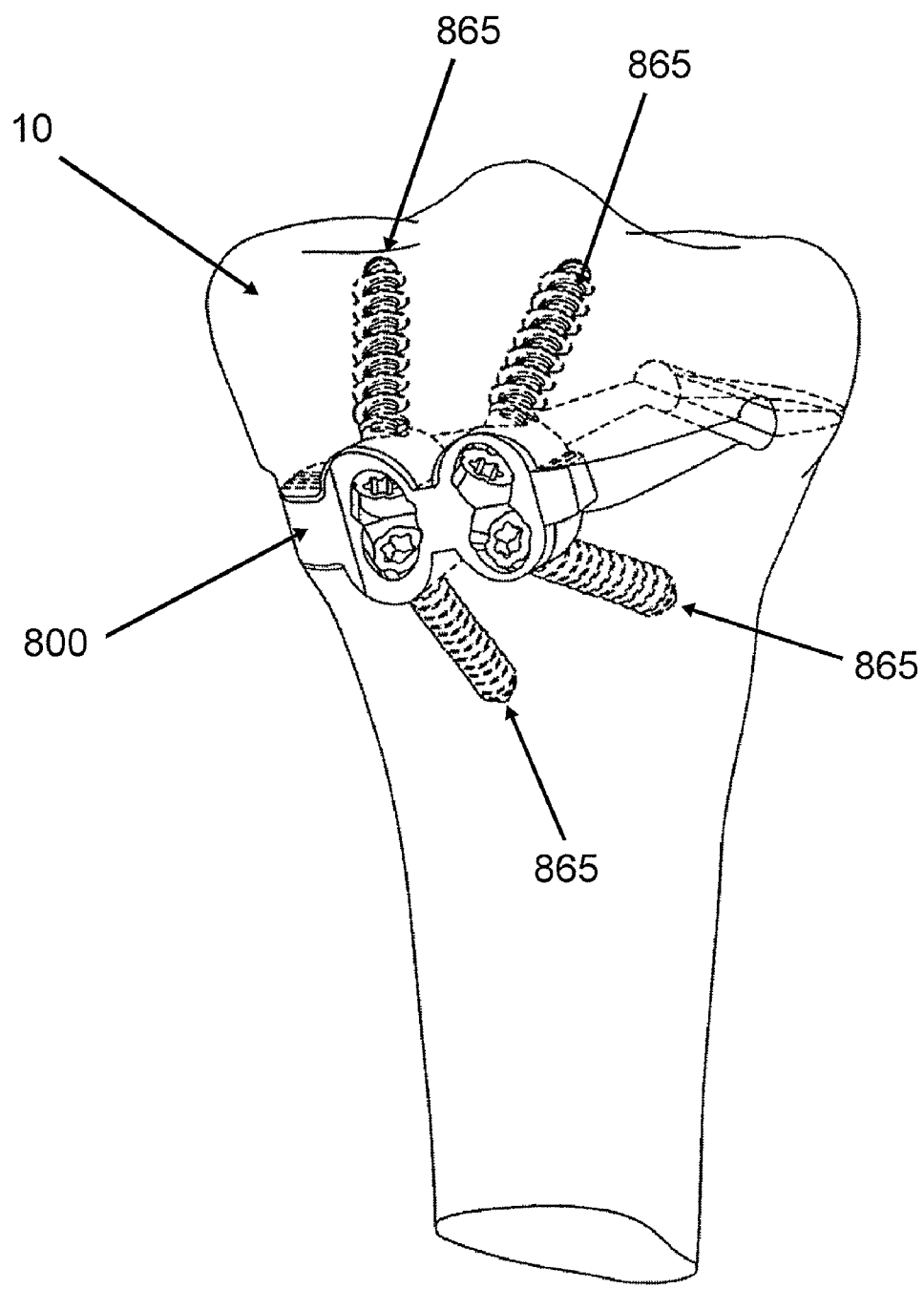

Preferably, a locking feature is provided to releasably lock fixation screws 865 to implant 800. In one preferred form of the present invention, fixation screws 865 may comprise protrusions 866 (FIGS. 51 and 53) for releasably seating in detents 867 (FIGS. 49 and 53) formed in implant 800 as the fixation screws are advanced through the implant, whereby to releasably lock fixation screws 865 to the implant. The exemplary screw 865, shown in FIG. 51 is demonstrated with a Hexalobe Drive (ASTM 543-02) 874.

More particularly, each of the fixation screws 865 has a generally cylindrical head 868 having one or more circumferential protrusions 866. Preferably a circumferential recess 869 is formed in cylindrical head 868 adjacent to circumferential protrusion 866, in order to permit resilient deformation of the fixation screw's protrusion while the fixation screw is being seated in the implant (but before the protrusion is seated in the implant detent). If desired, additional circumferential recesses 869 may also be provided at locations other than immediately adjacent to the circumferential protrusions 866, whereby to provide additional resiliency to head 868. The detents 867 are formed in the implant base, in the sidewall which defines bores 833', 833", 834' and 834". Detents 867 are sized so as to receive screw protrusions 866, whereby to releasably lock fixation screws 865 within bores 833', 833", 834' and 834". Thus, in use, as fixation screws 865 are advanced through bores 833', 833", 834' and 834", their protrusions 866 will seat in body detents 867, whereby to releasably lock the fixation screws to the implant.

Preferred Method for Performing the Open Wedge, High Tibial Osteotomy

With the present invention, the surgeon first determines (using methods well known in the art) the degree of correction necessary to correctly re-align the weight-bearing axis of the knee; then the surgeon uses the system to make the appropriate cut 20 (FIG. 1) into the tibia; then the surgeon opens the cut bone to the extent required so as to form the desired wedge-like opening 25 (FIG. 2) in the tibia; and then the surgeon stabilizes the tibia in its corrected configuration (e.g., with the novel implant 800) while healing occurs.

In a preferred form of the invention, the novel osteotomy system is configured so that:

(i) the axis 70 (FIG. 8) formed at the lateral limit of the osteotomy cut 20 (which forms the lateral limit of the remaining bony hinge when the osteotomy cut 20 is thereafter opened) is parallel to the A-P tibial slope;

(ii) the axis 70 of the lateral limit of the bony hinge created by the osteotomy cut lies in a plane that is perpendicular to the frontal (i.e., coronal) plane; and (iii) when the osteotomy cut 20 is completed and wedge 25 is opened, the distal (i.e., lower) tibia is rotated about the bony hinge so as to substantially maintain, in anatomical alignment, the A-P slope and the frontal plane.

In a preferred form of the invention, the novel osteotomy system is also configured so that:

(iv) the osteotomy can be performed less invasively; and (v) the osteotomy can be performed with minimum incising of soft tissue such as the medial collateral ligament (MCL), the lateral collateral ligament (LCL), and the hamstrings.

In a preferred form of the invention, the novel osteotomy system is also configured so that the delicate neurological and vascular tissues at the back of the knee are fully protected during the osteotomy procedure.

In one preferred form of the present invention, the open wedge, high tibial osteotomy performed as follows.

A vertical incision is first made on the antero-medial portion of the knee, approximately 1 cm from the medial edge of the patellar tendon, with the incision beginning approximately 2.5-3 cm superior to the anterior tibial tubercle, and extending approximately 6-10 cm in length.

The soft tissue between the patellar tendon and the proximal surface of the tibia is then dissected in order to make a small tunnel-like opening beneath the patellar tendon, just above the patellar tendon's insertion to the proximal tibia.

Figure 10:
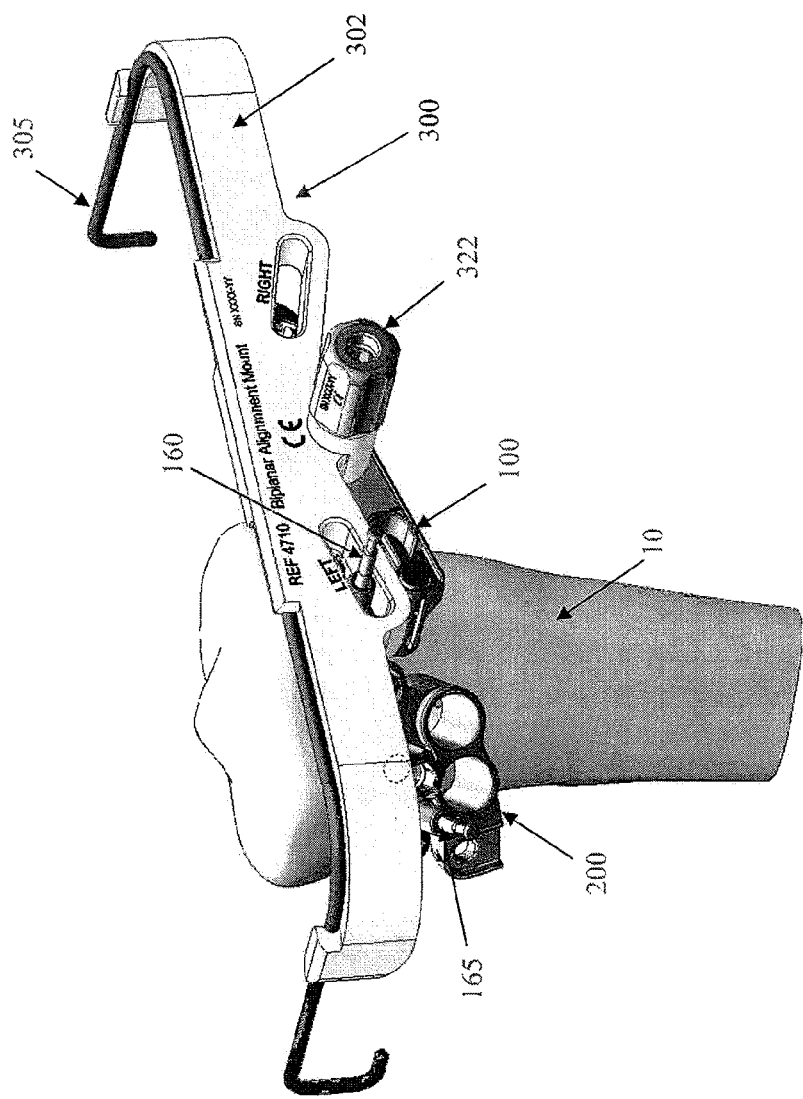
FIG. 10 is a schematic view showing an adjustable base assembly, a keyhole drill guide and a biplanar alignment assembly mounted to a tibia.

Looking now at FIG. 10, showing the instrumentation assembled to the proximal tibia, adjustable base assembly 100, keyhole drill guide 200 and biplanar alignment assembly 300 are assembled together as a unit, i.e., by mounting keyhole drill guide 200 to base 105 of adjustable base assembly 100 and securing it in place with threaded fastener 230, and by mounting biplanar alignment assembly 300 to anterior arm 110 of adjustable base assembly 100 and securing it in place with collet nut 322. More particularly, keyhole drill guide 200 is mounted to base 105 of adjustable base assembly 100 by fitting mount hole 215 (FIG. 22) and mount hole 225 over antero-medial fixation pin boss 115 and mounting boss 120, respectively, and passing threaded fastener 230 through mount hole 220 and into mount hole 117. Biplanar alignment assembly 300 is mounted to anterior arm 110 of adjustable base assembly 100 by passing hinge pin aimer hole 307 (FIG. 25) over hinge pin aimer 145 (FIG. 11) and securing it in place with collet nut 322 (FIG. 10).

Preferably stem 625 is mounted to handle 605 (FIGS. 42 and 43), and then stem 625 is secured in handle mounting channel 240 (FIG. 22), whereby handle 605 may be used to manipulate the foregoing assembly relative to the anatomy.

Still looking now at FIG. 10, the assembly of adjustable base assembly 100, keyhole drill guide 200 and biplanar alignment assembly 300 is moved as a unit to the surgical site. Alternatively, if desired, base assembly 100, keyhole drill guide 200 and handle/stem 605/625 may be moved as a unit to the surgical site; after insertion and general placement onto the tibia, hinge pin slider 133 and biplanar alignment assembly 300 are assembled onto anterior arm 110 and held in place with collet nut 322.

Next, the foregoing assembly (of adjustable base assembly 100, keyhole drill guide 200 and biplanar alignment assembly 300) is maneuvered so that (i) antero-medial locator tab 237 (FIG. 21) is set against the medial aspect of the tibia, (ii) medial locator tab 235 is set against the medial aspect of the tibia, and (iii) patellar tendon protector blade 157 (FIG. 22) is positioned between the tibial tubercle and the patellar tendon (not shown).

Figure 55:
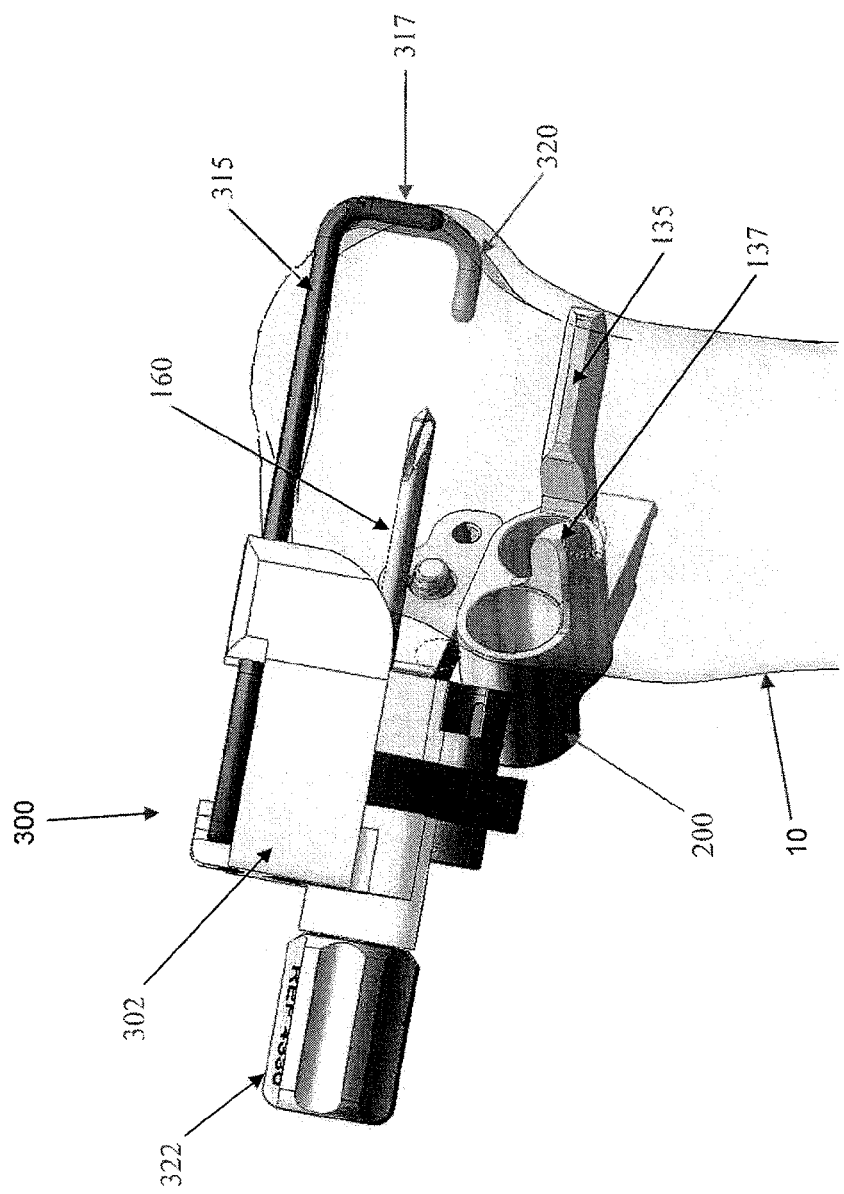
FIGS. 55-57 are schematic views showing the adjustable base assembly, the keyhole drill guide and the biplanar alignment assembly being mounted to the tibia.
Figure 56:
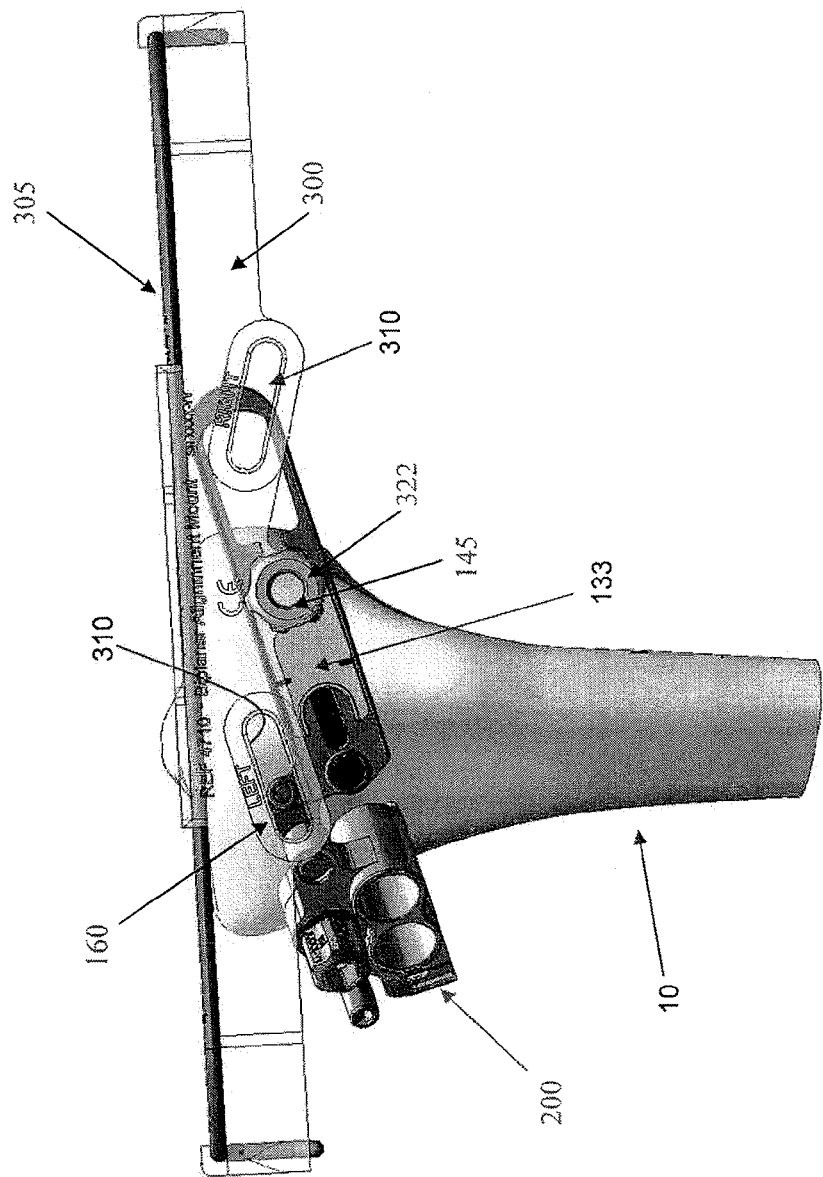
Figure 57:
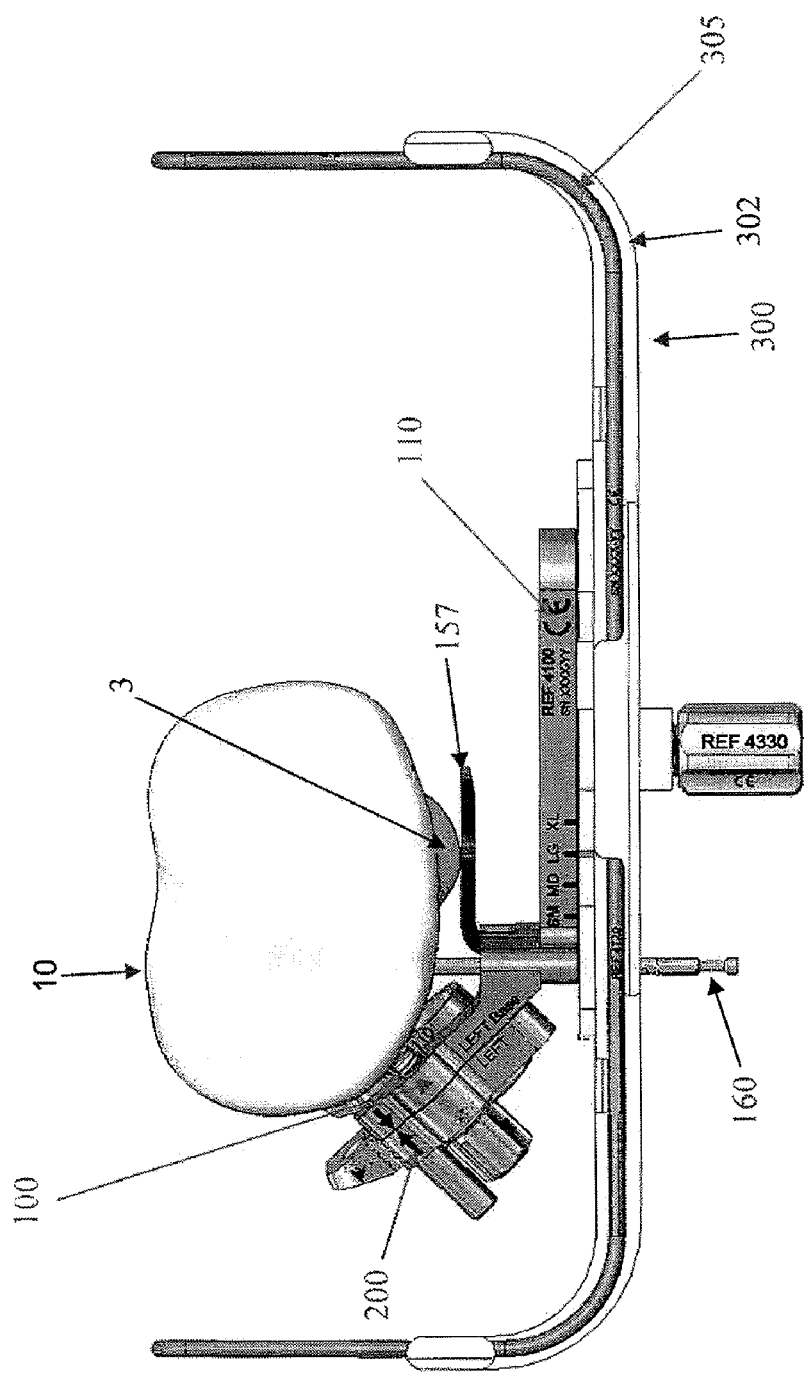

Looking next at FIGS. 55-57, biplanar alignment assembly 300 is then used, in conjunction with a fluoroscope (not shown), to properly align the aforementioned assembly (i.e., the assembled base assembly 100, keyhole drill guide 200 and biplanar alignment assembly 300) with the anatomy.

More particularly, with the fluoroscope aligned in the lateral view, the assembly is aligned with the tibial plateau by using biplanar alignment assembly 300. This is done by aligning side sections 315 with each other, vertical sections 317 with each other, and the underside of the side sections 315 with the tibial plateau (FIG. 55). Then a frontal fixation pin 160 (FIG. 10) is inserted through a frontal fixation pin boss aperture 310 (FIG. 25) in biplanar alignment assembly 300, through frontal fixation pin boss 140 (FIG. 11) and into the tibia.

Significantly, on account of the construction of the aforementioned components and the foregoing operation, the biplanar alignment assembly 300 provides alignment to both the A-P slope of the tibia (FIG. 55) and the sagittal plane of the body (FIG. 56). This alignment is important for proper placement of both hinge pin 400 (see below) and osteotomy cut 20 (see below), and is made possible because the instrumentation automatically takes into account the natural medial-to-lateral slope angle of the tibial plateau. Furthermore the biplanar alignment assembly sets the offset distance from the tibial plateau to the hinge pin (see below) such that the hinge pin is "guided" into the correct location.

At this point, biplanar alignment assembly 300 is removed from the surgical site, by removing collet nut 322 and slipping biplanar alignment assembly 300 off hinge pin aimer 145. Alternatively, biplanar alignment assembly 300 can be left in place on anterior arm 100 until later in the procedure (in this case, and where biplanar alignment assembly 300 of FIGS. 28 and 29 is used, notches 310 hold hinge pin slider 133 in the correct tibia size position).

Figure 58:
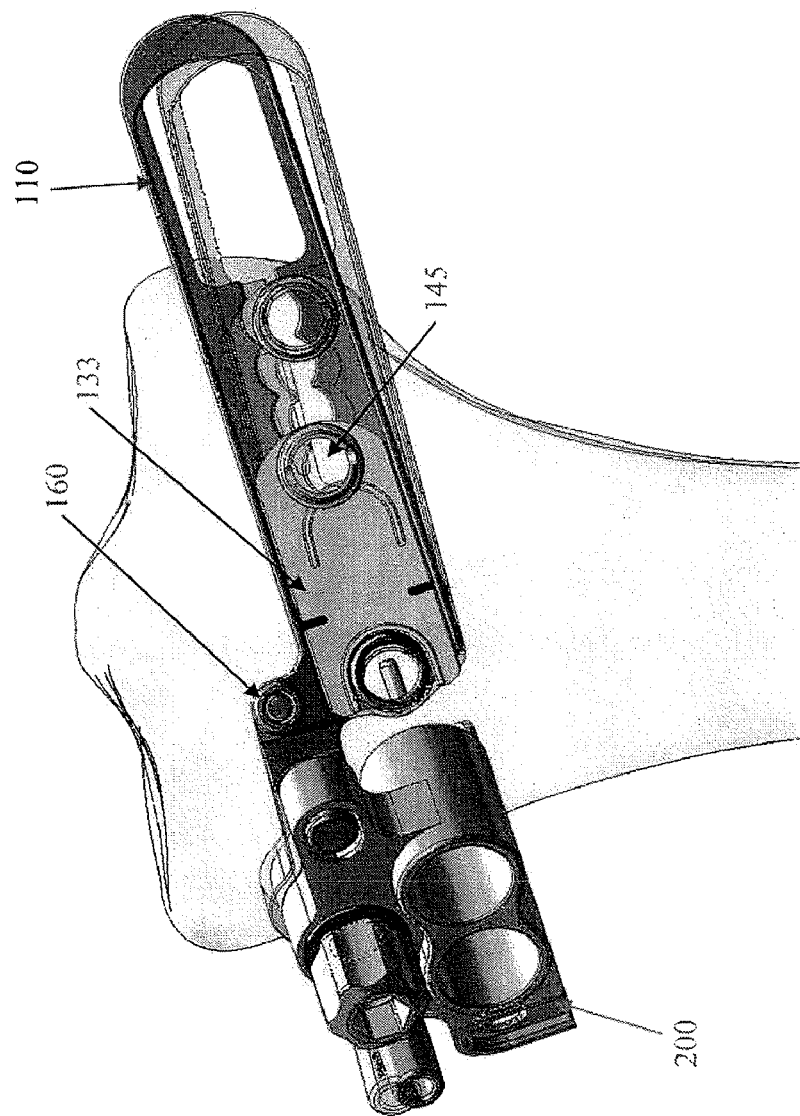
FIG. 58 is a schematic view showing adjustment of the hinge pin position.

Next, with adjustable base assembly 100 and keyhole drill guide 200 fixed to the tibia with only frontal fixation pin 160, it is possible, by viewing down the center hole of hinge pin aimer 145 via fluoroscopy, to (i) rotate anterior arm 110 on frontal fixation pin 160, and (ii) adjust the position of hinge pin slider 133 on anterior arm 110, so as to obtain the desired location for hinge pin 400. See FIG. 58. This rotation has no effect on the alignment with the tibial slope because frontal fixation pin 160 is set parallel to the tibial posterior slope. Therefore, the system has the flexibility to refine the hinge pin location, without disrupting alignment with the A-P tibial slope, while still accommodating various tibial sizes. In other words, during surgery, the multi-position instrumentation can be viewed using fluoroscopy to pinpoint the targeted location of the hinge pin on the tibia and then to adjust that targeted location in situ so as to accommodate various tibia sizes. Adjustment is made by moving hinge pin slider 133 to any of its various positions on anterior arm 110 of base 105.

Figure 59:
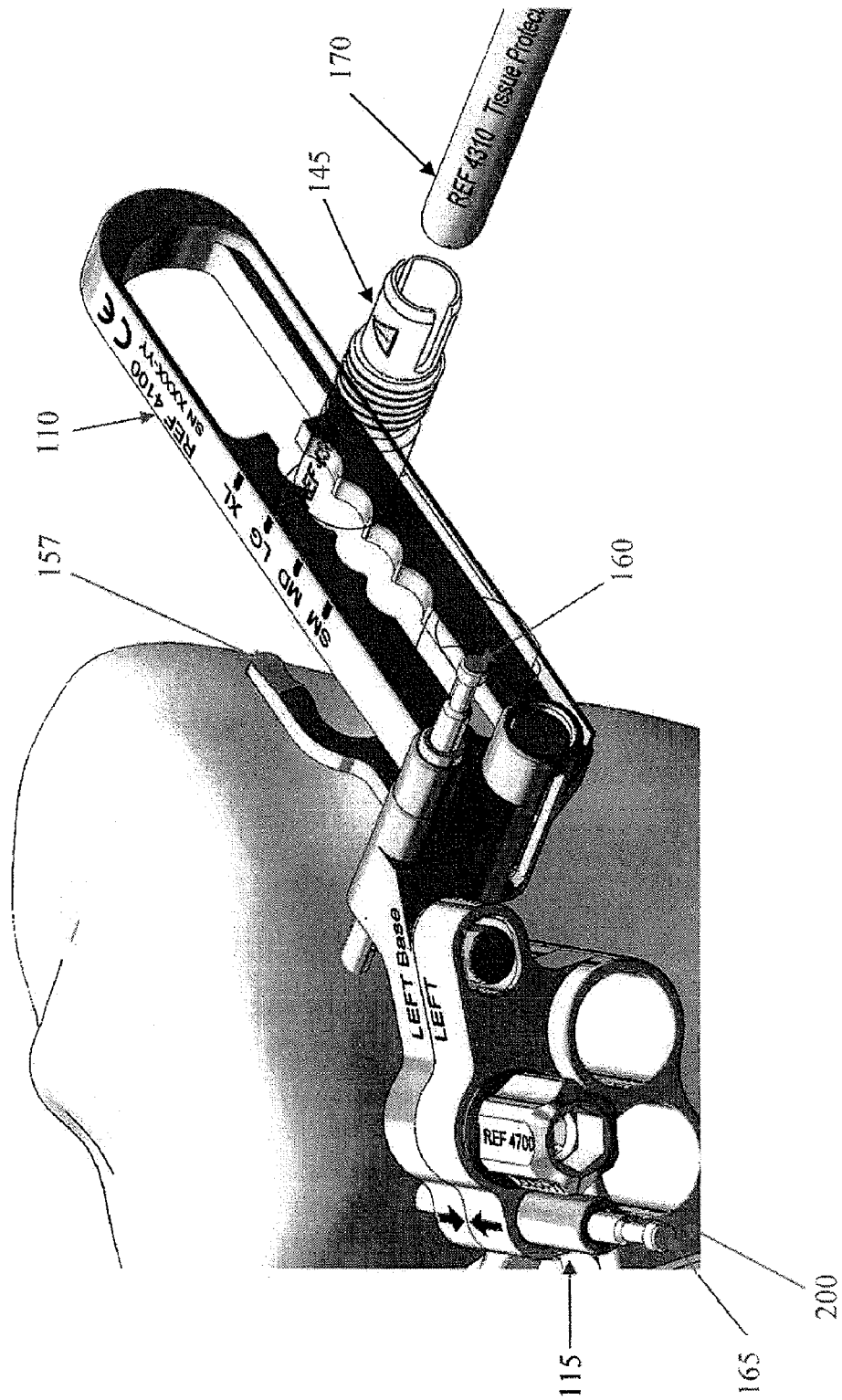
FIGS. 59-64 are schematic views showing how the hinge pin is deployed into the tibia.

The ideal hinge pin location is such that the distance from the hinge pin to the lateral tibial plateau is considerably greater than the distance from the hinge pin to the lateral cortex or the lateral aspect of the tibia. A proper hinge pin location minimizes the probability that the tibial plateau will fracture when the osteotomy is opened, i.e., it minimizes the chances that the bone will fracture proximally in the lateral compartment of the knee. Once anterior arm 110 has been properly rotated, and hinge pin slider 133 has been properly positioned, so that the location the hinge pin has been properly established, an antero-medial fixation pin 165 (FIG. 59) is passed through antero-medial fixation pin boss 115 and into the tibia.

Figure 60:
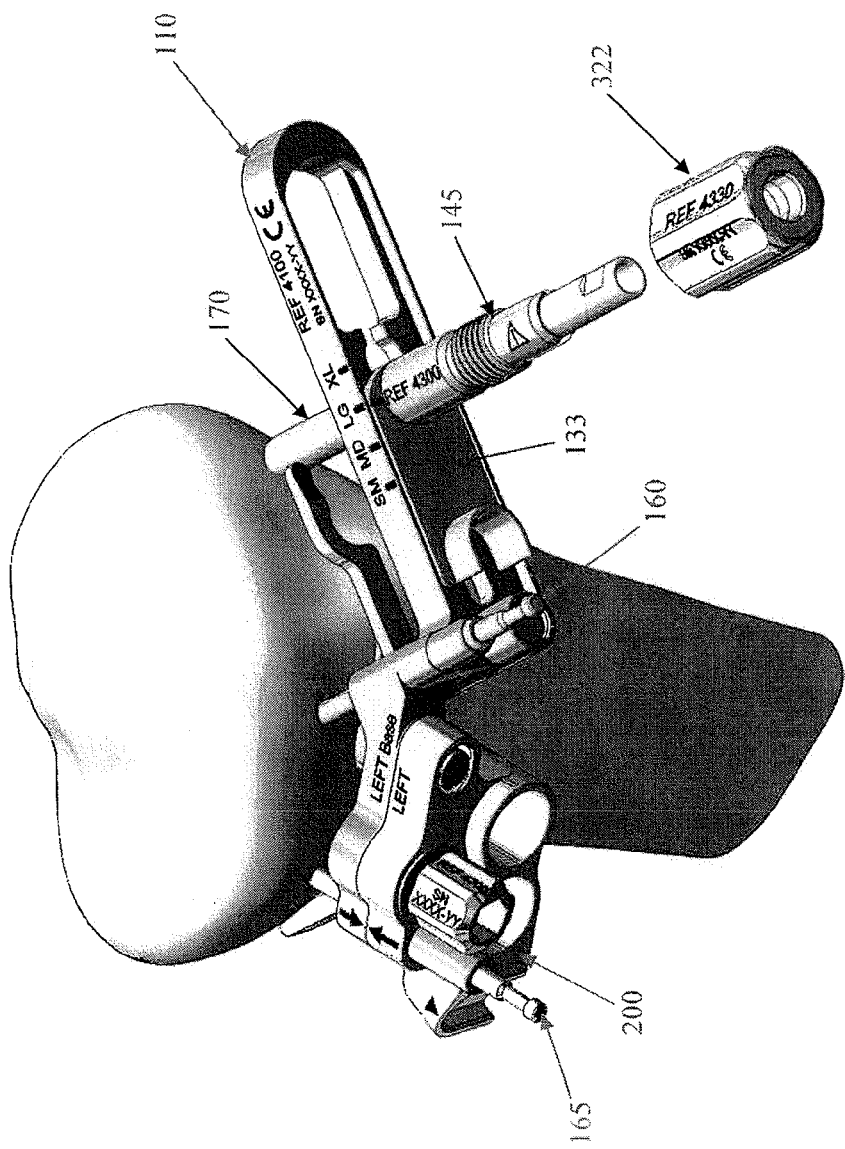
Figure 61:
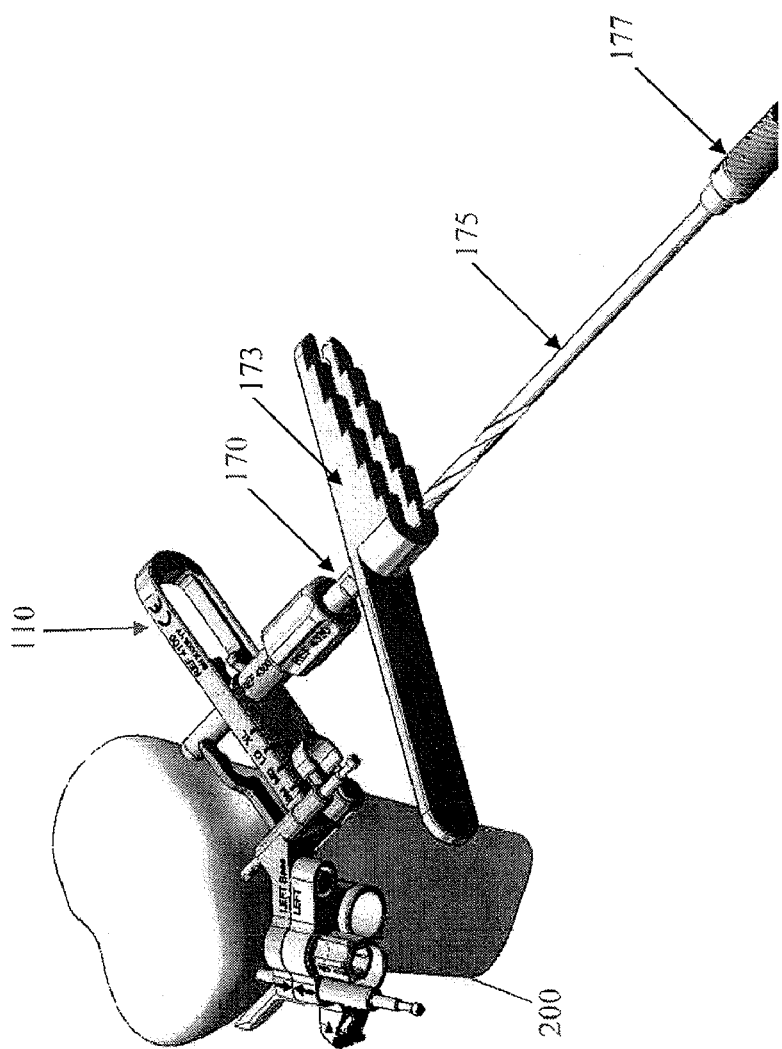
Figure 62:
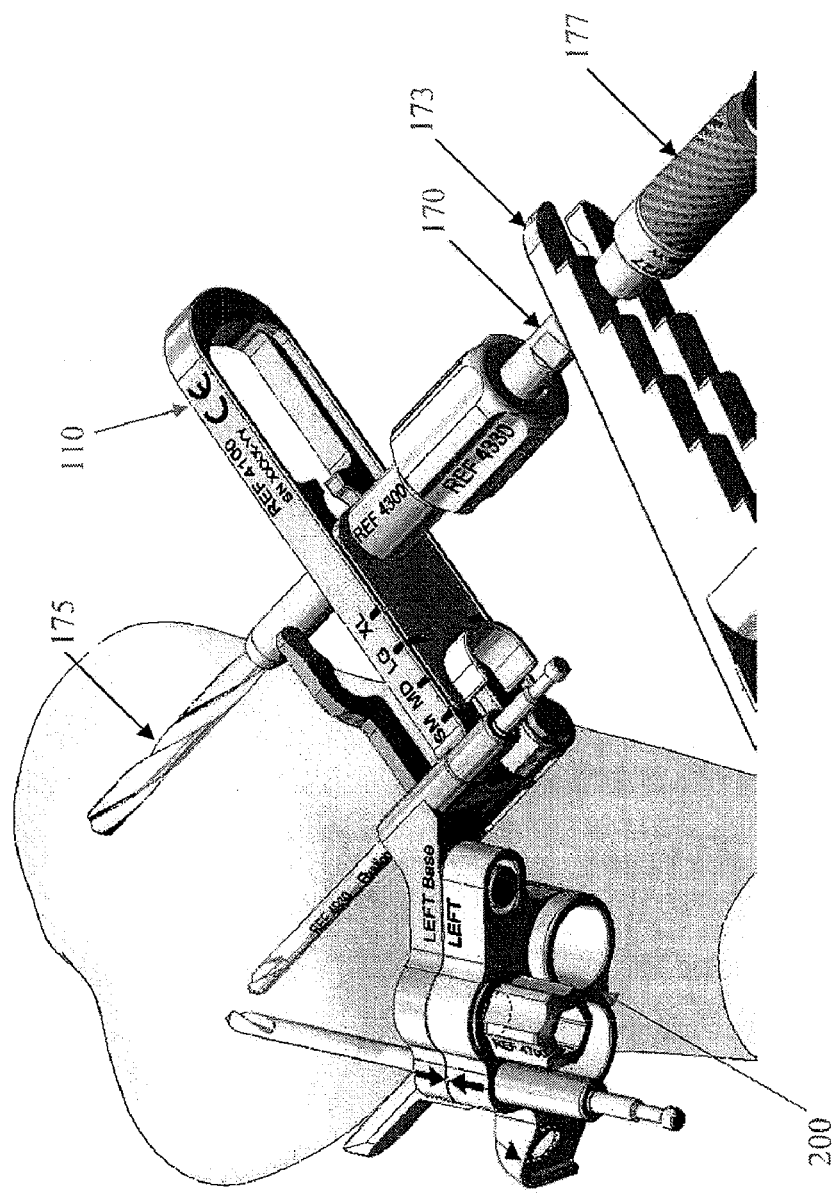
Figure 63:
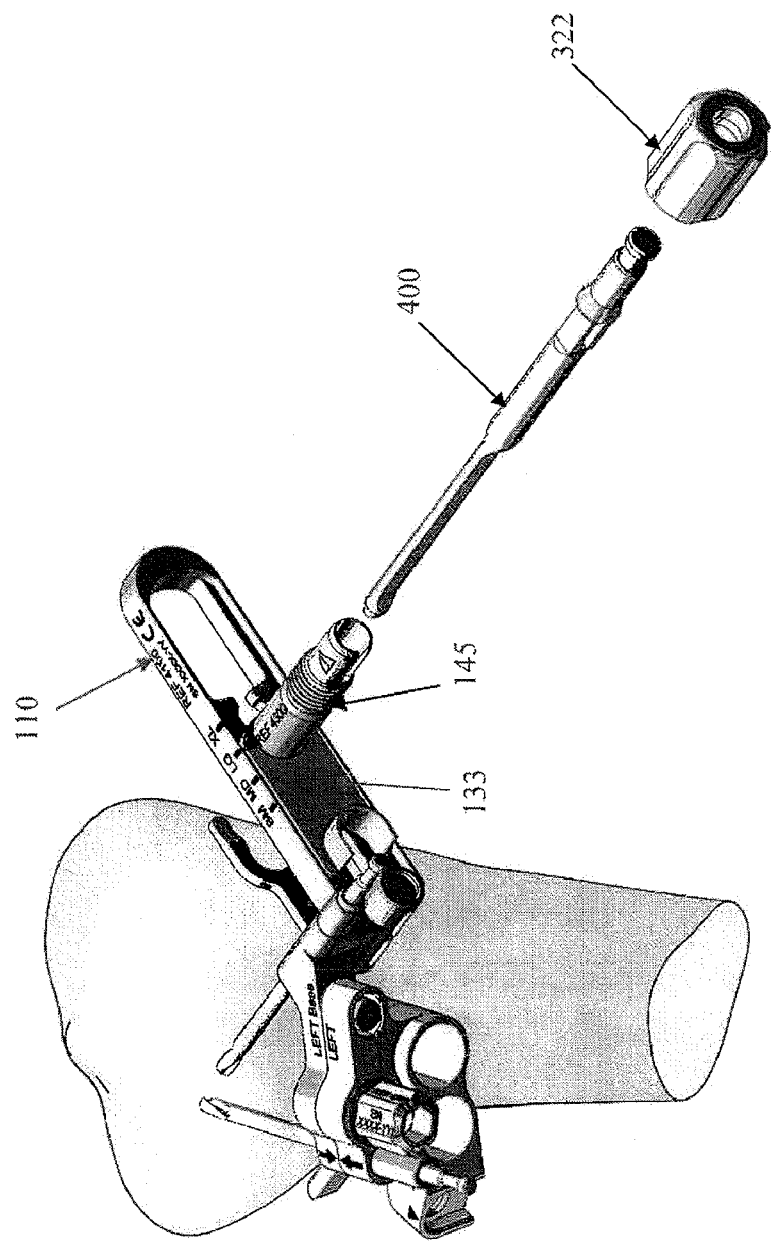
Figure 64:
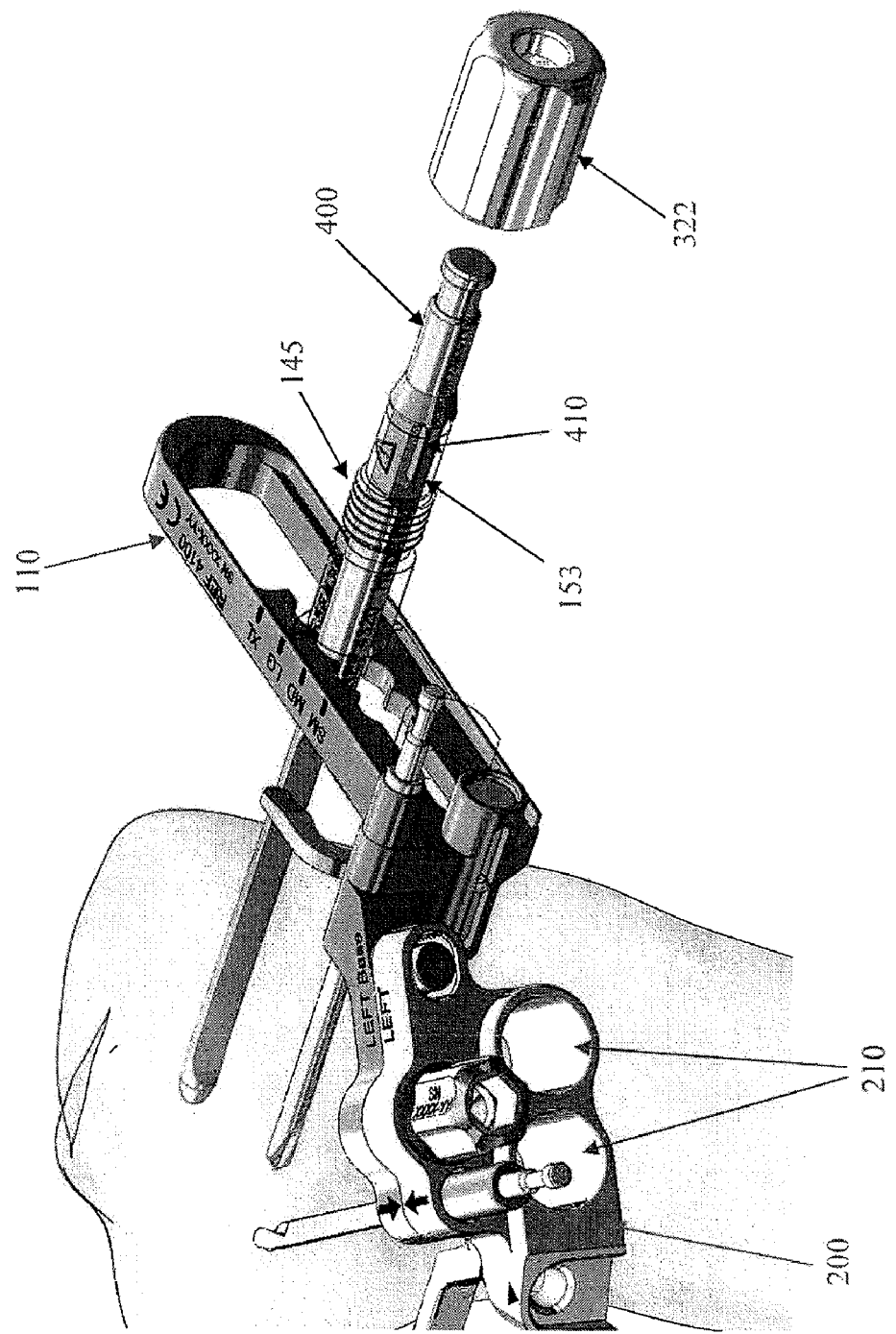

Looking next at FIGS. 59-64, hinge pin 400 is set in the tibia. More particularly, a tissue protector 170 (FIG. 59) is preferably used to protect soft tissue during the hinge pin placement. Tissue protector 170 is inserted into hinge pin aimer 145, passed through a small incision made in the soft tissue (not shown) so as to contact the tibia, and then secured with collet nut 322 (FIG. 60). Preferably, tissue protector 170 helps lock hinge pin slider 133 in position on anterior arm 110 by making a tight engagement with the interlock apertures 127 on anterior arm 110. Then a hinge pin drill stop 173 (FIG. 61) is mounted to soft tissue protector 170. Hinge pin drill stop 173 prevents the surgeon from unintentionally drilling through the posterior cortex of the tibia too quickly or too deeply. Next, a drill 175 is advanced through hinge pin drill stop 173, soft tissue protector 170 and into the tibia until the drill chuck or collet 177 bottoms on drill stop 173 (FIG. 62). The surgeon can then progressively move drill stop 173 to the next position until the desired depth is reached. Then drill 175, hinge pin drill stop 173 and tissue protection 170 are removed. Finally, hinge pin 400 is inserted through hinge pin aimer 145 (FIGS. 63 and 64) and into the tibia. In this respect it will be appreciated that, inasmuch as hinge pin alignment tab 410 (FIG. 30) aligns with slots 153 (FIG. 15) on hinge pin aimer 145, one of the flats 405 on hinge pin 400 is always aligned with the osteotomy cut which will hereinafter be formed in the tibia. Collet nut 322 is used to secure hinge pin 400 to hinge pin aimer 145.

By virtue of the foregoing, it will be appreciated that hinge pin 400 is positioned in the patient's tibia so that hinge pin 400 extends (i) parallel to the A-P slope of the tibia, and (ii) parallel to the sagittal plane of the patient. As a result, when the osteotomy cut 20 (FIG. 1) is subsequently formed in the bone (see below) by cutting along the osteotomy cut plane 65 (FIG. 8) until the bone saw engages the hinge pin (and so that the perimeter of the bony hinge is defined by the location of the hinge pin), the bony hinge will extend (i) parallel to the A-P slope of the tibia, and (ii) parallel to the sagittal plane of the patient. By ensuring that hinge pin 400 is set in the aforementioned fashion, and hence ensuring that the bony hinge is so created, the final configuration of the tibia can be properly regulated when the bone cut is thereafter opened so as to form the open wedge osteotomy.

Figure 68:
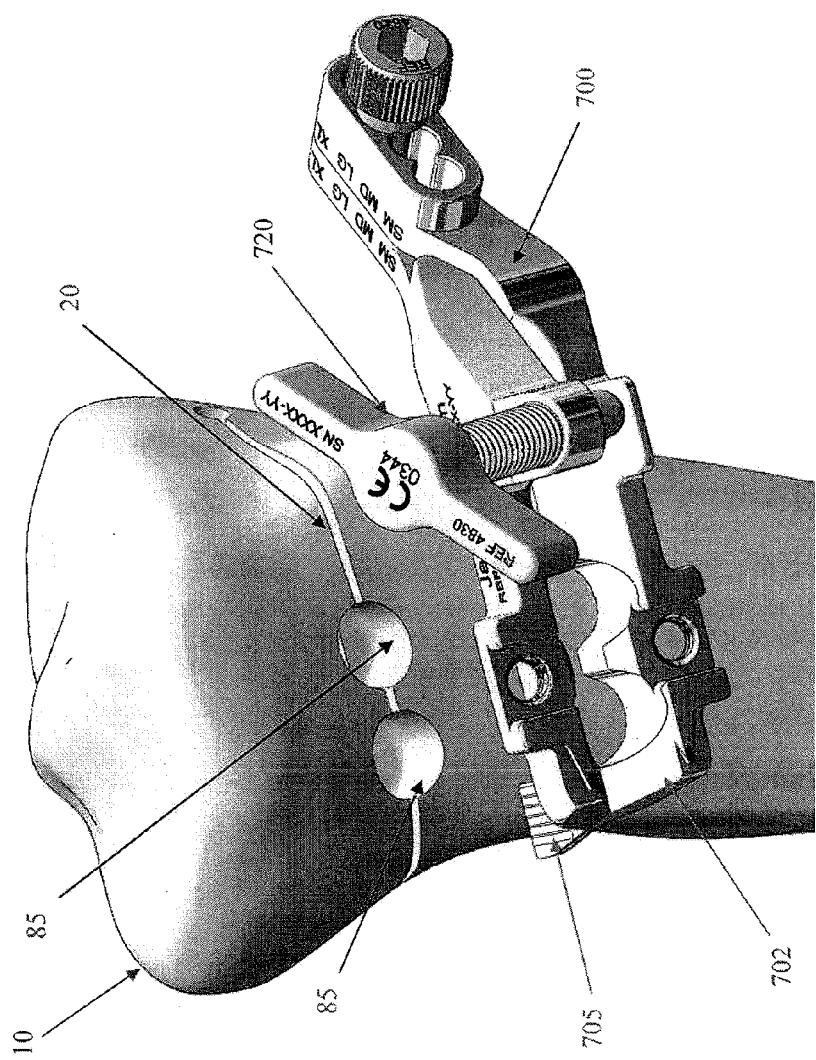
FIGS. 68-76 are schematic views showing the opening jack assembly opening a wedge-like opening in the bone.
Figure 69:
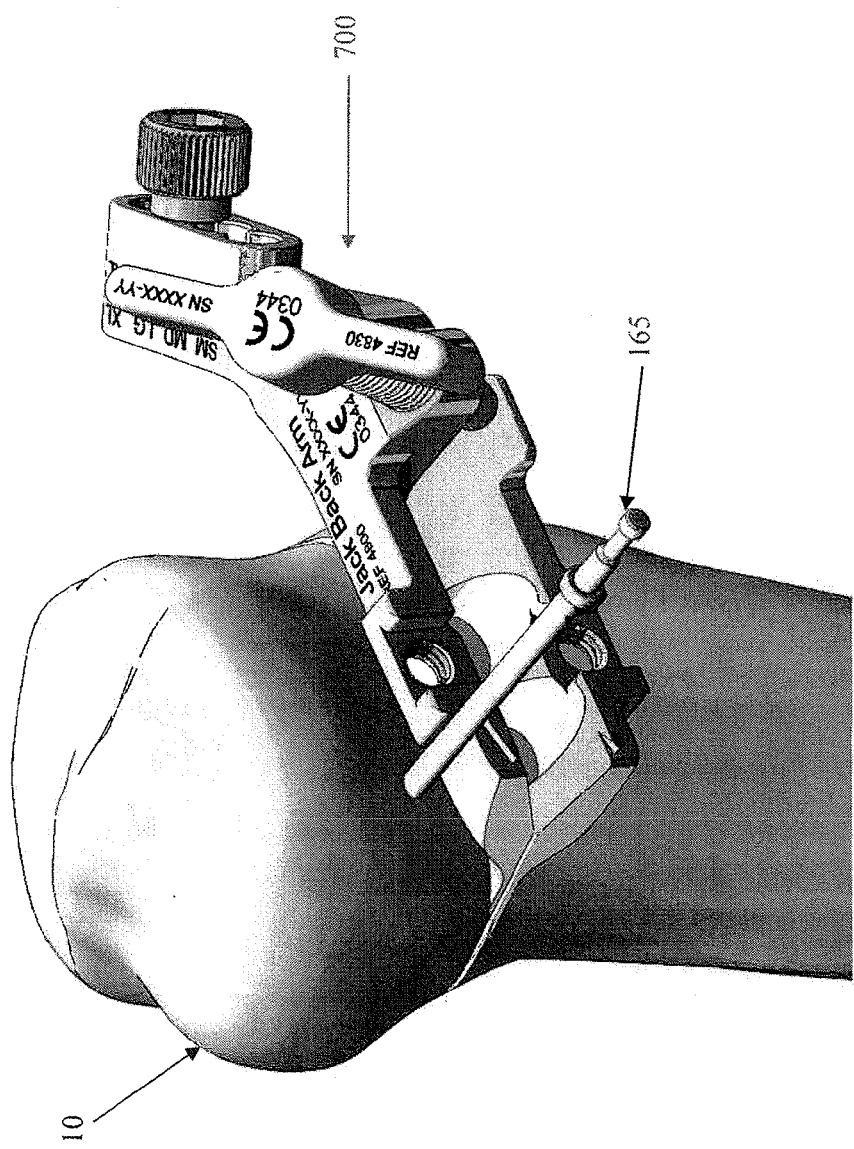
Figure 70:
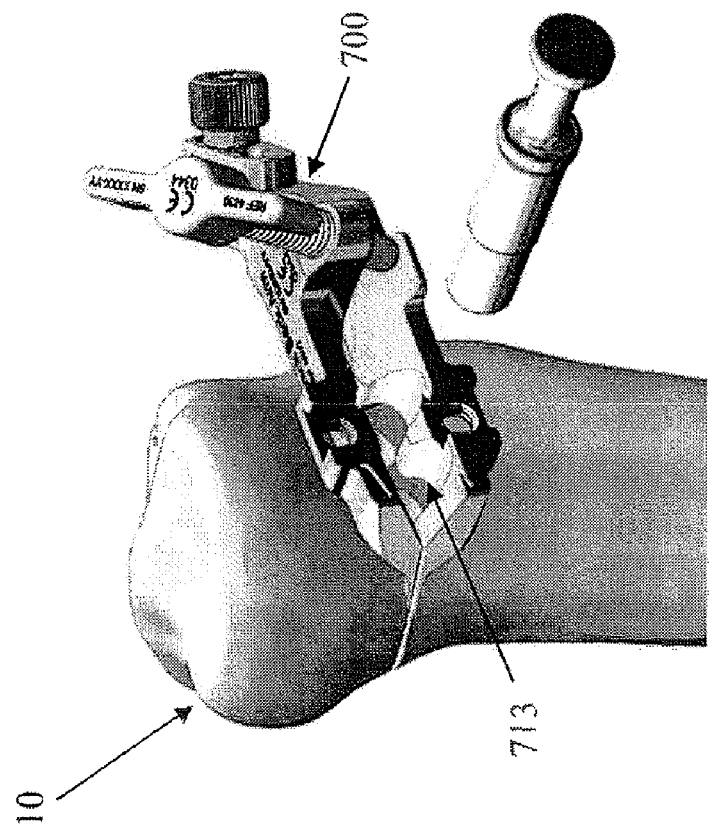
Figure 71:
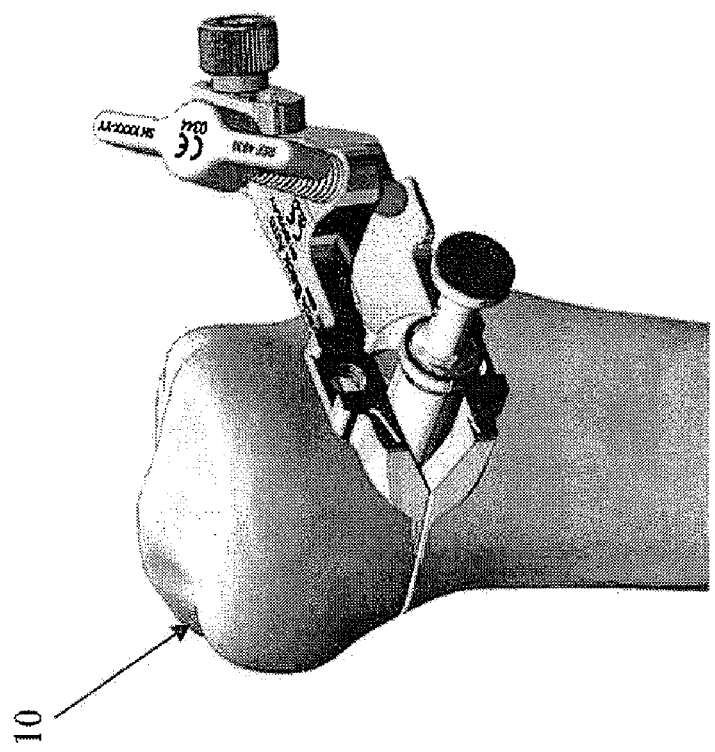
Figure 72:
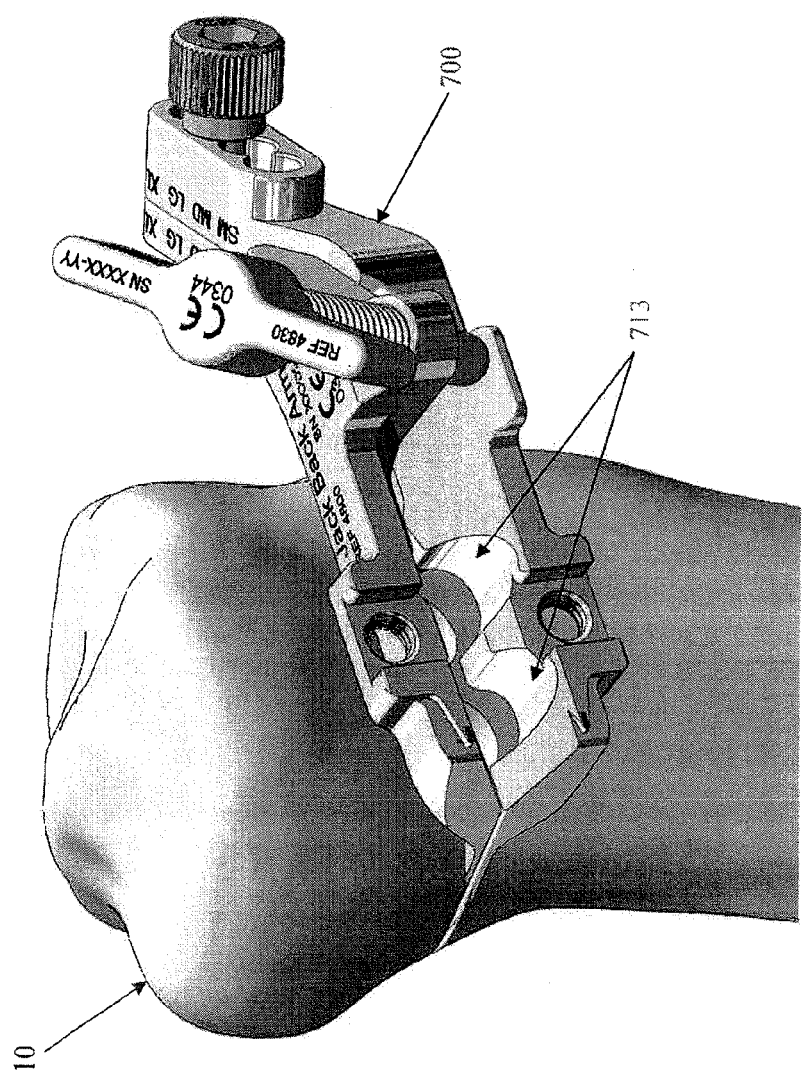
Figure 73:
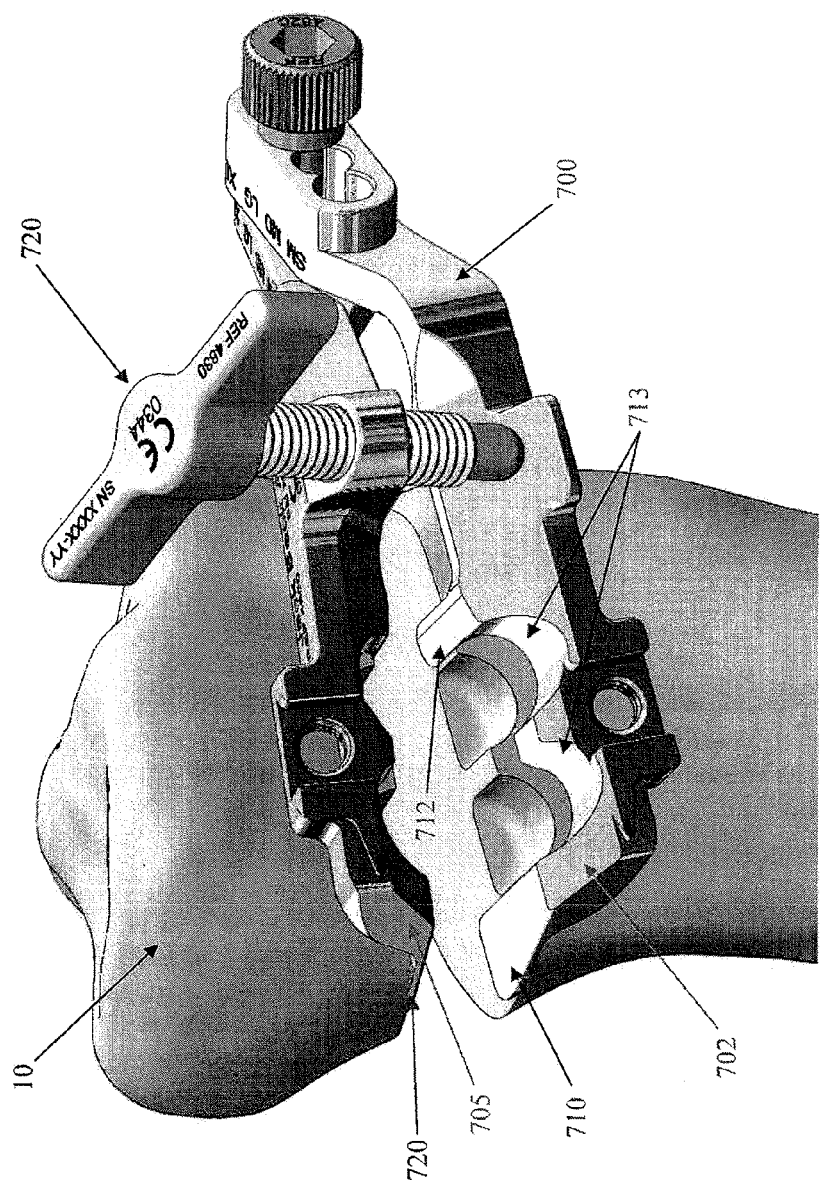
Figure 74:
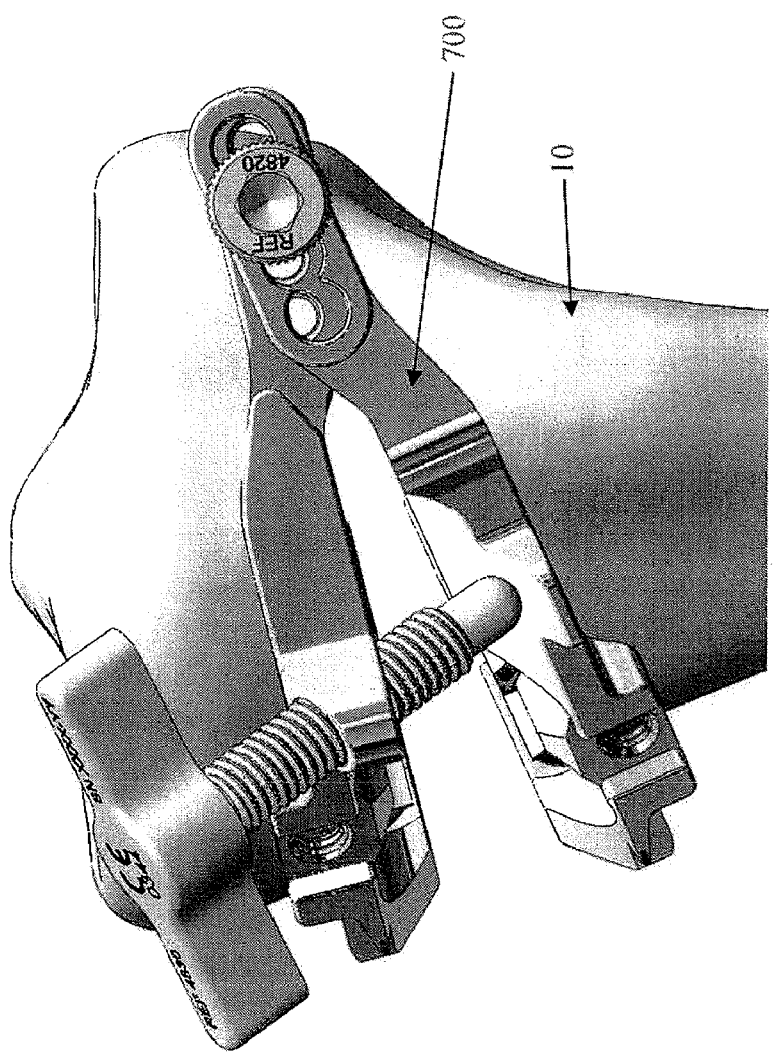

Once hinge pin 400 has been properly positioned in the bone (FIG. 64), an end mill (not shown) is inserted into one of the keyhole drill guides 210, whereby to form a first keyhole 85 (FIG. 65) in the tibia. The drilling procedure is then repeated for the second keyhole drill guide 210, whereby to form the second keyhole 85 in the tibia. Thus, keyholes 85 are formed so that the keyholes sit adjacent to one another, in a so-called "side-by-side" configuration. It should be appreciated that keyhole drill guide 200 is configured so that keyholes 85 will overlap the osteotomy cutting plane 65 to some extent (FIG. 68), so that when osteotomy cut 20 is thereafter formed and the tibia subsequently opened so as to create the wedge-like opening 25, keyholes 85 will overlap, and communicate with, the wedge-like opening 25. If biplanar alignment assembly 200 has not been removed from anterior arm 110 before this point in the procedure, it is preferably removed at this time.

Figure 65:
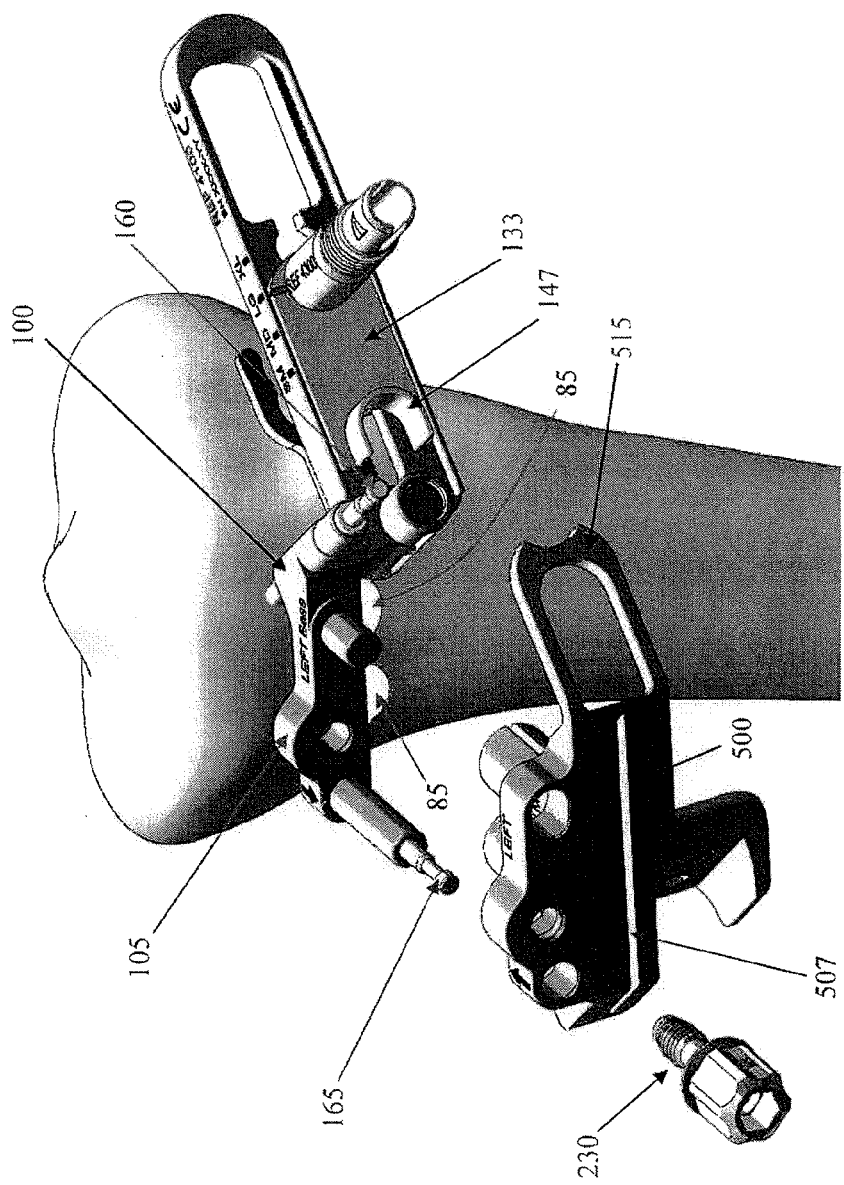
FIG. 65 is a schematic view showing the cutting guide being attached to the adjustable base assembly.

Once keyholes 85 have been formed in the tibia, keyhole drill guide 200 is replaced by cutting guide 500 (FIG. 65). More particularly, threaded fastener 230 is removed, keyhole drill guide 200 is dismounted from base 105, cutting guide 500 is mounted on base 105, and then cutting guide 500 is secured in position with threaded fastener 230. See FIG. 34. By virtue of the apparatus and the foregoing steps, when cutting guide 500 is mounted on base 105, saw guide slot 507 is aligned with osteotomy cutting plane 65.

Figure 37:
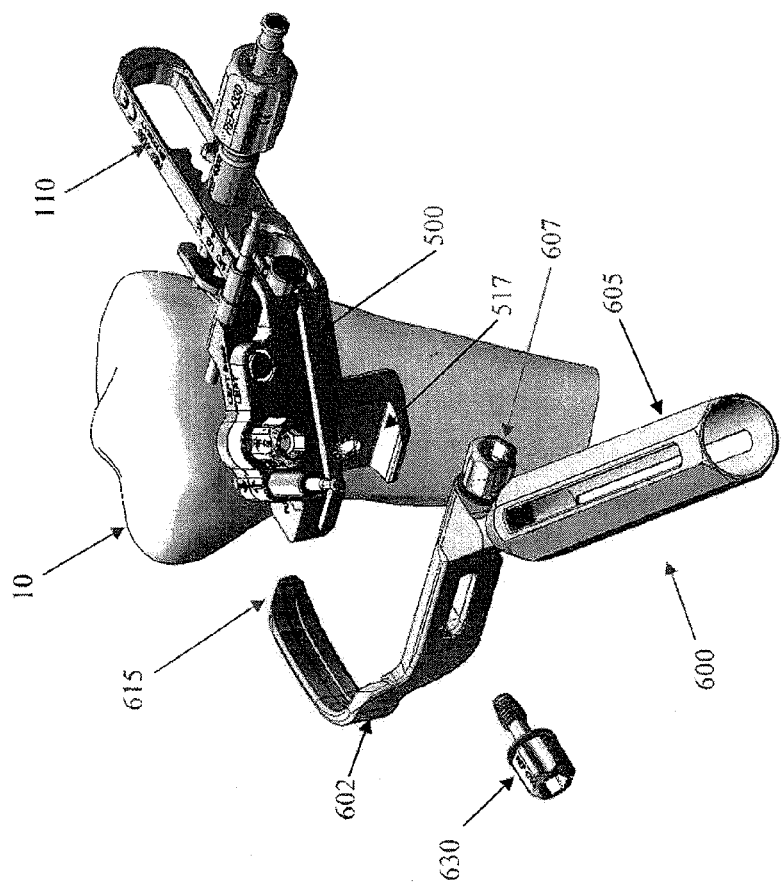
FIGS. 37-41 are schematic views showing a neurovascular shield assembly.
Figure 38:
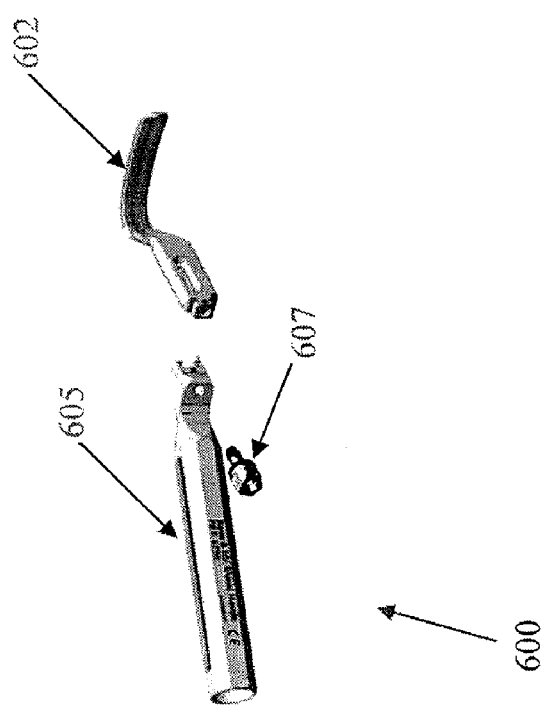
Figure 39:
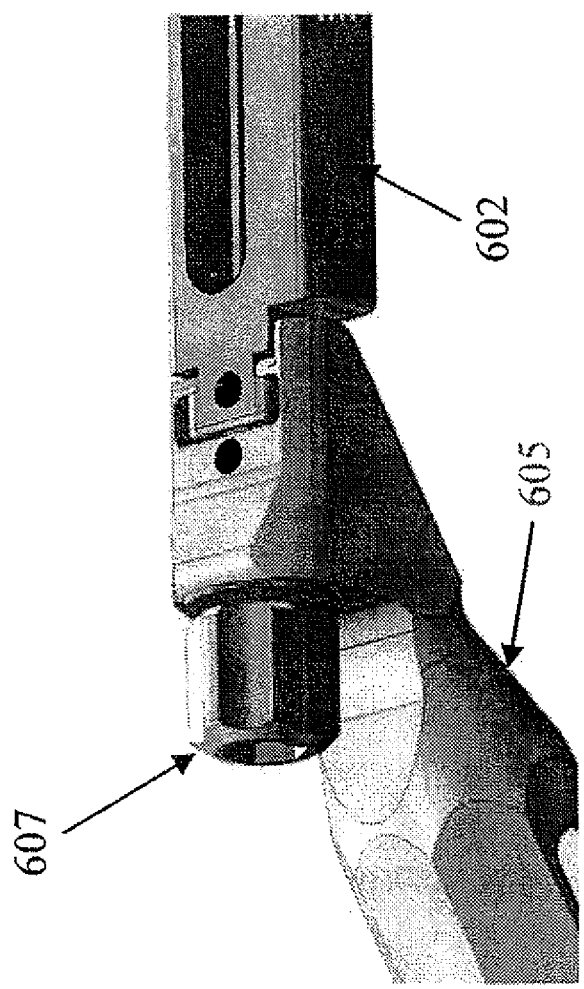
Figure 40:
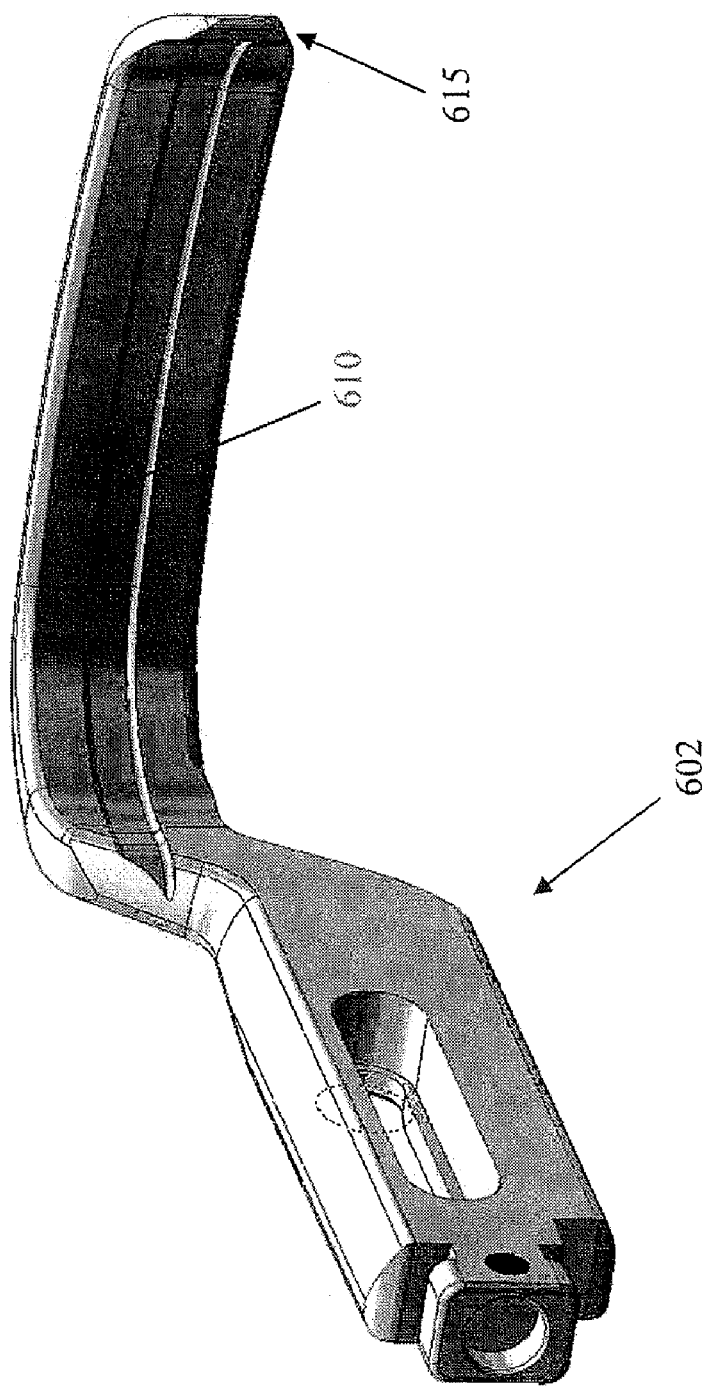
Figure 41:
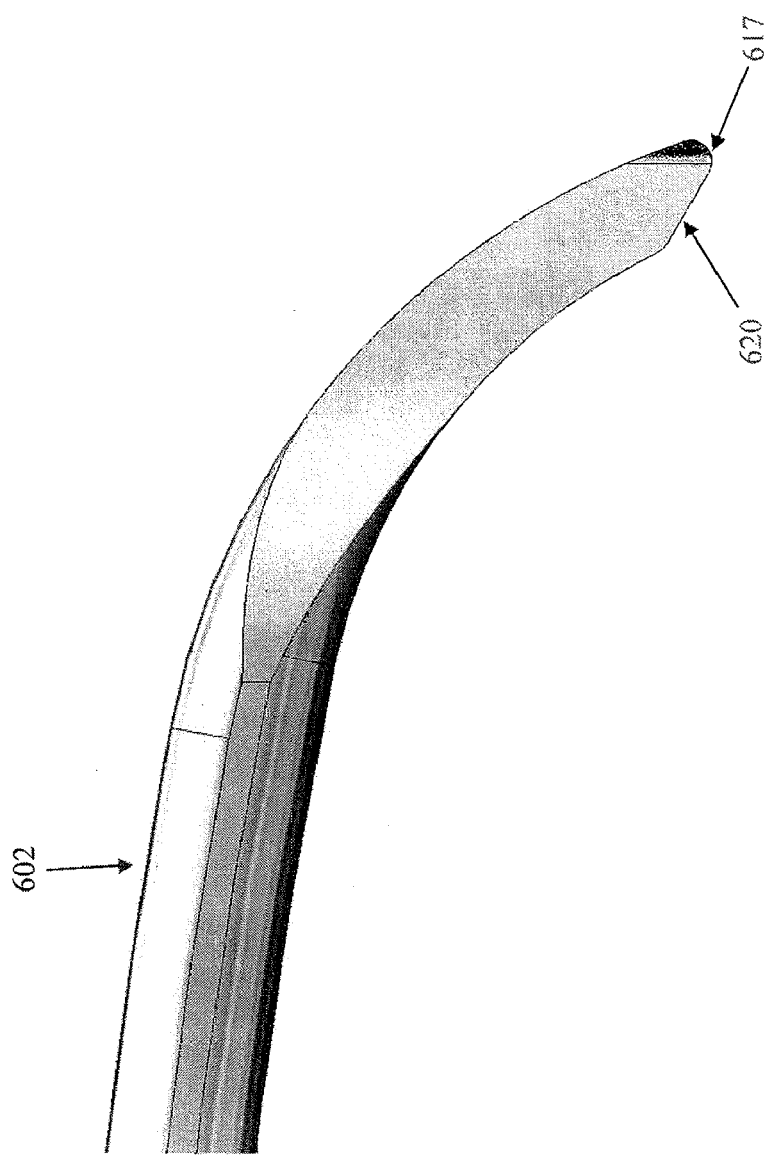

Next, and looking now at FIG. 37, neurovascular shield assembly 600 is inserted into the incision and worked along the posterior cortex of the tibia until its shaped tip 615 substantially crosses the axis of, and in some cases actually engages, hinge pin 400. Once neurovascular shield assembly 600 has been properly positioned, it is secured to cutting guide 500 by fitting neurovascular shield 602 in neurovascular shield mounting channel 517 and securing it in place with a threaded fastener 630 (preferably threaded fastener 630 is identical to threaded fastener 230 discussed above). Then threaded fastener 607 is unscrewed, and handle 605 is removed, leaving neurovascular shield 602 secured to base 105 and extending along the posterior cortex of the tibia, interposed between the tibia and the delicate neurological and vascular structures located at the back of the knee.

At this point, the instrumentation is ready to form the osteotomy cut, with saw guide slot 507 of cutting guide 500 properly aligned with the osteotomy cut plane, hinge pin 400 properly positioned at the far (lateral) limit of the osteotomy cut, patellar tendon protector 137 forming a protective shield for the patellar tendon, and neurovascular shield 602 forming a protective shield for the vascular and neurological structures at the back of the knee. In this respect it should be appreciated that cutting guide 500 is sized and shaped, and saw guide slot 507 is positioned, so that, in addition to being aligned with the hinge pin 400, the entry point of the cutting plane into the tibia is located at an appropriate location on the tibia's medial neck 66 (FIG. 8).

Next, a saw blade (not shown), attached to an oscillating saw (also not shown) is inserted into saw guide slot 507 of cutting guide 500. The osteotomy cut is then made by plunging the oscillating saw blade through saw guide slot 507 and into the bone. The saw blade is used to cut completely through the medial and posterior cortices. The saw is operated until the saw blade contacts neurovascular shield 602 and hinge pin 400. As the saw blade cuts through the tibia, it is constrained by saw guide slot 507, hinge pin 400 and neurovascular shield 602, so that the saw blade may only cut bone along the osteotomy plane, up to (but not beyond) the desired location of the bony hinge, and does not cut soft tissue. During cutting, patellar tendon protector 137 also ensures that the saw blade will not inadvertently cut the patellar tendon. Thus, saw guide slot 507, hinge pin 400, neurovascular shield 602 and patellar tendon protector 137 effectively define a "safe cutting zone" for the saw blade.

After the saw blade forms the desired osteotomy cut 20 along the cutting plane, the saw blade is removed, and a hand osteotome (not shown) of the sort well know in the art is inserted through saw guide slot 507 and into the osteotomy cut 20, and then the cut is completed through the posterior cortical bone near hinge pin 400 and neurovascular shield 602. Then the hand osteotome is removed.

Figure 66:
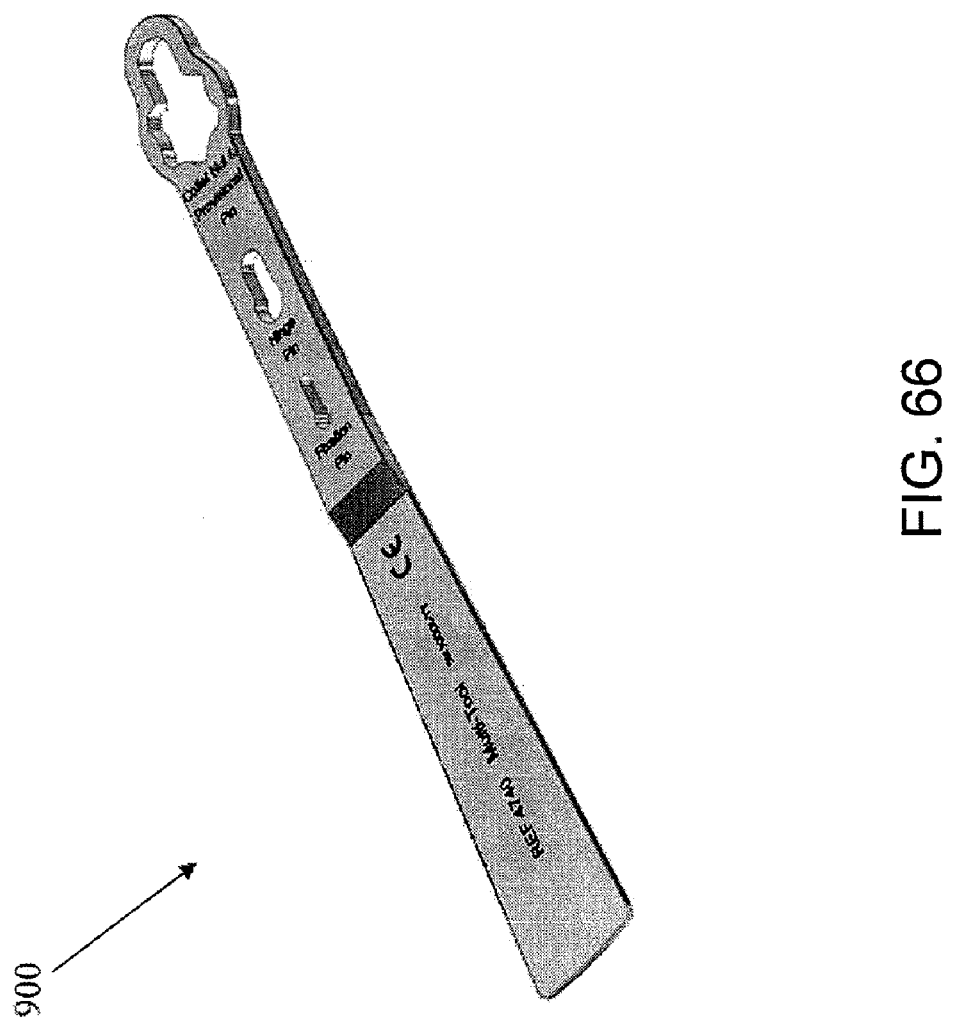
FIG. 66 is a schematic view showing a multipurpose tool.
Figure 67:
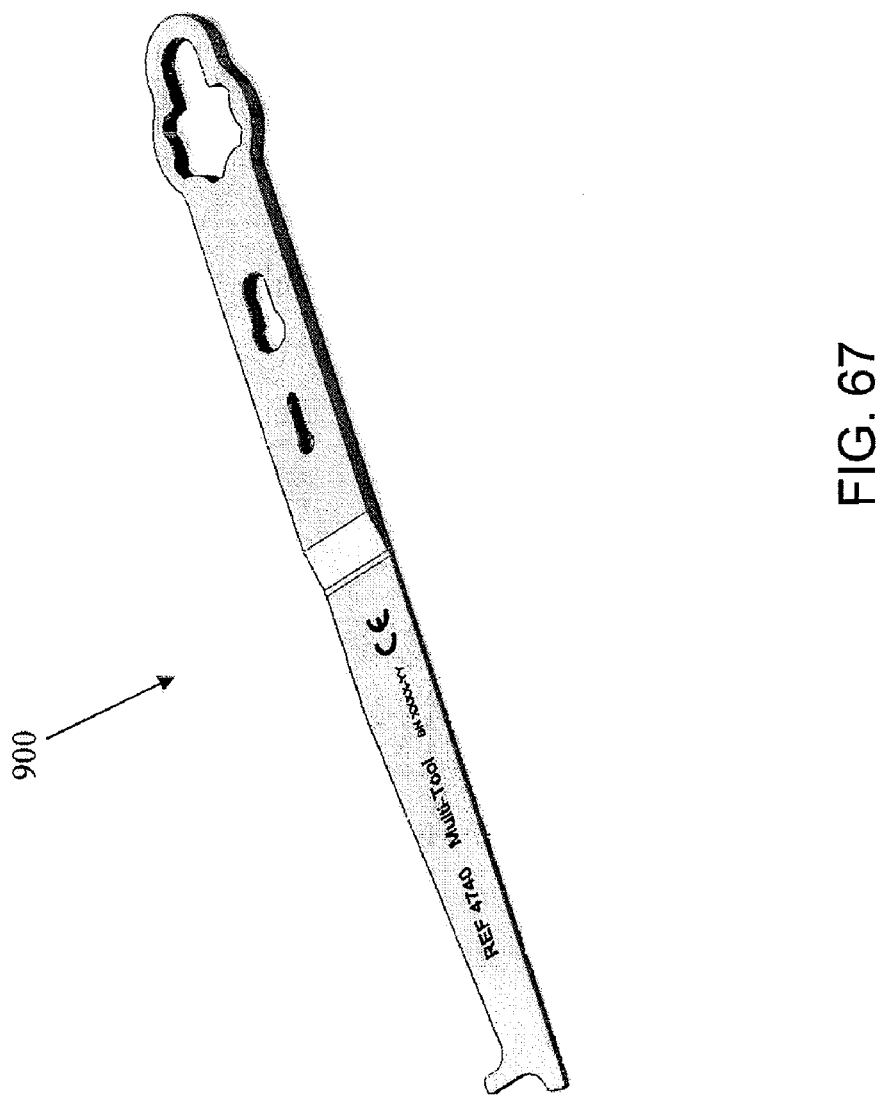
FIG. 67 is a schematic view showing another multipurpose tool.

If desired, the multipurpose tool 900 shown in FIG. 66, and/or the multipurpose tool shown in FIG. 67, may be used to probe the osteotomy cut to identify uncut bone from the sawing operation.

At this point the osteotomy cut 20 has been completed, with the osteotomy cut terminating on the lateral side at hinge pin 400, so that the bony hinge is properly positioned at the desired location, i.e., parallel to the A-P slope and perpendicular to the coronal plane.

Next, threaded fastener 630 is loosened and neurovascular shield 602 removed. Then threaded fastener 630 is loosened and cutting guide 500 is removed.

At this point, the desired osteotomy cut 20 has been formed in the tibia, with keyholes 85 formed side by side along the osteotomy cut. See FIG. 68.

Figure 75:
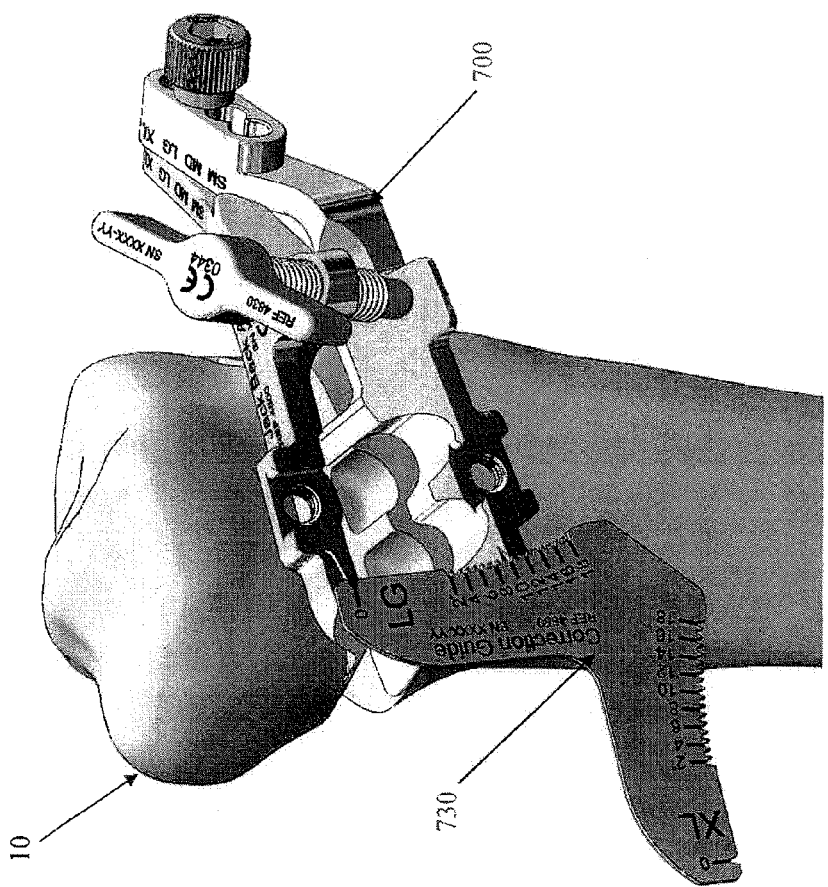
Figure 76:
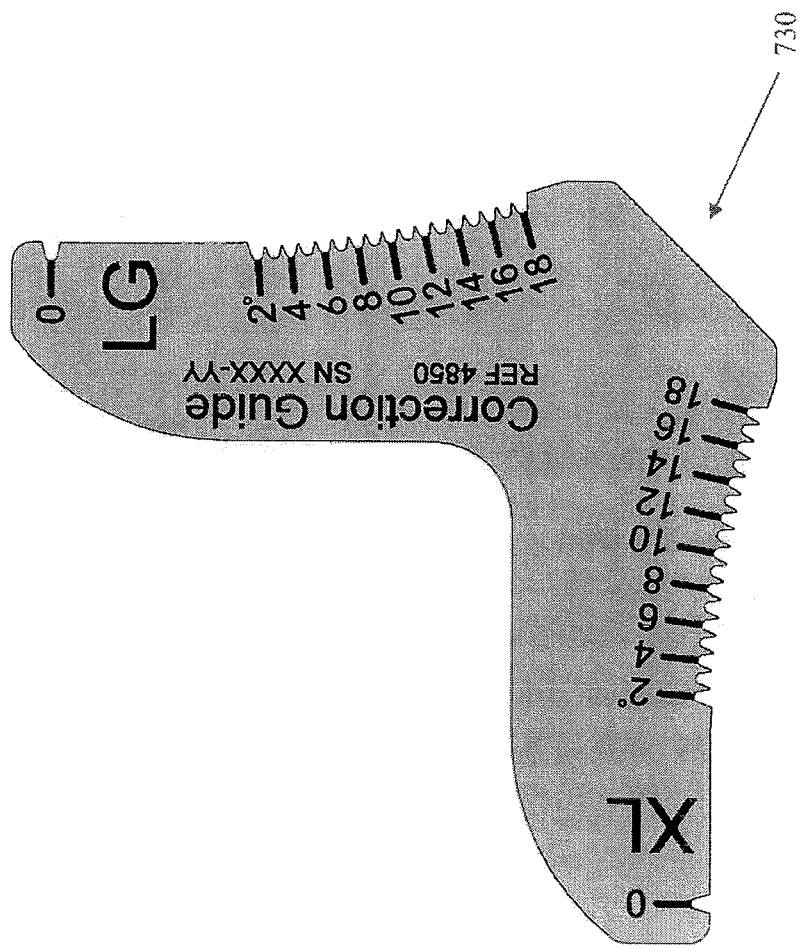

In order to complete the procedure, the bone must now be opened so as to reconfigure the tibia to the desired geometry, and then the tibia stabilized with the desired configuration, e.g., by inserting an implant into wedge-like opening 25. To that end, and looking now at FIGS. 68-78, opening jack assembly 700 is placed adjacent to the osteotomy cut, and the opening jack assembly is aligned with the tibia by visually aligning keyhole apertures 713 in the jack assembly with keyholes 85 in the tibia. Then opening jack assembly 700 has medial paddle 710 and anterior paddle 712 of bottom arm 702, and medial paddle 715 of top arm 705, placed in osteotomy cut 20, so that the medial and anterior paddles bear against the osteotomized surfaces of the tibia. Then turnkey 720 is rotated clockwise so as to open the jack to the desired correction angle. As this is done, a correction guide 730 (FIG. 75) is used to ensure that the osteotomy cut is opened to the correct angle. More particularly, a correction guide is selected that matches the size to which the opening jack assembly is configured, i.e., small (SM), medium (MD), large (LG) and extra large (XL). The center mark on the guide is aligned with the lower index mark on the jack, and the correction angle is read by aligning the correction guide to the upper index mark on the other jack arm. The correction guide incorporates two tibia sizes in each guide. The guide is generally V-shaped so the branch of the "V" that is not being used extends away from patient tissue.

Figure 77:
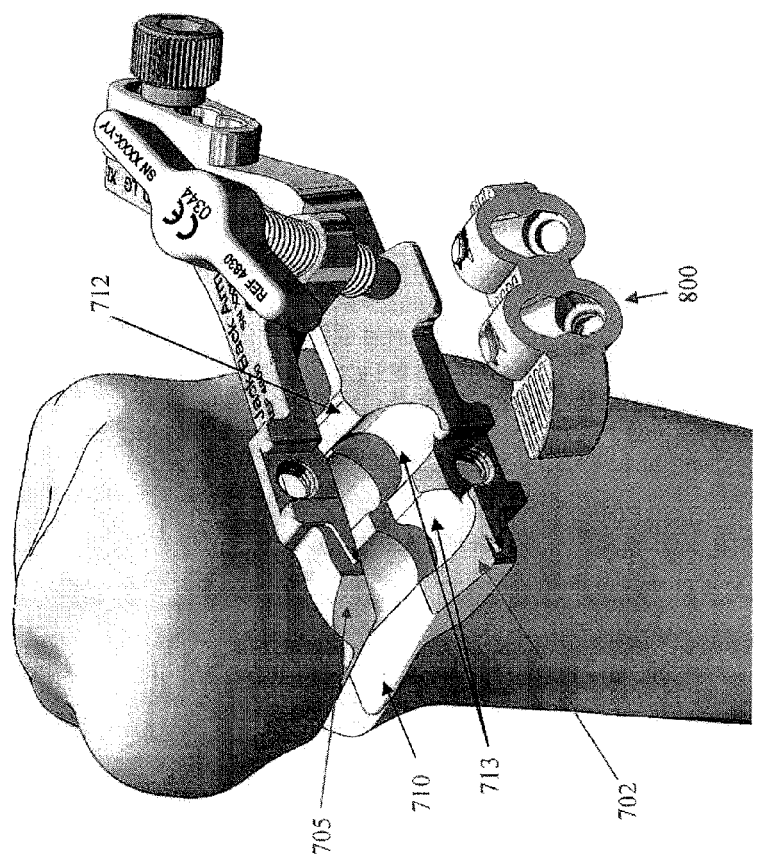
FIGS. 77 and 78 are schematic views showing the implant being inserted into the wedge-like opening in the bone.
Figure 78:
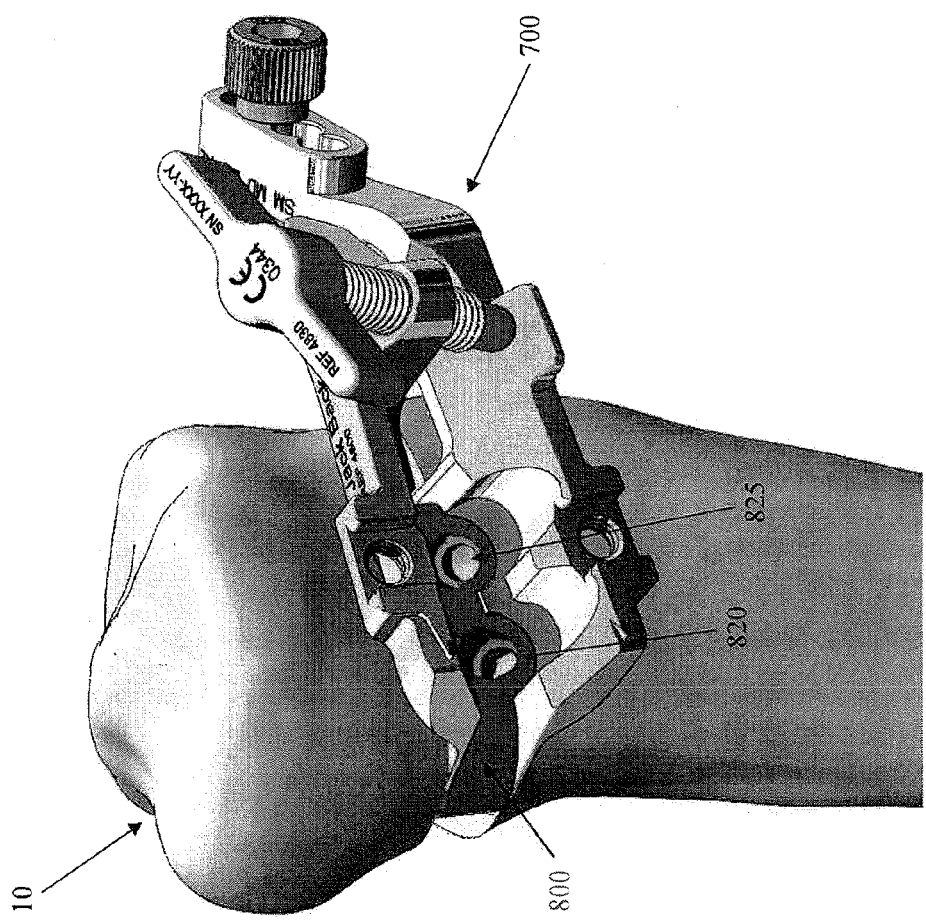

After the osteotomy is opened to the desired angle (FIG. 75), an implant 800 is selected and inserted through the jack assembly and into the prepared and opened osteotomy (FIGS. 77 and 78). More particularly, implant 800 is inserted through opening jack assembly 700 and seated in the osteotomy so that the body of the implant sits in wedge-like opening 25 and keys 820, 825 are seated in keyholes 85 formed in the tibia. Implant 800 is held in place by hand and then opening jack assembly 700 is removed. Attachment features for a handle or slap hammer may be provided to aid in the removal of the opening jack assembly.

After removal of opening jack assembly 700, implant 800 is fixed into place using screws 865. See FIGS. 50 and 54.

Visual Assembly Cues

It is desirable to give the surgical staff visual cues to aid in the proper assembly of the various components. Two types of visual cues are preferred.

Mating surfaces of the components can be identified by the use of color coding or engraved cross-hatching or engraved symbols: two surfaces with the same color (or engraved cross-hatching or engraved symbols) are intended to be matched together during assembly. This may be accomplished with the use of laser marking, or surface coating with materials such as Titanium Nitride or autoclave-safe epoxy paints.

Complementary alignment arrows or indicators may be placed on mating surfaces to indicate the direction of assembly. These alignment arrows or indicators are preferably positioned in close proximity to the mating features on each component.

In at least the case of the color coding, visibility of such coating alerts the surgical staff that all necessary components have not yet been assembled.

Multipurpose Collet Nut

It will be appreciated that collet nut 322 is multipurpose, in the sense that it may be used to retain different components of the instrumentation using various fastening methods.

More particularly, when holding biplanar alignment assembly 300 to anterior arm 110 of base 105, it serves as a simple threaded nut that retains the alignment mount axial with hinge pin aimer 145. However, when retaining tissue protector 170 on hinge pin aimer 145, the collet nut—together with the hinge pin slider 133—acts like a collet mechanism where an internal taper on the collet nut compresses the split collet feature of the hinge pin aimer radially onto the tissue protector as the collet nut is tightened. And when collet num 322 is used to retain hinge pin 400 into hinge pin slider 133, the internal taper of the collet nut compresses the tapered flange on the hinge pin axially against the end face of the hinge pin aimer.

Threaded Fastener 230

Threaded fastener 230 preferably has the following features:
 (i) scallops for preliminary tightening by hand;
 (ii) a hex recess for final tightening with a hex driver;
 (iii) a captive locking washer to prevent loosening due to vibration during drilling and sawing;
 (iv) a tapered tip to aid in alignment with threaded holes; and
 (v) a threaded taper to help align the fastener as it is tightened in order to reduce cross-threading.

Multipurpose Tool

A multipurpose tool 900 (FIGS. 66 and 67) is provided that performs the following functions:
 (i) the end of the tool is shaped to mimic the oscillating saw blade shape, allowing the surgeon to insert the blade through the cutting guide and probe the cortical surfaces looking for uncut bone from the sawing operation;
 (ii) the tool has an opening uniquely shaped to tighten and loosen the hinge pin collet nut;
 (iii) the tool has an opening to be used to remove the hinge pin when necessary; and
 (iv) the tool has an opening to be used to remove the fixation pins when necessary.

In an alternative form of the invention, the end of the multipurpose tool is shaped to allow the surgeon to explore the perimeter of the osteotomy cut in search of uncut cortical surfaces.

The Significance of Selected Aspects of the New Osteotomy Method and Apparatus

The use of hinge pin 400 is significant for a number of reasons:

(1) the oversized, circular diameter hole formed in the tibia by hinge pin 400, which forms the limit of bone cut 20, effectively displaces the stress forces created at the edge of the bony hinge when the cut is opened to form the wedge-like opening 25, thereby adding significantly to the effective strength of the bony hinge;

(2) by using hinge pin 400 to control the length of bone cut 20 (as measured from the medial aspect of the tibia to the hinge pin), the seat for the implant is always of known size, thereby simplifying proper fitting of the implant to its seat in the bone, and also reducing the inventory of different-sized implants which must be on hand during the surgery;

(3) with hinge pin 400 in place, bone resecting tools can be used with increased confidence, without fear of inadvertently cutting into, or even through, the bony hinge; and (4) since hinge pin 400 controls the depth of bone cut 20, the implant can be reliably manufactured to appropriately address the required degree of correction needed to effect knee realignment (e.g., a 4 degree implant slope will always provide a 4 degree angle of correction).

Furthermore, the provision of (i) hinge pin 400, neurovascular shield assembly 600 and patellar tendon protector 137 creates a "protection zone", and (ii) cutting guide 500 creates a closely constrained cutting path for the saw blade, thereby together ensuring that only the desired portion of the bone is cut. Among other things, the provision of neurovascular shield assembly 600 ensures that the delicate neurological and vascular tissues at the back of the knee are protected during cutting of the tibia.

The provision of keyholes 85 in the tibia, and the provision of keys 820, 825 in the implant, is significant inasmuch as they provide improved stabilization of the implant, particularly against rotational and shearing forces. This is particularly true inasmuch as keyholes 85 extend through the hard cortical bone at the periphery of the tibia.

Anterio-Lateral Osteotomies

In the foregoing description, the present invention is discussed in the context of performing an open wedge osteotomy using an antero-medial approach so as to effect a medial opening wedge osteotomy. Of course, it should be appreciated Oat the present invention may also be used in antero-lateral approaches so as to effect a lateral opening wedge osteotomy, or in other approaches which will be well known to those skilled in the art.

MODIFICATIONS

It will be understood that many changes in the details, materials, steps and arrangements of parts, which have been herein described and illustrated in order to explain the nature of the invention, may be made by those skilled in the art without departing from the principles and scope of the present invention.

What is claimed is:

1. Apparatus for use in performing an open wedge, high tibial osteotomy, the apparatus comprising:
   an adjustable base assembly, the adjustable base assembly comprising:
      a base;
      an anterior arm attached to the base;
      a first opening extending through the anterior arm and the base for receiving a frontal fixation pin for pivotally mounting the adjustable base assembly to a tibia;
      a hinge pin slider slidably mounted to the anterior arm for selective disposition along the anterior arm, the hinge pin slider including a hinge pin aimer for receiving a hinge pin;

a second opening extending through the base for receiving an antero-medial fixation pin for pinning the base to the tibia; and a biplanar alignment assembly for mounting to the adjustable base assembly, the biplanar alignment assembly comprising a biplanar alignment bar formed at least in part out of a radio-opaque material, wherein the biplanar alignment bar comprises a front section, a pair of side sections extending at a right angle to the front section, and a pair of vertical sections extending at a right angle to the pair of side sections, and further wherein the front section is configured to be mounted to the adjustable base assembly parallel to the anterior arm.

2. Apparatus according to claim 1 wherein the disposition of the hinge pin slider along the anterior arm depends upon the size of the tibia.

3. Apparatus according to claim 1 wherein the hinge pin aimer includes an orientation mechanism for ensuring a desired orientation for the hinge pin relative to the base of the adjustable base assembly.

4. Apparatus according to claim 1 further comprising a patellar tendon protector adjustably mounted to the adjustable base assembly.

5. Apparatus according to claim 4 wherein the patellar tendon protector comprises a patellar tendon protector blade, and further wherein the patellar tendon protector blade extends parallel to the anterior arm.

6. Apparatus according to claim 5 wherein the spacing between the patellar tendon protector blade and the anterior arm is adjustable.

7. Apparatus according to claim 1 further comprising a keyhole drill guide assembly for mounting to the base of the adjustable base assembly, the keyhole drill guide comprising: at least one keyhole drill guide; a medial locator tab; and an antero-medial locator tab.

8. Apparatus according to claim 1, wherein the biplanar alignment assembly comprises a biplanar alignment mount formed out of a radio-translucent material, and further wherein the biplanar alignment bar is mounted to the biplanar alignment mount and the biplanar alignment mount is mounted to the adjustable base assembly.

9. Apparatus according to claim 1 further comprising a hinge pin for deployment through the hinge pin aimer and into the tibia.

10. Apparatus according to claim 9 wherein the hinge pin comprises at least one flat for disposition toward the plane of an osteotomy cut.

11. Apparatus according to claim 10 wherein the hinge pin comprises an orientation mechanism for interaction with an orientation mechanism on the hinge pin aimer in order to ensure a desired orientation for the hinge pin.

12. Apparatus according to claim 1 further comprising a cutting guide for mounting to the base of the adjustable base assembly, the cutting guide comprising: at least one keyhole locating boss; and a saw guide slot.

13. Apparatus according to claim 12 wherein the cutting guide further comprises an anterior safety interlock tab for selectively engaging a counterpart element on the hinge pin slider so as to prevent an incorrectly-sized cutting guide from being used with the hinge pin slider.

14. Apparatus according to claim 1 further comprising a neurovascular shield for mounting to the base of the adjustable base assembly, the neurovascular shield being sized and shaped so as to protect the medial collateral ligament from damage from a saw blade advancing with an antero-medial approach.

15. Apparatus according to claim 1 further comprising an opening jack assembly for opening an osteotomy cut in a bone so as to form a wedge-like opening in the bone, wherein the opening jack assembly comprises: a bottom arm comprising a medial paddle and an anterior paddle; a top arm comprising a medial paddle; the bottom arm and the top arm being pivotally connected to one another; and an opening jack turnkey for opening the bottom arm and the top arm relative to one another.

16. Apparatus according to claim 15 wherein the opening jack turnkey is rotatably mounted to the top arm and engages the bottom arm.

17. Apparatus according to claim 1 further comprising an implant for disposition in the wedge-like opening in the bone.

18. Apparatus according to claim 17 wherein the implant comprises at least one key for disposition in a keyhole formed in the tibia.

19. A method for performing an open wedge, high tibial osteotomy, the method comprising:

providing:

an adjustable base assembly, the adjustable base assembly comprising:

a base;

an anterior arm attached to the base;

a first opening extending through the anterior arm and the base for receiving a frontal fixation pin for pivotally mounting the adjustable base assembly to a tibia;

a hinge pin slider slidably mounted to the anterior arm for selective disposition along the anterior arm, the hinge pin slider including a hinge pin aimer for receiving a hinge pin; and a second opening extending through the base for receiving an antero-medial fixation pin for pinning the base to the tibia;

a keyhole drill guide assembly for mounting to the base of the adjustable base assembly, the keyhole drill guide comprising:

at least one keyhole drill guide;

a medial locator tab; and an antero-medial locator tab;

a biplanar alignment assembly for mounting to the adjustable base assembly, the biplanar alignment assembly comprising a biplanar alignment bar formed at least in part out of a radio-opaque material;

a hinge pin for deployment through the hinge pin aimer and into the tibia;

a cutting guide for mounting to the base of the adjustable base assembly, the cutting guide comprising:

at least one keyhole locating boss; and a saw guide slot; and an implant for disposition in the wedge-like opening in the bone;

mounting the keyhole drill guide assembly to the base of the adjustable base assembly and mounting the biplanar alignment assembly to the base of the adjustable base assembly;

positioning the antero-medial locating tab against the medial aspect of the tibia, positioning the medial locating tab against the medial aspect of the tibia and, when viewing from the lateral view, aligning the biplanar alignment bar with the tibial plateau;

pivotally mounting the adjustable base assembly to the tibia with a frontal fixation pin;

rotating the anterior arm of the adjustable base assembly about the frontal fixation pin, and adjusting the position of hinge pin slider on the anterior arm, so as to align the hinge pin aimer with a desired position for the hinge pin;

passing the hinge pin through the hinge pin aimer and into the tibia;

drilling at least one keyhole in the tibia using the keyhole drill guide assembly;

replacing the keyhole drill guide assembly with the cutting guide;

forming a saw cut in the tibia using the cutting guide;

opening the saw cut so as to form a wedge-like opening in the bone; and inserting the implant into the wedge-like opening in the bone.

\* \* \* \* \*